United States Patent [19]
Carlson

[11] Patent Number: 5,952,313
[45] Date of Patent: Sep. 14, 1999

[54] LPS ANTAGONISTS AND METHODS OF MAKING AND USING THE SAME

[75] Inventor: Russell W. Carlson, Athens, Ga.

[73] Assignee: University of Georgia Research Foundation, Inc., Athens, Ga.

[21] Appl. No.: 08/649,408

[22] Filed: May 17, 1996

Related U.S. Application Data

[63] Continuation of application No. 08/202,968, Feb. 28, 1994, Pat. No. 5,648,343.

[51] Int. Cl.$^6$ ............................. A61K 31/70; C07H 3/04
[52] U.S. Cl. ...................... 514/53; 514/889; 536/123.13
[58] Field of Search ............................. 514/53, 54, 889; 536/123.1, 123.13, 17.2, 29.1

[56] References Cited

U.S. PATENT DOCUMENTS

| | | | |
|---|---|---|---|
| 4,495,346 | 1/1985 | Anderson et al. | 536/18.5 |
| 4,719,202 | 1/1988 | van Boeckel et al. | 514/61 |
| 4,844,894 | 7/1989 | Ribi et al. | 424/88 |
| 4,912,094 | 3/1990 | Myers et al. | 514/54 |
| 4,918,163 | 4/1990 | Young et al. | 530/387 |
| 4,929,604 | 5/1990 | Munford et al. | 514/53 |
| 4,987,237 | 1/1991 | Myers et al. | 549/222 |
| 5,013,661 | 5/1991 | Munford et al. | 435/197 |
| 5,041,427 | 8/1991 | Takayama et al. | 514/53 |
| 5,066,794 | 11/1991 | Shiba et al. | 536/55.3 |
| 5,134,230 | 7/1992 | Kusama et al. | 536/117 |
| 5,158,941 | 10/1992 | Jadhav et al. | 514/62 |
| 5,530,113 | 6/1996 | Christ et al. | 536/123.13 |

FOREIGN PATENT DOCUMENTS

| | | |
|---|---|---|
| 0 536 969 A2 | 5/1992 | European Pat. Off. . |
| 3836006 A1 | 3/1989 | Germany . |

OTHER PUBLICATIONS

Carlson, et al., Lipopolysaccharide Core Structures in *Rhizobium etli* and Mutants Deficient in O–Antigen, The Journal of Biological Chemistry, 270:1783–11788 (1995).

Carlson et al., The *Rhizobiaceae lipopolysaccharides* (LPSs), Abstract, 5th International Symposium on the Molecular Genetics of Plant–Microbe Interactions, Sep. 9–14, 1990.

Hollingsworth and Carlson, 27–Hydroxyoctacosanoic Acid is a Major Structural Fatty Acyl Component of the Lipopolysaccharide of *Rhizobium trifolii* ANU 843, The Journal of Biological Chemistry, 264:9300–9303 (1989).

Bhat and Carlson, Structure of a Galacturonic Acid Containing Lipid a from *Rhizobium phaseoli* CE3, Abstract, The First Congress of the International Endotoxin Society, May 10–12, 1990.

Bhat, et al., Distribution and Phylogenetic Significance of 27–Hydroxy–Octacosanoic Acid in Lipopolysaccharides form Bacteria Belongings to the Alpha–2 Subgroup of Proteobacteria, International Journal of Systematic Bacteriology, 41:213–217 (1991).

Bhat, et al., Ocurence of Lipid A Variants with 27–Hydroxyoctacosanoic Acid in Lipopolysaccharides form Members of the Family Rhizobiaceae, Journal of Bacteriology, 173:2155–2159 (1991).

Bhat and Calson, A New Method for the Analysis of Amide Rhizabiaceae, Journal of Cellular Biochemistry, Supplement 16D (1992), Keystone Symposia on Molecular & Cellular Biology, Mar. 5–27, 1992.

Carlson, et al., *Rhizobium lipopolysaccharides*; their structures and evidence for their importance in the nitrogen–fixing symbiotic infection of their host legumes, Plant Biotechnology and Development, Chapter 5, pp. 33–44, (Peter M. Gresshoff, Ed., CRC Press, 1992).

Bhat and Carlson, A new method for the analysis of amide–linked hydroxy fatty acids in lipid–As from gram–negative bacteria, Glycobiology, 2:535–539 (1992).

Takahashi et al., Structural Requirements of Endotoxic Lipopolysaccharides and Bacterial Cell Walls in Induction of Interleukin–1, Blood Purification, 6:188–206 (1988).

Carlson, et al., The Structure and Biosynthesis of Rhizobium Legauminosarum Lipid A, Lipopolysaccharides from Genes to Therapy 25–31 (Wiley–Liss, Inc., 1995).

Bhat, et al., Re–examination of the structures of the lipopolysaccharide core oligosaccharides from *Rhizobium leguminosarum* biovar phaseoli, Carbohydrate Research, 220:219–227 (1991).

Wood, et al. Genetic Derepression of a Developmentally regulated Lipopolysaccharide Antigen from *Rhizobium leguminosarum* 3841, Journal of Bacteriology, 171:4549–4555 (1989).

Price, et al., Lipid A biosynthesis in *Rhizobium leguminosarum*: Role of a 2–keto–3–deoxyoctulosonate–activated 4'phosphatase, Proc. Natl. Acad. Sci. USA, 93:7352–7356 (1995).

Price et al., Biosynthesis of a Structuarlly Novel Lipid A in *Rhizobium leguminosarum*: Indentification and Characterization of Six Metabolic Steps Leading from UPD–GlcNAc to 3–Deoxy–D–manno–2–Octulosonic Acid$_2$–Lipid IV $_A$, Journal of Bacteriology, 176:4646–4655 (1994).

Flad, et al., Agonists and Antogonists for Lipopolysaccharide–Induced Cytokines, Immunolbiol., 187:303–316 (1993).

(List continued on next page.)

*Primary Examiner*—Marian C. Knode
*Assistant Examiner*—Howard C Lee
*Attorney, Agent, or Firm*—Needle & Rosenberg, P.C.

[57] ABSTRACT

Compositions for antagonizing gram negative bacterial endotoxic activity. Methods of antagonizing gram negative bacterial endotoxic activity. Methods of treating septic or toxic shock in a patient. Methods of treating or preventing a lipopolysaccharide mediated disorder in a patient. A method of extracting lipopolysaccharide from a gram negative bacteria by releasing lipopolysaccharide from a gram–negative bacteria, contacting the released lipopolysaccharide with polymixin B-agarose, and eluting the lipopolysaccharide from the polymixin B-agarose with an eluting solution comprising at least 1% deoxycholate to obtain thereby an lipopolysaccharide product.

29 Claims, 27 Drawing Sheets

OTHER PUBLICATIONS

Lynn and Golenbock, Lipopolysaccharide Antagonists, Immunology Today, 13:271–276 (1992).

Rietschel, et al., Bacterial endotoxin: molecular relationships of structure to activity and function, The FASEB Journal, 8:217–225.

Raetz, Minireview–Bacterial Endotoxins: extraordinary lipids that activate eucaryotic signal transduction, Journal of Bacteriology, 175:5745–5753 (1993).

Carpati et al., Monophosphoryl lipid A attenuates the effects of endotoxic shock in pigs, J Lab Clin Med, 119:346–353 (1992).

Von Eschen, Monophosphoryl Lipid A and Immunotherapy, vol. II: Immunopharmacology and Pathophysiology, pp. 411–428 (1992).

Zähringer et al. "Molecular Structure of Lipid A, the Endotoxic Center of Bacterial LPS", *Adv. Carb. Chem. BCHM.*, (Ed. Derek Horton), vol. 50, pp. 211–276, (1994).

Johnson, Kenneth. "Isolation and Purification of Lipopolysaccharides", *Methods in Carb. Chem.*, (Ed. BeMiller & Whistler), vol. 9, pp. 3–10, (1993).

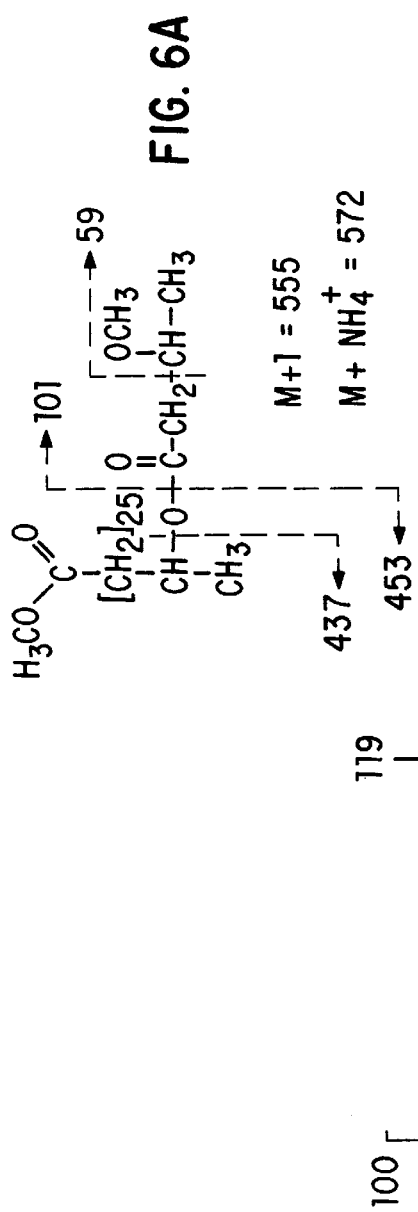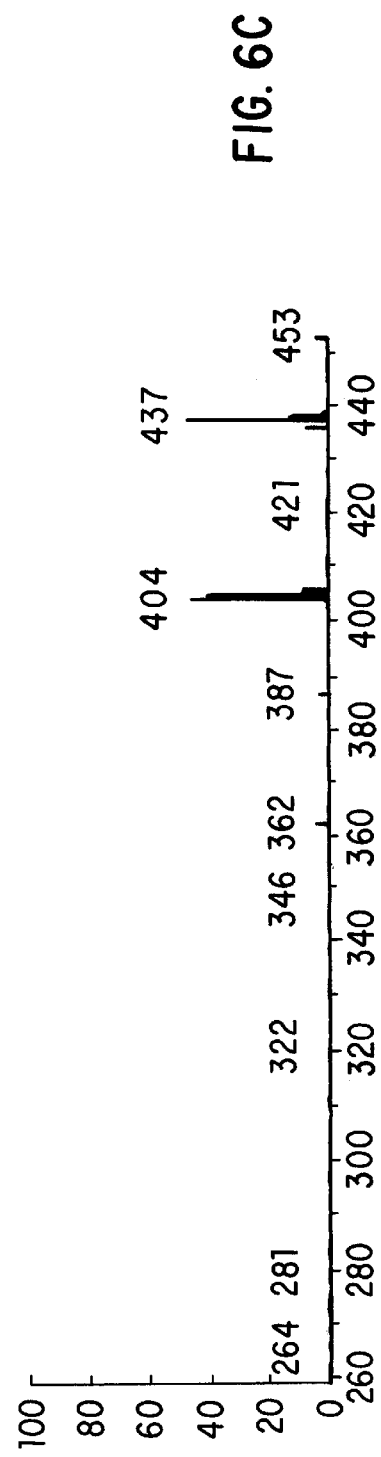
FIG. 6A
FIG. 6B
FIG. 6C

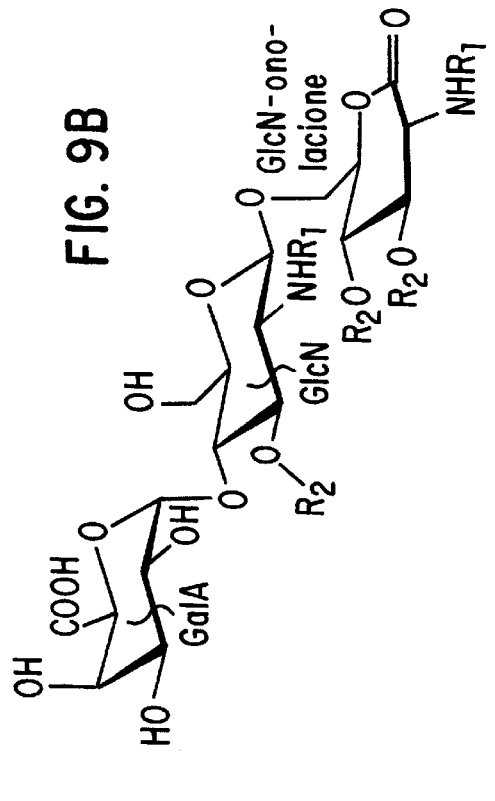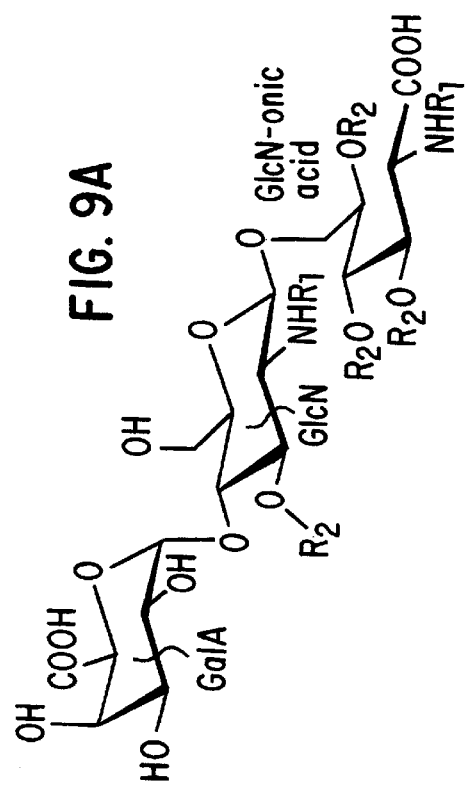

○―――○ LPS, *S. friedenau* H909
▼―――▼ LPS, *Rh. leguminosarum*
▽―――▽ LPS-OH, *S. minn.* R595
●―――● *Rh. leguminosarum*, Lipid A

M+1=708

Scan at 20.3333

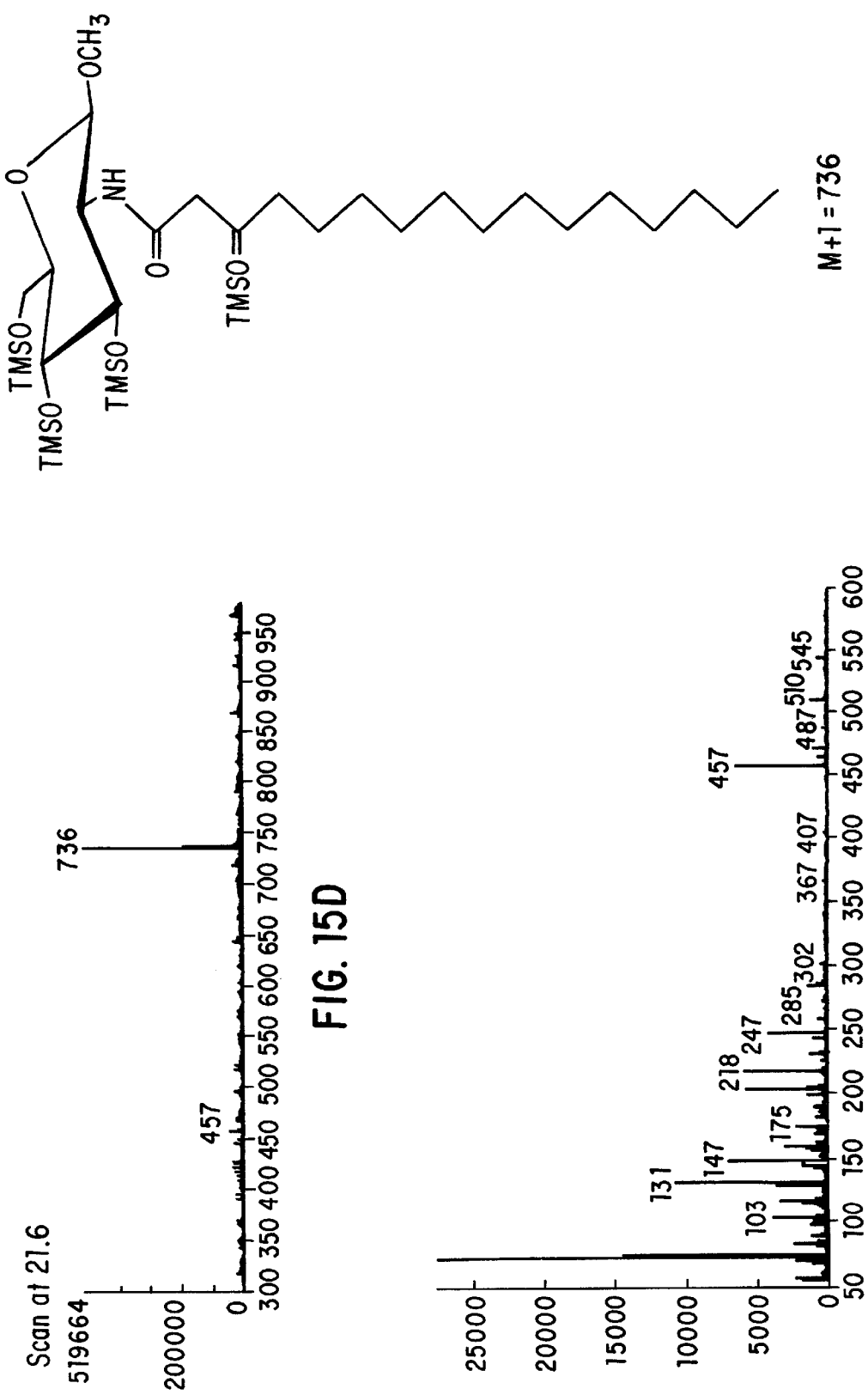

M+1 = 764

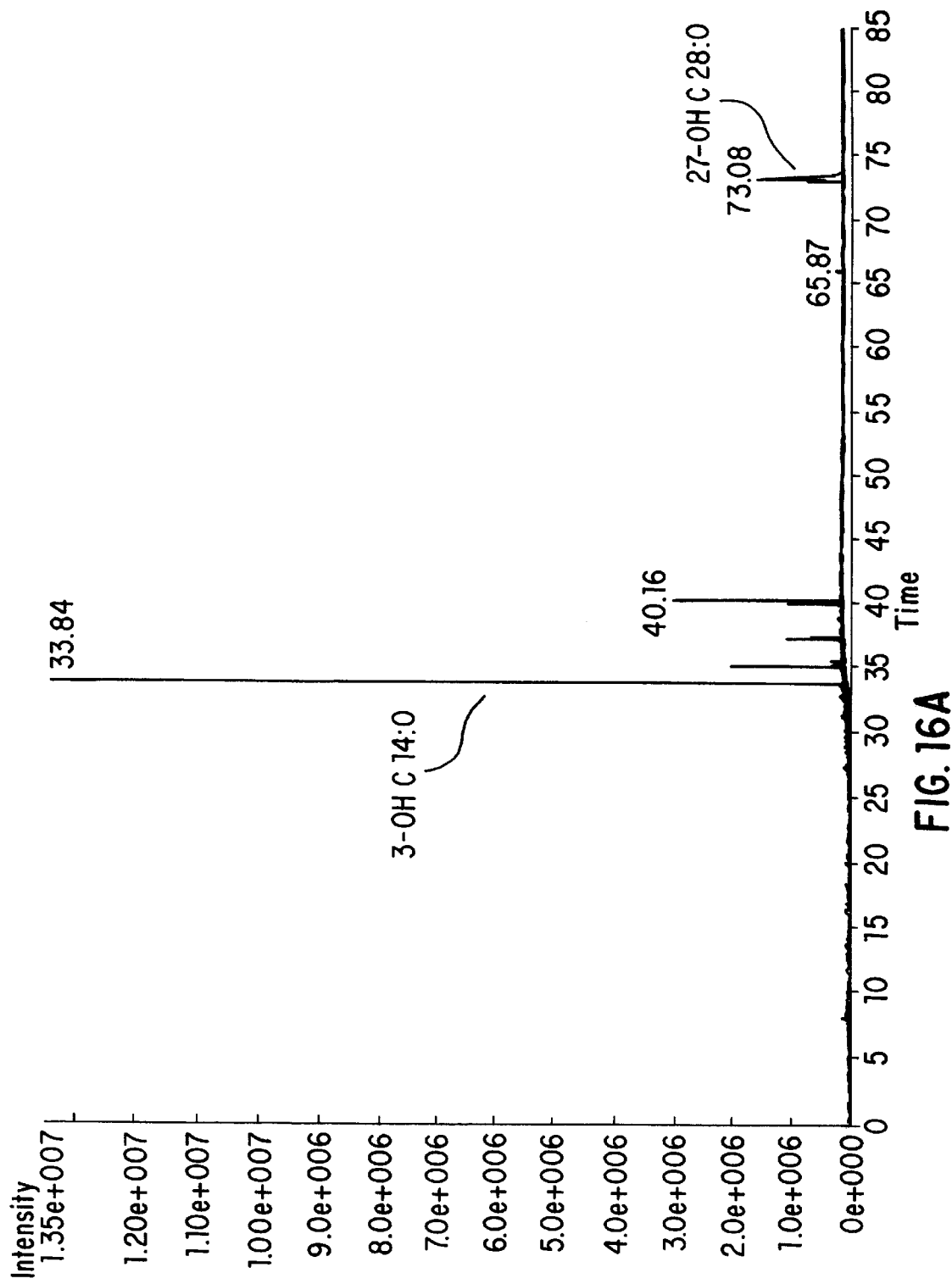

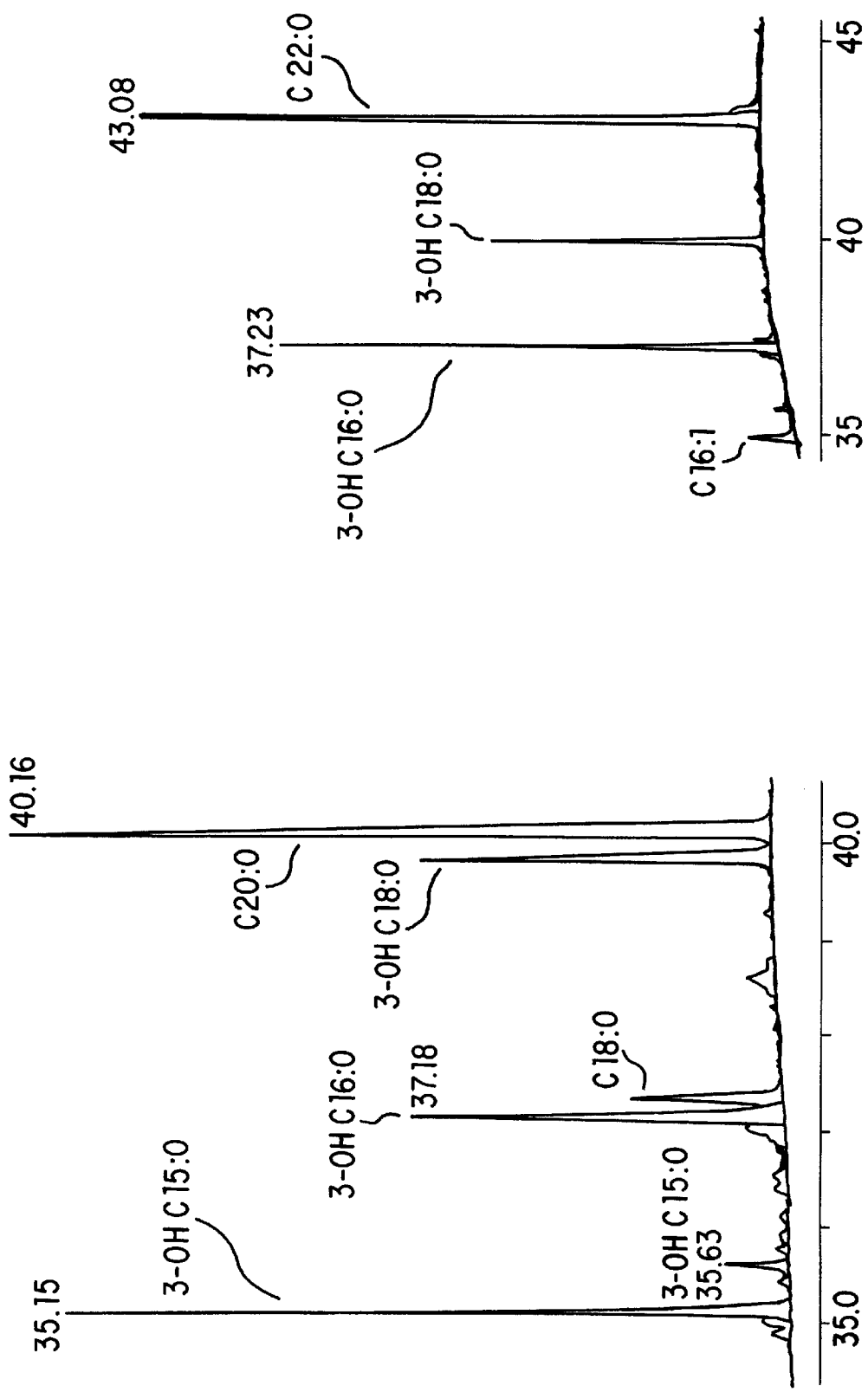

LPS ANTAGONISTS AND METHODS OF MAKING AND USING THE SAME

RELATED CASES

This application is a continuation of Applicant's U.S. Ser. No. 08/202,968, filed Feb. 28, 1994, now U.S. Pat. No. 5,648,343 the contents of which are hereby incorporated in full herein by this reference.

BACKGROUND OF THE INVENTION

This invention was supported, in part, by grant number R01 GM39583 from the National Institutes of Health. The United States government has certain rights in the invention.

FIELD OF THE INVENTION

This invention involves LPS and lipid A and antagonists and methods of making and using the same.

BACKGROUND

Bacteria of the Rhizobiaceae family are gram negative and able to form nitrogen-fixing relationships with legumes. The surface polysaccharides, including the lipopolysaccharides (LPSs), have been shown to play important roles in the symbiotic infection process.

Rhizobium and Bradyrhizobium LPS, as with others, have three structural regions: the lipid A, core oligosaccharide, and O-chain (or O side chain) polysaccharide. The rhizobial O-chain polysaccharides are highly variable and contain many methylated and deoxy glycosyl residues. See Stryer, *Biochemistry*, 2d Ed., W. H. Freeman and Co., New York, p. 74 (1981).

Before the discovery of the lipid A component of the LPS the term "endotoxin" was used to generically describe the effect of the LPS. The endotoxin from gram(–) bacteria is heat-stable, cell-associated, pyrogenic and potentially lethal. Lipid A is the causative agent of disorders such as septic or toxic shock and is related to other disorders such as Lyme disease.

The lipid A from enteric bacteria is somewhat variable. However, it is generally recognized that such a lipid A consists of a β-1,6-linked glucosamine disaccharide substituted at positions 4' and 1 by phosphomonoester groups. Fatty acids are linked to the hydroxyl and amino groups of the disaccharide to confer hydrophobicity to the lipid A. Also present in enterobacteria are amide and ester-linked D-3-hydroxy fatty acids, which consist of 14 carbons, e.g. O-hydroxymyristic acid. The C3—OH positions of these fatty acids may be further esterified with saturated fatty acids.

Despite these general characteristics, a degree of microheterogeneity occurs among diverse genera and species. Thus, Neisseria species produce 12 carbon 3-hydroxy fatty acids, saturated fatty acid substitution varies and the C'4-phosphoglucosamine disaccharide may contain a 4-amino-L-arabinose in salmonellae and *P. aeruginosa* as opposed to *E. coli* and Shigella. A very potent and toxic lipid A is a hexaacyl-1-4'-diphospholipid A. Structurally, a lipid A with one fewer or one more fatty acids will result in a biologically active, yet less toxic moiety. Removal of all fatty acids, however, deprives a particular lipid A of any biological activity. In addition, removal of either phosphate group results in significant loss of toxicity without loss of adjuvant activity. See Zinnser, *Microbiology*, 20th Ed., Appleton & Lange, Norwalk, Conn., pp. 84–86 (1992).

As discussed above, the cell associated, heat stable toxin of gram-negative bacteria is the lipopolysaccharide (LPS). While both the O-antigen and the core regions modulate the toxic activity of the LPS, it is the lipid A region that possesses the biological activity of the endotoxin (26,31). The structure of the lipid A from enteric bacteria (e.g. *E. coli*) is shown in FIG. 1. This structure is found in many gram-negative bacteria, and is the minimum structure required for toxic activity. Structural variations of this molecule that lack any one of the substituent groups; e.g. lacking a phosphate or fatty acyl substituent; are less toxic or not toxic (26,31). In addition, the minimal structure for viability of the bacterium requires the addition of two Kdo residues to C-6 of the terminal glucosamine residue (26).

In recent years, workers have discovered that endotoxin induced shock is caused by the ability of the LPS to stimulate host cells, such as macrophages, to produce excessive levels of cytokines (3,12,23). It is the excessive production of these cytokines, e.g. tumor necrosis factor (TNF) and interleukin I (IL-1), that results in toxic shock. At the present time it is probable that macrophages respond to lipid A by two possible mechanisms. The first mechanism involves the interaction of lipid A with a receptor on the macrophage cell surface which results in the release of signals that stimulate the synthesis of cytokines. This mechanism occurs with relatively high concentrations (nM) of lipid A (20,25). The second mechanism involves the binding of the lipid A (or LPS) by a serum protein called the LPS binding protein (LBP). This LPS-LBP complex then interacts with a receptor (CD14) on the surface of the macrophage resulting, again, in the production of signals with stimulate the synthesis of cytokines (20,30,34,35,42). This second mechanism is active at low lipid A concentrations (pM) (20).

The potent biological activity of lipid A has directed numerous research efforts toward developing useful applications of this activity. First, the necessity of a minimal structure for bacterial viability has led workers to synthesize compounds which inhibit the synthesis of this structure, and thereby, act as a new class of antibiotics (15,16). These inhibitors are based on their ability to inhibit Kdo synthase activity. Second, the ability of lipid A to stimulate the immune system has resulted in the investigation of the use of lipid A, and modified lipid A structures and analogs, as therapeutic anti-tumor agents (33,36), and, more recently, as adjuvants for vaccine development (1). Third, therapeutic agents which inhibit the interaction of lipid A with macrophages have been investigated as treatments for sepsis (13). These agents, have been polyclonal or monoclonal antibodies against common structural regions of lipid A (the core oligosaccharide or lipid A) (6,7,11,13,18,28,38,41,44,45), monoclonal antibodies against the LBP or CD14 proteins (2,11), and lipid A analogs which inhibit the binding of lipid A to LBP or CD14 (17,32). The use of antibodies in animal studies has warranted their testing in humans. Three different trials have given inconsistent results. However, in a subset of patients with gram-negative sepsis the results seemed to be beneficial and safe (13). The overall draw-back of this type of therapy is the high cost of acquiring these antibodies combined with the marginal benefits (as obtained in the recent clinical trials). Another useful approach is the use of lipid A analogs as antagonists for the toxic activity of lipid A. Several synthetic compounds have been examined (14,21,26,27,31,37), however the compound with the most potential is based on the lipid A from *Rhodobacter sphaeroides* (17,32) and on that from *Rhodobacter capsulatus* (FIG. 2) (19). This lipid A, which is unusual in that in contains unsaturated and 3-oxo fatty acyl residues, is not toxic and is a potent inhibitor of the ability of lipid A to stimulate cytokine production in an in vitro assay (17,22,32). Recently, a synthetic analog of this compound has been developed by Eisai (10) (FIG. 3) which is an even more potent lipid A antagonist.

The biological responses to LPS/Lipid A challenge are varied. Endotoxin is a potent pleiotropic biomodifier. Response to endotoxin challenge is species, dose, site, and route dependent. Even small doses of lipid A cause extreme changes in body temperature, hematology, immunology, and endocrinology of the subject. Lethal doses lead to hypotension, disseminated intravascular coagulation, irreversible shock, and, ultimately, death.

Most animals exhibit neutropenia and rapid induction of fever and hypotension upon challenge with lipid A from gram(−) bacteria. Intracerebral dosage of endotoxin requires a significantly reduced quantity for similarly devastating results. The most sensitive animals to endotoxin are humans. For instance, only about 2 ng LPS/kg from *Salmonella abortus equi* induces granulocytosis, a 7-hour fever of about 2° C. maximal temperature rise, and increased plasma cortisol levels. As opposed to the biphasic fever curve in other animals, the human fever response is monophasic. A dose of about 100 μg LPS is lethal in humans.

Known hematologic responses to LPS injection include production of cytokines such as Interleukin-1 (IL-1), Interleukin-6 (IL-6) and tumor necrosis factor (TNF). Significant release of endotoxin into the circulatory system leads to disseminated intravascular coagulation. The Schwartzman reactions are classic examples of endotoxin induced clotting responses. See Zinnser, supra at p. 86.

Lipid A is cleared from the host when human peripheral blood monocytes and neutrophils begin to deacylate the lipid A with an acyloxyacyl hydrolase which removes fatty acids esterified to β-hydroxymyristate acid esters. This deacylation results in significant reduction in toxicity of the resulting modified lipid A. The deacylated lipid A does, however, retain some adjuvant activity and ability to modulate or antagonize further response to LPS.

Current treatment for lipid A challenge includes the use of polymyxin B. Polymyxin B is thought to form a complex with LPS and thereby prevent the toxin from acting. In addition, monoclonal antibodies to tumor necrosis factor may be helpful. Although such treatments are helpful in alleviating some of the devastating effects of lipid A toxicosis, they do not constitute a completely safe and effective treatment. Therefore, there still exists a need for novel, effective treatments for lipid A associated disorders. In addition, there exists a need for a lipid A which is a potent adjuvant without the related toxicity. Finally, there exists a need for a lipid A which can be used to treat or prevent LPS associated disorders. The present invention provides the discovery that the lipid A from *Rhizobium leguminosarum* biovar phaseoli CE3 satisfies these needs.

There are two reports which describe a lipid A structure from two different strains of *R. leguminosarum* bv. trifolii (52,53). These reports provide incorrect structures for lipid A. Both of these reports describe structures which differ from each other, and which differ significantly from the structures described herein. Furthermore, the beneficial activities of the lipid A of this invention were not described, e.g., the use of this novel lipid A and its analogs as therapeutic agents to stimulate the immune system, as adjuvants for vaccines, and as lipid A or LPS antagonists to prevent or treat sepsis.

Polymixin B is a cationic cyclic peptide which acts by binding the anionic endotoxin. This antibiotic has been used to remove endotoxins from biochemical preparations so the preparations could be used for in vivo studies. Polymixin B-agarose affinity material is produced for that purpose (Detoxi-Gel™, Pierce Chemical Company). Biochemical preparations can be passed through Polymixin B-agarose affinity material and any endotoxin in the preparation will bind to the Polymixin B-agarose affinity material. The Polymixin B-agarose affinity material can be regenerated by removing bound endotoxin with 1% deoxycholate (DOC) solution. The Polymixin B-agarose affinity material can then be reused.

SUMMARY OF THE INVENTION

The present invention provides a composition for antagonizing gram negative bacterial endotoxic activity, comprising a pharmaceutically acceptable carrier and an antagonizing amount of a lipopolysaccharide from a *Rhizobium etli* or a *Rhizobium leguminosarum*.

In a further embodiment, the present invention provides a method of antagonizing gram negative bacterial endotoxic activity, comprising administering to a subject in need of such antagonization the composition described above.

In yet another embodiment, the present invention provides a method of antagonizing gram negative endotoxic activity, comprising administering to a subject in need of such antagonization an antagonizing amount of a lipopolysaccharide from a *Rhizobium leguminosarum* or a *Rhizobium etli*.

In a further embodiment, the present invention provides a method of antagonizing gram negative bacterial endotoxic activity, comprising administering to a patient in need of such antagonization an antagonizing amount of a lipid A from a *Rhizobium leguminosarum* or from a *Rhizobium etli*.

In another embodiment, the present invention provides a method of treating septic or toxic shock in a patient, comprising administering to the patient an effective amount of a lipid A from a *Rhizobium leguminosarum* or a *Rhizobium etli*.

In yet another embodiment, the present invention provides a method of treating or preventing a lipopolysaccharide mediated disorder in a patient, comprising administering to the patient an effective amount of a lipid A from a *Rhizobium leguminosarum* or a *Rhizobium etli*.

In yet another embodiment, the present invention provides a method of treating or preventing a lipopolysaccharide mediated disorder in a patient, comprising administering to the patient an effective amount of a lipopolysaccharide from a *Rhizobium leguminosarum* or *Rhizobium etli*.

In yet a further embodiment, the present invention provides a method of treating septic or toxic shock in a patient, comprising administering to the patient an effective amount of a lipopolysaccharide from a *Rhizobium leguminosarum* or a *Rhizobium etli*.

In a further embodiment, the present invention provides a method of extracting lipopolysaccharide from a gram negative bacteria, comprising releasing lipopolysaccharide from a gram-negative bacteria, contacting the released lipopolysaccharide with polymixin B-agarose, and eluting the lipopolysaccharide from the polymixin B-agarose with an eluting solution comprising at least 1% deoxycholate to obtain thereby an lipopolysaccharide product.

Additional advantages of the invention will be set forth in part in the description and Figures which follow, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIG. 9 shows a summary of the acid and lactone *R. leguminosarum* bv. phaseoli CE3 lipid A structures. $R_1$ and $R_2$ can be any of the designated fatty acyl substituents, however R1 must have the fatty acyl combinations shown in FIG. 8.

DETAILED DESCRIPTION OF THE PREFERRED EMBODIMENTS

Figure 2:
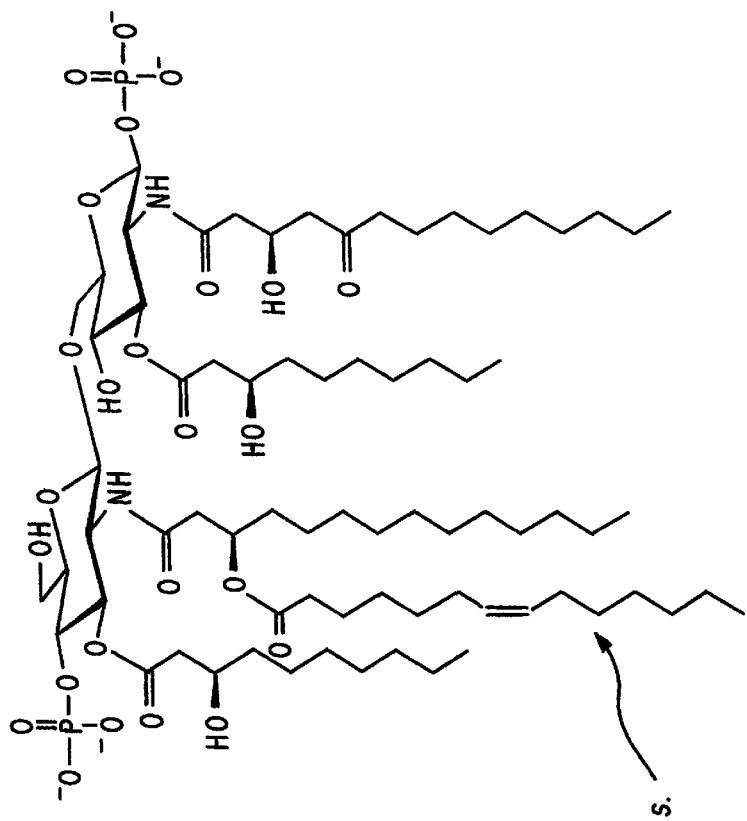
FIG. 2 shows the structure of the lipid A from *Rhodobacter sphaeroides* and *Rhodobacter capsulatus.*

The present invention may be understood more readily by reference to the following detailed description of preferred embodiments of the invention.

Before the present products, compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

The following abbreviations are used throughout this specification and are set forth here for convenience: LPS, lipopolysaccharide; Kdo, 3-deoxy-D-manno-2-octulosomic acid; DOC, deoxycholate; PAGE, polyacrylamide gel electrophoresis; HPAEC, high performance anion-exchange liquid chromatography; PMAA, partially methylated alditol acetates; FAB, fast atom bombardment; GLC, gas liquid chromatography; ES, electrospray; MS, mass spectrometry.

As used herein, the terms "antagonize", "antagonizing", "antagonism" and "antagonization" is meant to refer to the ability of one compound, product or composition to impede the effects of another compound, product or composition. For example, as is disclosed elsewhere herein, where *E. coli* LPS is known to stimulate TNF in a subject and the introduction of the LPSs from the disclosed *R. etli* or *R. leguminosarum* strains impede that stimulation, the LPSs from the disclosed *R. etli* or *R. leguminosarum* strains are said to antagonize the production of TNF by the *E. coli* LPS.

As used herein, the term "endotoxic activity" is used to describe the ability of gram-negative bacteria to induce a variety responses in a subject or patient, such as a human or animal, where the responses can include, but are not limited to, stimulation of cytokines including, but not limited to, TNF, IL-1 and IL-6 as well as the stimulation of pyrogens and any other responses known in the art to be associated with endotoxic challenge.

As used herein, the term "pharmaceutically acceptable" is meant to include any material, compound, product or composition that is not biologically or otherwise undesirable, i.e., the material may be administered to a subject without causing substantial deleterious biological effects or interacting in a deleterious manner with any of the other components of the composition in which it is contained. Actual methods of preparing such dosage forms are known, or will be apparent, to those skilled in this art; for example, see *Remington's Pharmaceutical Sciences* (Martin, E. W., ed., latest edition, Mack Publishing Co., Easton, Pa.).

As used herein, "admix" or "admixing" refers to the contacting, optionally in liquid media, of one or more ingredients.

As used herein, "agitate" or "agitating" refers to the movement of the specified article or other item sufficient for the desired purpose. For instance, agitation of a solution may occur via the use of a stirring rod.

As used herein, "optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution. Moreover, an "optional" step in a process is a step which may or may not be necessary.

As used herein, the term "dialyzing" is meant to refer to the process of separating two or more ingredients using a semi-permeable membrane.

As used herein, the term "eluting" is meant to refer to the removal of a particular target by dissolving the target in a solvent. Typically, after eluting the target, the target is recovered by evaporation of the solvent, if desired.

Additionally, the *"Rhizobium leguminosarum* biovar phaseoli CE3" bacteria has recently been reclassified and renamed as a *"Rhizobium etli"* strain (54). Therefore, the name *"Rhizobium leguminosarum"* can also identify the strain of bacteria named *"Rhizobium etli"* and the terms can be used interchangeably herein.

With these definitions in mind, the present invention provides a composition for antagonizing gram negative bacterial endotoxic activity, comprising a pharmaceutically acceptable carrier and an antagonizing amount of a lipopolysaccharide from a *Rhizobium etli* or a *Rhizobium leguminosarum*. In a further embodiment, the endotoxic activity is the stimulation of TNF. In yet a further embodiment, the lipopolysaccharide is from a *Rhizobium leguminosarum*. In an alternate embodiment, the lipopolysaccharide is from a *Rhizobium etli*.

In preferred embodiments of the present compositions and methods, the *Rhizobium etli* is a *Rhizobium etli* bv. CE109, *Rhizobium etli* bv. CE121, *Rhizobium etli* bv. CE350, *Rhizobium etli* bv. CE356, *Rhizobium etli* bv. CE357, *Rhizobium etli* bv. CE358, *Rhizobium etli* bv. CE359, or *Rhizobium etli* bv. CE360. In an alternate embodiment of the present compositions and methods, the *Rhizobium etli* is *Rhizobium etli* bv. CE3.

In yet another embodiment, the present invention provides the composition described above further comprising an antagonizing amount of the lipid A from a *Rhizobium etli* or a *Rhizobium leguminosarum*.

In preferred embodiments of the present compositions and methods, the pharmaceutically acceptable carrier is saline, mannitol, lactose, starch, magnesium stearate, sodium saccharin, talc, cellulose, glucose, sucrose, magnesium carbonate, water, aqueous dextrose, glycerol, ethanol or a mixture thereof.

In addition, in an alternate embodiment, the present invention provides a method of antagonizing gram negative bacterial endotoxic activity, comprising administering to a subject in need of such antagonization the composition as described above.

In yet another embodiment, the present invention provides a method of antagonizing gram negative endotoxic activity, comprising administering to a subject in need of such antagonization an antagonizing amount of a lipopolysaccharide from a *Rhizobium leguminosarum* or a *Rhizobium etli*. In a preferred embodiment, the Rhizobium is a *Rhizobium leguminosarum*. In a further preferred embodiment, the Rhizobium is a *Rhizobium etli*. In yet another preferred embodiment, the endotoxic activity is the stimulation of TNF.

In yet another embodiment, the present invention provides a method of antagonizing gram negative bacterial endotoxic activity, comprising administering to a patient in need of such antagonization an antagonizing amount of a lipid A from a *Rhizobium leguminosarum* or from a *Rhizobium etli*. In a preferred embodiment, the Rhizobium is a *Rhizobium leguminosarum*. In a further preferred embodiment, the Rhizobium is a *Rhizobium etli*. In yet a further embodiment, the endotoxic activity is the stimulation of TNF.

In yet another embodiment, the present invention provides a method of treating septic or toxic shock in a patient, comprising administering to the patient an effective amount of a lipid A from a *Rhizobium leguminosarum* or a *Rhizobium etli*. In a preferred embodiment, the Rhizobium is a *Rhizobium leguminosarum*. In an alternate preferred embodiment, the Rhizobium is a *Rhizobium etli*.

In another embodiment, the present invention provides a method of treating or preventing a lipopolysaccharide mediated disorder in a patient, comprising administering to the patient an effective amount of a lipid A from a *Rhizobium leguminosarum* or a *Rhizobium etli*. In one embodiment, the Rhizobium is a *Rhizobium leguminosarum*. In another embodiment, the Rhizobium is a *Rhizobium etli*.

The present invention also provides a method of treating or preventing a lipopolysaccharide mediated disorder in a patient, comprising administering to the patient an effective amount of a lipopolysaccharide from a *Rhizobium leguminosarum* or *Rhizobium etli*. In one embodiment, the Rhizobium is *Rhizobium leguminosarum*. In another embodiment, the Rhizobium is *Rhizobium etli*.

In yet another embodiment, the present invention provides a method of treating septic or toxic shock in a patient, comprising administering to the patient an effective amount of a lipopolysaccharide from a *Rhizobium leguminosarum* or a *Rhizobium etli*. In one preferred embodiment, the Rhizobium is a *Rhizobium leguminosarum*. In another embodiment, the Rhizobium is a *Rhizobium etli*.

In yet another embodiment, the present invention provides a method of extracting lipopolysaccharide from a gram negative bacteria, comprising releasing lipopolysaccharide from a gram-negative bacteria, contacting the released lipopolysaccharide with polymixin B-agarose, and eluting the lipopolysaccharide from the polymixin B-agarose with an eluting solution comprising at least 1% deoxycholate to obtain thereby an lipopolysaccharide product.

In a further embodiment, the present invention provides the above extracting method wherein the releasing step comprises admixing a bacterial pellet from a gram negative bacteria in a solution comprising i) ethylenediaminetetraacetic acid (EDTA); and ii) triethylamine (TEA) or triethanolamine (TEolA), in a 1:2 to 1:4 ratio of components i) to ii), wherein the resulting solution has a pH of 5.5 to 8.5; and agitating the mixture at a temperature of from 25° C. to 60° C. for a period of time sufficient to release the lipopolysaccharide from the bacterial pellet to obtain thereby a released lipopolysaccharide.

In a preferred embodiment, the eluting solution further comprises $NH_4HCO_3$.

Moreover, in yet another preferred embodiment, the polymixin B-agarose has been prewashed with a $NH_4HCO_3$ solution.

In yet another embodiment, the method further comprises, before the contacting step, dialyzing the released lipopolysaccharide. In a preferred embodiment, the dialysis is against a $NH_4HCO_3$ solution.

In a further embodiment, the temperature in the agitating step is from 30° C. to 50° C. In a preferred embodiment, the temperature in the agitating step is about 37° C.

In yet another embodiment, the ratio in the admixing step is 1:3. In a further embodiment, the pH of the solution in the admixing step is from 6.5 to 8.0. In a preferred embodiment, the pH of the solution in the admixing step is 7.0.

In yet another embodiment, the present invention provides the above method further comprising, after the dialyzing step, removing any insoluble debris from the released lipopolysaccharide.

In a further preferred embodiment, the present method further comprises, after the agitating step, centrifuging the released lipopolysaccharide and recovering the supernatant. In a preferred embodiment, the method further comprises, after the centrifuging step, admixing the supernatant with Tris HCl or $MgCl_2$ until the pH of the mixture is from 7.0 to 9.0 and incubating the pH adjusted mixture with an enzyme selected from the group consisting of an RNase, a DNase, and a protease. In a preferred embodiment, the pH of the pH adjusted mixture is about 8.0.

In yet another embodiment, the present invention provides the above described method, further comprising, after the contacting step, washing the polymixin B-agarose to remove impurities. In a preferred embodiment, the wash is performed with a $NH_4HCO_3$ solution. In yet another embodiment, impurities are also removed after the eluting step.

In yet another embodiment, the present invention provides the above-described method, further comprising recovering the lipopolysaccharide from solution after the eluting step. In a preferred embodiment, the lipopolysaccharide is recovered by freeze drying.

In a further preferred embodiment, the method further comprises regenerating the polymixin B-agarose by washing with a $NH_4HCO_3$ solution.

In yet a further preferred embodiment, the contacting step uses a column. In a preferred embodiment, the method further comprises applying a buffer or a denaturing agent to the polymixin B-agarose. In a preferred embodiment, the buffer is $NH_4HCO_3$, NaCl, or tetraethylammonium acetate. In a preferred embodiment, the denaturing agent is urea.

In yet another preferred embodiment of the invention, the contacting step is followed by washing with a $NH_4HCO_3$ solution.

In one embodiment, the above-described method may be used wherein the gram negative bacteria is a *Rhizobium leguminosarum* or a *Rhizobium etli*. In a further embodiment, the Rhizobium is a *Rhizobium leguminosarum*. In an alternate further embodiment, the Rhizobium is a *Rhizobium etli*.

In yet another preferred embodiment, the solution of the admixing step further comprises about 5% by volume of liquified phenol and wherein the resulting mixture is incubated at about 60° C. for about 15 minutes to about 2 hours. In a preferred embodiment, the incubation occurs for about 30 minutes.

In yet another embodiment, the present invention provides a method of antagonizing gram negative bacterial endotoxic activity, comprising administering to a patient the lipopolysaccharide obtained from the method described above.

In addition, the novel lipid A structures provided by the present invention are disclosed below. In particular, the present invention provides a purified compound comprising the following formula (hereinafter referred to as general structure (A)):

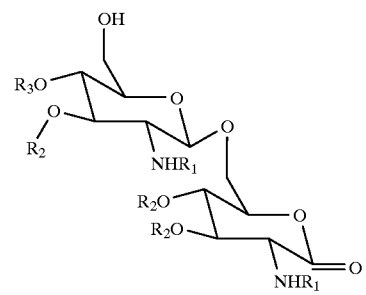

In this structure, $R_1$ is $H_3C$—$(CH_2)_m$—$COR_4H$—$CH_2$—CO—. In addition, in $R_1$, $R_4$ is one of the following moieties: H, $H_3C$—$(CH_2)_{10}$—CO— or $H_3C$—$(CH)_{12}$—CO—. Also, in $R_1$, m is either 10, 12 or 14. $R_2$ is either $H_3C$—$CHOR_5$—$(CH_2)_{25}$—CO— or $H_3C$—$(CH_2)_n$—$COR_6H$—$CH_2$—CO—. Furthermore, $R_5$ is either H or $H_3C$—CHOH—$CH_2$—CO—. $R_6$ is either H, $H_3C$—$(CH_2)_{10}$—CO— or $H_3C$—$(CH_2)_{12}$—CO—. In $R_2$, n is 10, 12 or 14. $R_3$ is selected from the group consisting of H, —$PO_4$ and

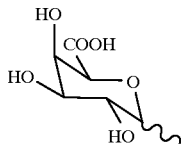

where the wavy line represents either an alpha or beta alkyl linkage.

In a preferred embodiment, the present invention provides a purified compound having the following formula:

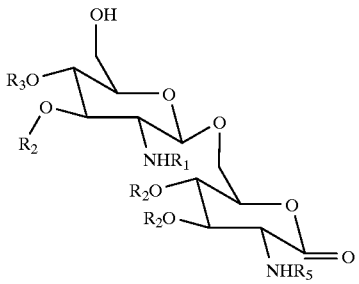

In this formula, $R_1$ is $H_3C—(CH_2)_{10}—CHOH—CH_2—CO—$. Furthermore, $R_2$ is either $H_3C—CHOR_4—(CH_2)_{25}—CO—$ or $H_3C—(CH_2)_{10}CHOH—CH_2—CO—$. $R_4$ is $H_3C—CH(OH)—CH_2—CO—$. $R_3$ is

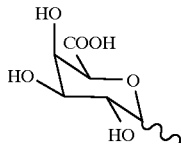

where the wavy line represents an alpha alkyl linkage. Finally, $R_5$ is $H_3C—(CH_2)_{12}—CHOH—CH_2—CO—$.

In another embodiment, the lipid A of this invention is a purified compound having the following formula (hereinafter referred to as general structure (B)):

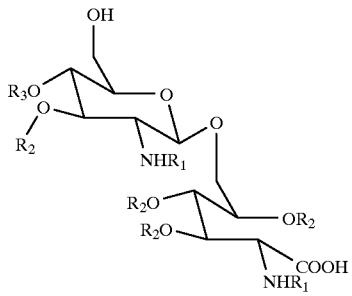

In this formula, $R_1$ is $H_3C—(CH_2)_m—COR_4H—CH_2—CO—$ where $R_4$ is either H, $H_3C—(CH_2)_{10}—CO—$ or $H_3C—(CH_2)_{12}—CO—$ and m is 10, 12 or 14. Next, $R_2$ is either $H_3C—CHOR_5—(CH_2)_{25}—CO—$ or $H_3C—(CH_2)_n COR_6H—CH_2—CO—$ where $R_5$ is H or $H_3C—CHOH—CH_2—CO—$ and $R_6$ is H, $H_3C—(CH_2)_{10}—CO—$ or $H_3C—(CH_2)_{12}—CO—$ and n is 10, 12 or 14. Finally, $R_3$ is H, $—PO_4$ or

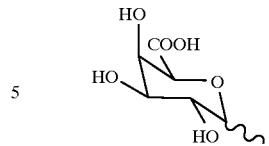

wherein the wavy line represents either an alpha or beta alkyl linkage.

In a preferred embodiment, this invention further provides purified lipid A compounds having the following formula:

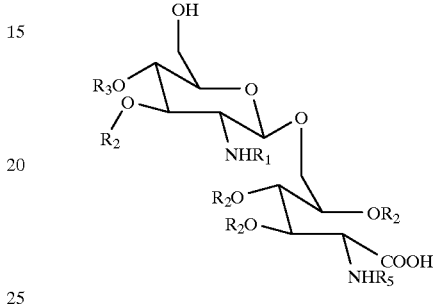

In this embodiment, $R_1$ is $H_3C—(CH_2)_{10}—CHOH—CH_2—CO—$. In addition, $R_2$ is either $H_3C—CHOR_4—(CH_2)_{25}—CO—$ or $H_3C—(CH_2)_{10}CHOH—CH_2—CO—$ where $R_4$ is $H_3C—CH(OH)—CH_2—CO—$. Also, $R_3$ is

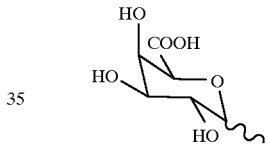

where the wavy line represents an alpha alkyl linkage. Finally, $R_5$ is $H_3C—(CH)_{12}—CHOH—CH_2—CO—$.

The present invention also provides a compositions comprising a heterogenous mixture of the above-identified (general structures (A) and (B) and accompanying text) compounds. By "heterogenous mixture" it is intended that more than one purified lipid A analog of *R. leguminosarum* disclosed herein can occur in the same composition. No specific amount, ratio, or number of different lipid A analogs is necessary to form a heterogenous mixture. Such a mixture simply contains two or more different lipid A molecules as described by the structures discussed herein.

Also provided is a method of stimulating the immune system in a subject, comprising administering to the subject an immune system stimulating amount of the compound described above.

In another embodiment, the present invention provides a method of treating toxic shock in a subject, comprising administering to the subject an effective amount of the compound of described above.

In another embodiment, the present invention provides a method of preventing toxic shock in a subject, comprising administering to the subject an effective amount of the compound of described above.

In yet another embodiment, the present invention provides a method of treating or preventing a lipopolysaccharide mediated disorder in a subject, comprising administering to the subject a lipopolysaccharide mediated disorder inhibiting amount of the compound described above.

EXAMPLE 1

Purification and Analysis of Rhizohium leguminosarum Biovar Phaseoli CE3

Growth of Bacteria. *Rhizobium leguminosarum* biovar phaseoli CE3 was obtained from Dr. Dale Noel (Marquette University, Milwaukee, Wis.). Bacteria were cultured in a tryptone/yeast extract medium supplemented with $Ca^{2+}$ as previously described (8,24). After growth to late log/early stationary phase the bacteria were harvested by centrifugation.

Lipopolysaccharide and Lipid A Purification. The LPS was extracted using hot phenol/water (39), treated with RNAse and purified by ultracentrifugation, or by gel filtration (9). Thus, with gel filtration, purity is indicated by the absence of proteins, nucleic acids, phospholipids and capsular polysaccharides and extracellular polysaccharides (9). With ultracentrifugation, the lipid A was released from the LPS by hydrolysis in aqueous 1% acetic acid (29) at 100° C. for 2 h. The released lipid A precipitated and was purified by centrifugation. The aqueous layer was extracted with methylene chloride and the lipid A in the organic layer was combined with the precipitate.

Thus, the lipid A purified by the above processes contains heterogenous mixtures of similar lipid A analogs (discussed further hereinbelow). In addition, the characterization/purification procedures result in further, novel lipid A analogs (the lactone analogs) which are likely not naturally present in *Rhizobium leguminosarum*.

Glycosyl Composition Analysis. Two methods were used to determine the glycosyl composition of the lipid A; the preparation and GLC-MS analysis of alditol acetates and of trimethylsilyl (TMS) methyl glycosides (43). In the case of alditol acetates, the carboxyl groups of the acidic glycosyl residues were reduced (converted to methyl esters) by methanolysis in methanolic 1 M HCl at 80° C. for 2 h. The solvents were evaporated with a stream of nitrogen and the sample was reduced with a 10 mg/ml solution of $NaBD_4$ in water. The excess $NaBD_4$ was destroyed with several drops of glacial acetic acid, and borate was removed by repeated (4 to 5) evaporations from methanol/acetic acid (9:1). The samples were then hydrolyzed, reduced and acetylated (43). The TMS methyl glycosides were prepared by methanolysis in methanolic 1 M HCl at 80° C. for 18 h, N-acetylated, and trimethylsilylated (43). Analysis was performed by GLC-MS using either a 15 m DB1 column (J&W Scientific, Illinois), or a 50 m methyl silicone column (Quadrex Corporation), and a 30 m SP2330 column (Supelco) for alditol acetates. Some GLC-MS analyses required chemical ionization (CI), which was performed on a Hewlett-Packard 5985 GLC-MS system with an ion source temperature of 150° C. using ammonia as the reactant gas.

Fatty Acid Analysis. Total fatty acids were released by complete methanolysis, as described above for the preparation of TMS methyl glycosides. The resulting fatty acid methyl esters were analyzed by GLC-MS, using the columns as described above.

Ester and amide-linked fatty acids were distinguished by preferential release of the ester-linked fatty acids using absolute (anhydrous) sodium methoxide as described by Wollenweber and Rietschel (40). Kraska methylation was attempted in order to characterize any amide-linked acyloxyacyl fatty acids (40). The amide-linked fatty acids were determined by mild methanolysis (4) via the preparation of TMS N-acylglucosamine methyl glycosides. Total fatty acids were removed from the lipid A by hydrazinolysis (40).

De-O-Acylation of Lipid A. Portions of the lipid A preparations were de-O-acylated in sodium methoxide (0.25 M) at 35° C. for 16 h. The lipid A (2–8 mg) was suspended in $CHCl_3$, and anhydrous sodium methoxide (0.5 M in methanol) was added to yield a final lipid A concentration of 2 mg/mL. Following incubation, the mixture was centrifuged (3000×g) and the supernatant was removed and analyzed for released fatty acids. The precipitate was again treated with sodium methoxide (0.5 M, without $CHCl_3$). The supernatants from the two methoxide treatments were combined, and the remaining precipitate fraction was dissolved in water, acidified to pH 4.0 with dilute acetic acid, and washed two times with hexane:chloroform (1:1, v:v) to remove residual fatty acids. Portions of the precipitated de-O-acylated lipid A were converted to the acid (COOH) form by passage through a Dowex 50-($H^+$) column, eluted with water and then with water:methanol (1:1).

Glycosyl Linkage Analysis. Permethylated alditol acetates were prepared using a modification of the Hakomori procedure as described by York et al. (43), and analyzed by GLC-MS using a 30 m SP2330 column from Supelco. β-Elimination was carried out on the permethylated lipid A (prior to acid hydrolysis) by stirring overnight in 2 M dimethylsulfoxide anion (potassium salt) in dimethylsulfoxide. The β-elimination product was ethylated (using ethyl iodide) or trideuteromethylated using ethyl iodide or trideuteromethyl iodide, respectively. Alditol acetates were prepared and analyzed as described above (43). When necessary, the carboxymethyl groups of the permethylated samples were reduced using lithium triethylborodeuteride ("Superdeuteride") (Aldrich Chemical Co., Milwaukee, Wis.) (43).

Location of the fatty acyl residues was determined by diazomethane methylation of the lipid A under neutral conditions, using silica gel as the catalyst (46), followed by the preparation and GLC-MS analysis of the partially methylated alditol acetates.

NMR Spectroscopy. Samples were exchanged several times with $D_2O$, dissolved in $D_2O$ and analyzed at 295° K. using a Bruker AM500 spectrometer. Chemical shifts were measured relative to the HOD resonance, which, in turn, was measured relative to sodium 3-trimethylsilylpropionate-2,2,3,3-$d_4$ (TSP).

High Resolution Mass Spectrometry. Fast atom bombardment mass spectrometry (FAB-MS) was performed using a VG ZAB-SE instrument (VG Analytical, Manchester, UK) using an ion-Tech xenon gun operated at 8 kV and 1 Ma in the positive mode or negative ion mode. Samples, 2–10 μg, were analyzed using thioglycerol as the matrix. Liquid secondary ion mass spectrometry (LSIMS) was performed using a JEOL HX110/HX110 mass spectrometer operated in the positive ion mode at 10 kV accelerating potential with a cesium iodide source. Samples were run in a thioglycerol matrix. Acquired spectra are averaged profile data as recorded by a JEOL complement data system. These spectra were acquired from m/z 0–3000 at a rate that would scan from m/z 1 to 6000 in 1 minute. A filtering rate of 300 Hz and an approximate resolution of 1500 were used in acquiring these spectra. Electrospray mass spectrometry (ES-MS), was performed using a SCIEX API-III mass analyzer operated in the positive ion mode with an orifice potential of 50 V. Spectra are the accumulation of 10 to 15 scans collected from 200–1200 a.m.u. with an incremental step of 1.0 a.m.u. Samples were dissolved in 20% aqueous acetonitrile containing 1% acetic acid and pumped into the mass spectrometer at a rate of 3 mL/min.

Composition Analysis. The *R. leguminosarum* bv phaseoli CE3 lipid A was measured for the presence of phosphate with negative results. Unlike the lipid A from enteric bacteria, this Rhizobium lipid A does not contain phosphate. Analysis of the TMS methylglycosyides revealed the presence of galacturonic acid (GalA), glucosamine (GlcN), and an (initially) unidentified component which eluted from the column 2 min prior to glucosamine. The galacturonic acid and glucosamine were present in a 1.00:0.79 ratio as measured from the uncorrected total ion current (TIC) peak areas.

The presence of galacturonic acid was confirmed by mild methanolysis, reduction of the carboxymethyl ester using $NaBD_4$, preparation of alditol acetates and analysis by GLC-MS. The GLC-MS analysis showed the presence of the alditol acetate of galactose having two deuterium atoms at C-6 (fragment ions m/z 219, 291, and 363) thereby proving the presence of galacturonic acid in the lipid A sample.

Figure 5A:
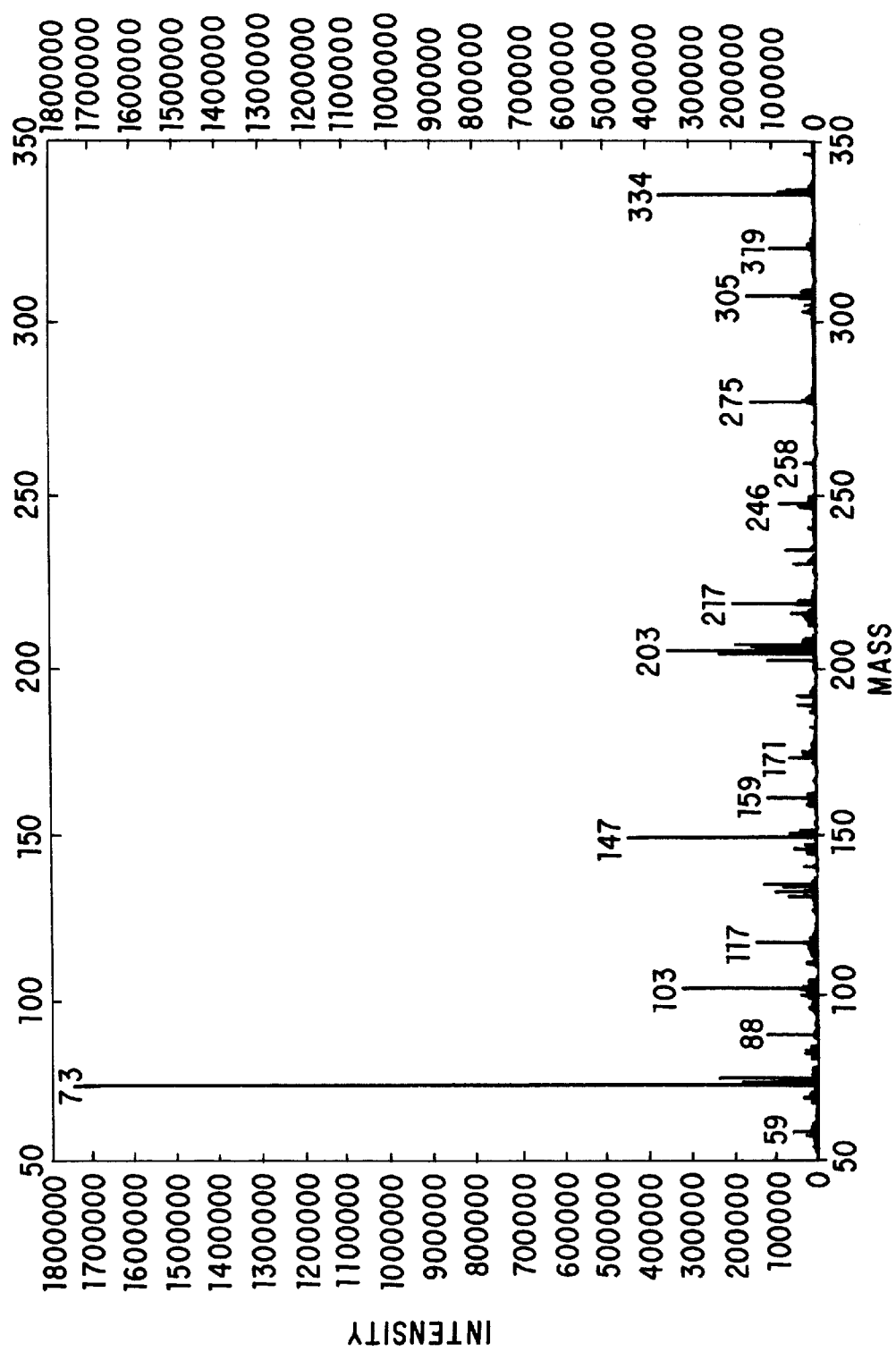
FIG. 5 shows the e.i.-m.s. (panel A) and c.i.-m.s. (panel B) spectra of the N-acetylated TMS derivative of methyl 2-aminogluconate from *R. leguminosarum* bv. phaseoli CE3 lipid A.
Figure 5B:
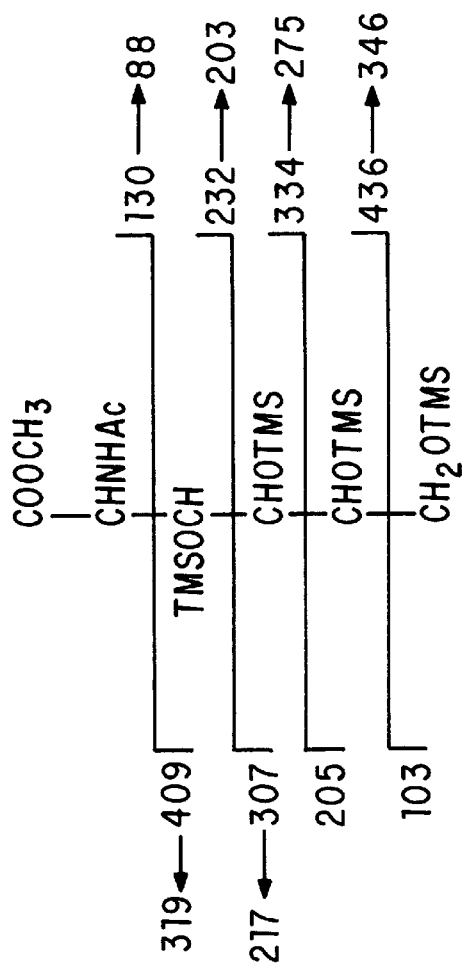
Figure 5C:
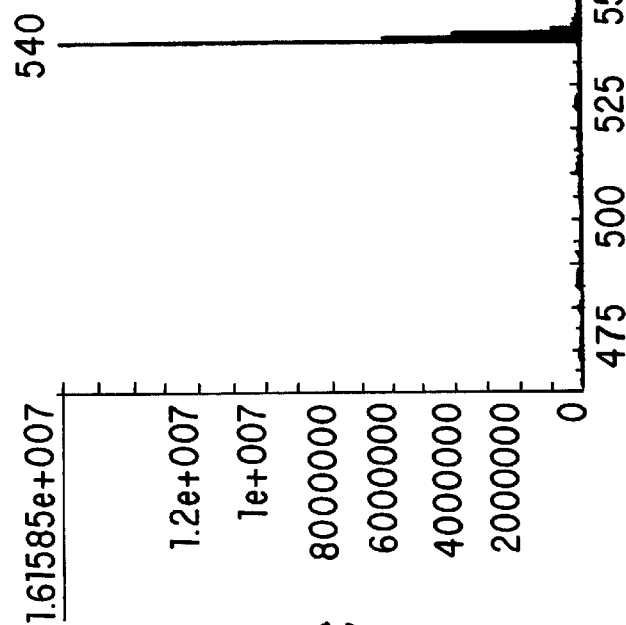

As described above, TMS methyl glycoside analysis revealed an unidentified component eluting 2 min prior to glucosamine. GLC-MS (CI) analysis of this TMS and N-acetylated TMS derivatives resulted in the mass spectra shown in FIGS. 4 and 5, respectively. Both the electron-impact (e.i.) and chemical ionization (c.i.) mass spectra of the TMS derivatives with and without N-acetylation are consistent with this component being the TMS methyl ester of 2-aminogluconic acid (GlcN-onic acid). These data were identical to those obtained from authentic 2-aminogluconic acid (Sigma Chemical Co., St. Louis, Mo.) Additionally, when the sample was subjected to mild methanolysis (methanolic 0.5 M HCl, 2 h at 80° C.), reduction of the carboxymethyl group using $NaBD_4$, hydrolysis (2 M trifluoroacetic acid (TFA), 1 h at 100° C.) and preparation of alditol acetates, the presence of the alditol acetate of glucosamine was found as expected. The mass spectrum of the resulting glucosaminitol alditol acetate gave ions at m/z 145 and 85, and 146 and 86. The former ions (i.e., m/z 145 and 85) result from one deuterium atom at C-1 indicating that the molecule giving rise to these ions is derived from glucosamine. The latter ions at m/z 146 and 86 result from two deuterium ions at C-1 indicating that this second molecule is derived from 2-aminogluconic acid. The relative intensities of the m/z 146 and 145 ions suggested that the glucosamine:2-aminogluconate ratio was 1:1. Subsequently, this ratio was verified by GLC-MS analysis using authentic glucosamine and 2-aminogluconate to obtain accurate response factors.

Fatty acid analysis of the lipid A revealed the presence of β-hydroxymyristate, β-hydroxypalmitate, β-hydroxystearate, β-hydroxypentadecanoate, and 27-hydroxyoctacosanoate (3-OH-$C_{14:O}$, 3-OH-$C_{15:O}$, 3-OH-$C_{16:O}$, 3-OH-$C_{18:O}$ and 27-OH-$C_{28:O}$, respectively). These fatty acids have been individually reported in this lipid A (5,8), as well as the lipid A from other *R. leguminosarum* strains (5). The composition of the lipid A is given in Table I. On a molar basis, a total of five fatty acid chains were present per mole of glucosamine. However, this number of fatty acyl residues is somewhat low since the methanolysis procedure used does not release the N-linked fatty acids quantitatively.

TABLE I

| Comparison of *R. leguminosarum* lipid A. | |
|---|---|
| Component[a] | Mole Ratio |
| galacturonic acid | 1.21 |
| glucosamine | 1.00 |
| 2-aminogluconate | 0.92 |

TABLE I-continued

| Comparison of *R. leguminosarum* lipid A. | |
|---|---|
| Component[a] | Mole Ratio |
| 3-OH-$C_{14:O}$ | 2.22 |
| 3-OH-$C_{15:O}$ | 0.17 |
| 3-OH-$C_{16:O}$ | 0.94 |
| 3-OH-$C_{18:O}$ | 0.51 |
| 27-OH-$C_{28:O}$ | 0.82 |

[a]Most lipid A preparations contained trace amounts of O-antigen and core region carbohydrates, including 3-O-methyl rhamnose, fucose, mannose and 2-keto-3-deoxy-octulosonic acid (Kdo). These trace components, as well as a small percentage of the galacturonic acid originating from the core region, could be removed from the lipid A preparations by extensive washing of the lipid A precipitate with water, followed by centrifugation.

Comparison of the total fatty acids, with those found after removal of the ester-linked fatty acids showed that β-hydroxypalmitate and β-hydroxystearate are exclusively amide-linked, while β-hydroxymyristate is both amide- and ester-linked, and β-hydroxypentadecanoate and 27-hydroxyoctacosanoate are exclusively ester-linked although the 27-hydroxyoctacosanoate group is strongly believed to be located at O-5 of the 2-aminogluconate residue. However, the 27-hydroxyoctacosanoate group may also be at the O-3 or O-4 position of the 2-aminogluconate residue or at the O-3 position of the glucosamine residue. Nonetheless, there is only one 27-hydroxyoctacosanoate group on any single lipid A analog of the present invention.

In addition to removal of the ester-linked fatty acids, methoxide treatment of β-hydroxy acyloxyacyl substituents results in the production of unsaturated fatty acids due to β-elimination (40). While this was observed for the lipid A from Salmonella (analyzed as a positive control), no such unsaturated fatty acids were produced from this Rhizobium lipid A. Thus, Rhizobium lipid A does not contain an acyloxy substituent that is esterified to a β-hydroxy fatty acid. The amide-linked fatty acids were also identified by mild methanolysis, trimethylsilylation and analysis by GC-MS. This procedure releases all ester-linked fatty acids, and cleaves the glycoside bonds, but does not release the amide-linked fatty acyl residues (4). This procedure resulted in the TMS methyl glycosides of three types of N-acylglucosamine residues; β-hydroxymyristyl-glucosamine, β-hydroxypalmitylglucosamine, and β-hydroxystearylglucosamine. This result demonstrates that this Rhizobium lipid A (as currently purified) is heterogeneous (or microheterogenous) with regard to the amide-linked fatty acyl residues. This is unlike the lipid A from enteric bacteria in which β-hydroxymyristate is the only amide-linked fatty acid.

Figure 6D:
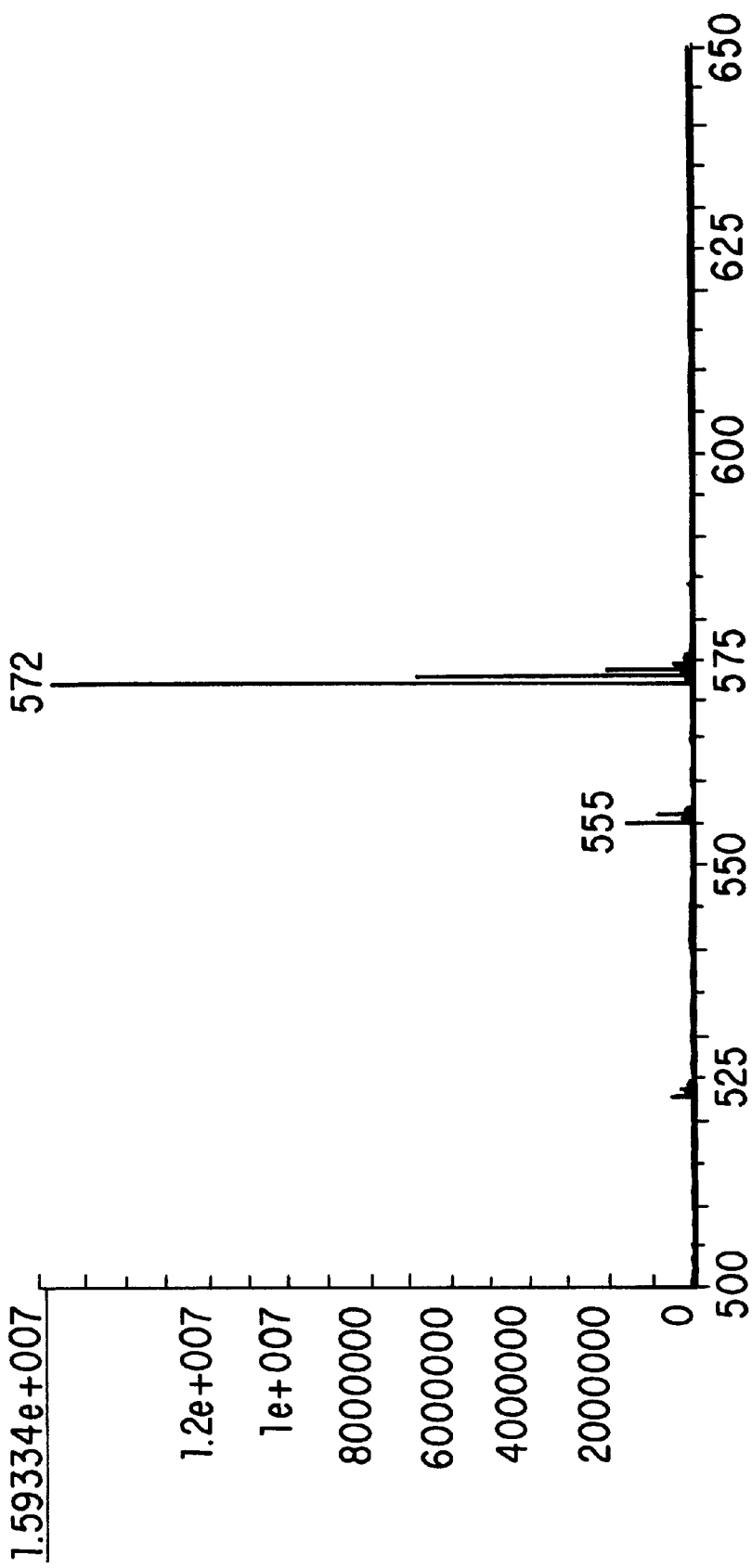
FIG. 6 shows the e.i.-m.s. (top) and c.i.-m.s. (bottom) spectra of the acyloxyacyl methyl ester released from *R. leguminosarum* bv. phaseoli CE3 lipid A by Kraska methylation.

The Kraska methylation procedure was used to identify any amide-linked acyloxyacyl residues. This procedure resulted on only one acyloxyacyl residue; 27-(β-hydroxybutoxy)-octacosanoic acid. The electron-impact mass spectrum of the methyl ester of this residue is shown in FIG. 6. Since previous results suggested that 27-hydroxyoctacosanoic acid was ester linked, this result suggests that this long chain fatty ester is cleaved by Kraska methylation.

Glycosyl Linkage Analysis. Permethylation, reduction of the carboxymethyl group of galacturonic acid, and preparation of alditol acetates resulted in a 1:1 ratio of terminally linked galacturonic acid and 4-O-substituted glucosamine. A partially methylated alditol acetate derivative of 2-aminogluconic acid was not observed. It is thought that this residue is labile and degraded during the methylation procedure. That the galacturonic acid was linked to O-4 of the glucosamine was verified by permethylation, β-elimination, and ethylation with conversion to alditol acetates. The partially methylated, ethylated alditol acetates were prepared and analyzed by GC-MS. A partially methylated, ethylated alditol acetate of glucosamine was observed in which the ethyl group was located at C-4; the mass spectrum showed primary fragments of m/z 217, 203, 175 and 159. Thus, the terminal galacturonosyl residue was linked to O-4 of the glucosaminosyl residue in the lipid A carbohydrate backbone.

Figure 14A:
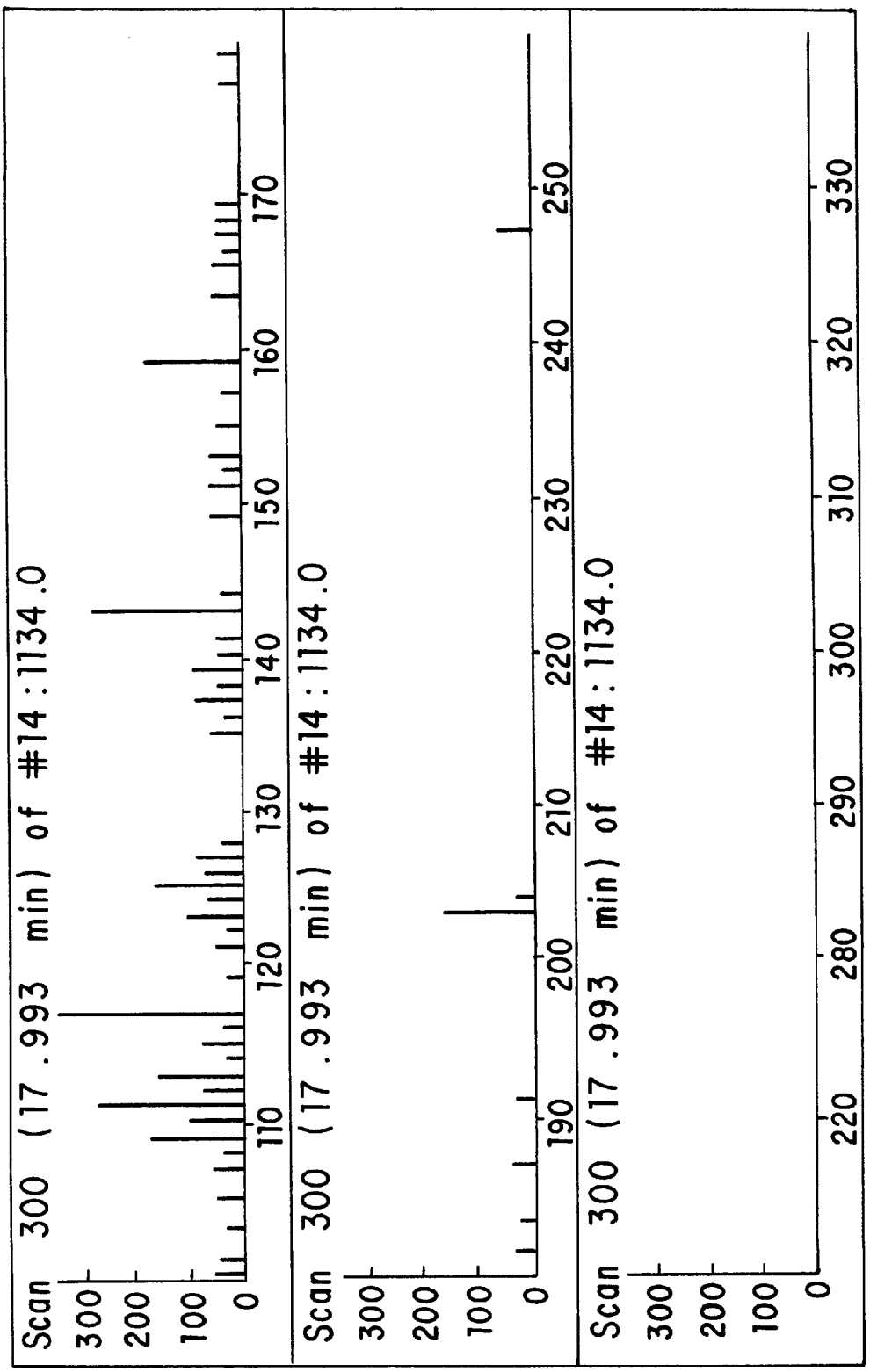
FIG. 14 shows the mass spectrum of the partially methylated/ethylated alditol acetate of the lipid A glucosamine residue after beta-elimination of the galacturonosyl residue from the permethylated lipid A of *R. leguminosarum* bv. phaseoli CE3 (A), or the LPS from strain CE309 (B), and after mild acid hydrolysis of the permethylated LPS from strain CE309 (C).
Figure 14B:
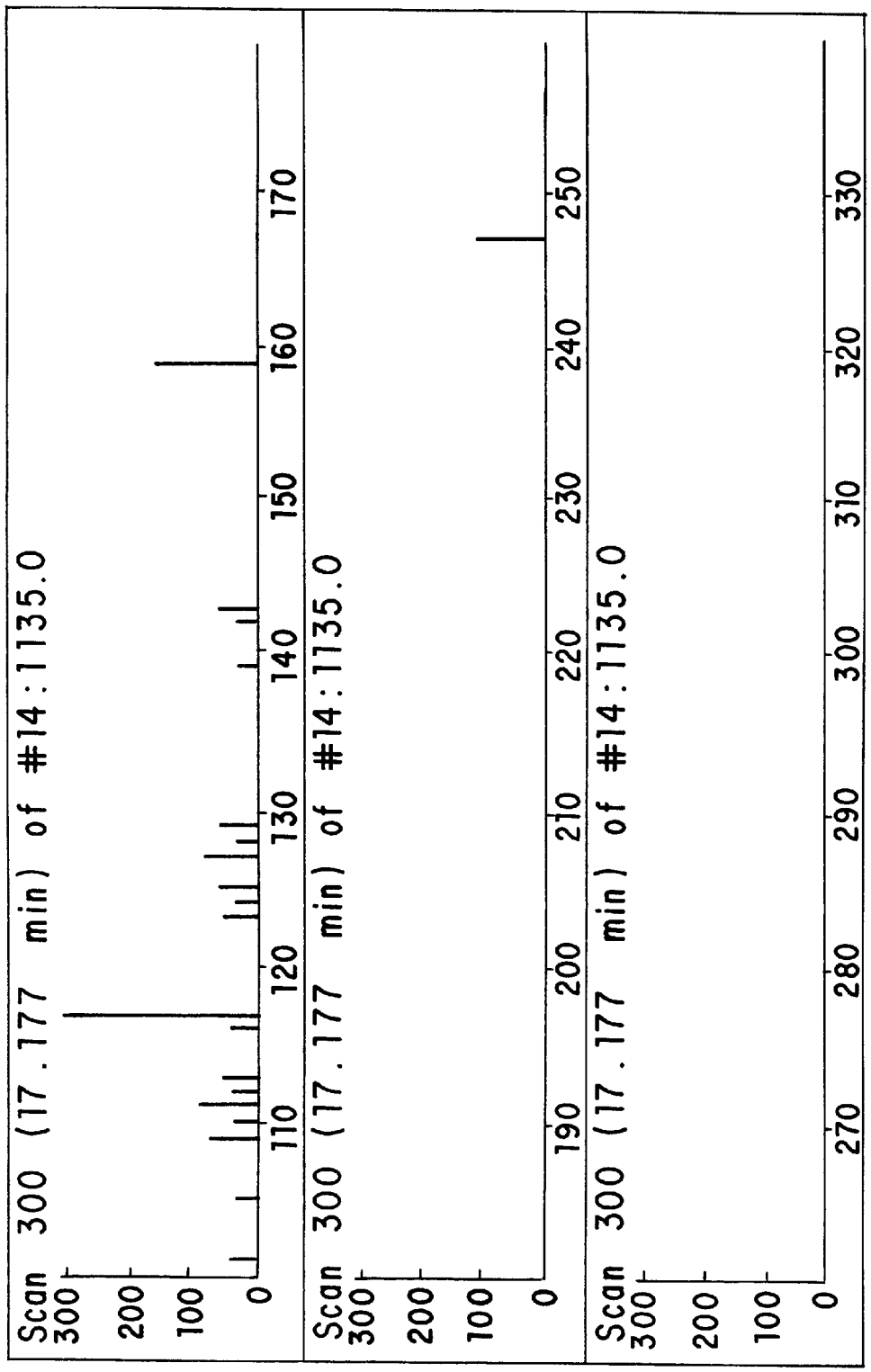
Figure 15C:
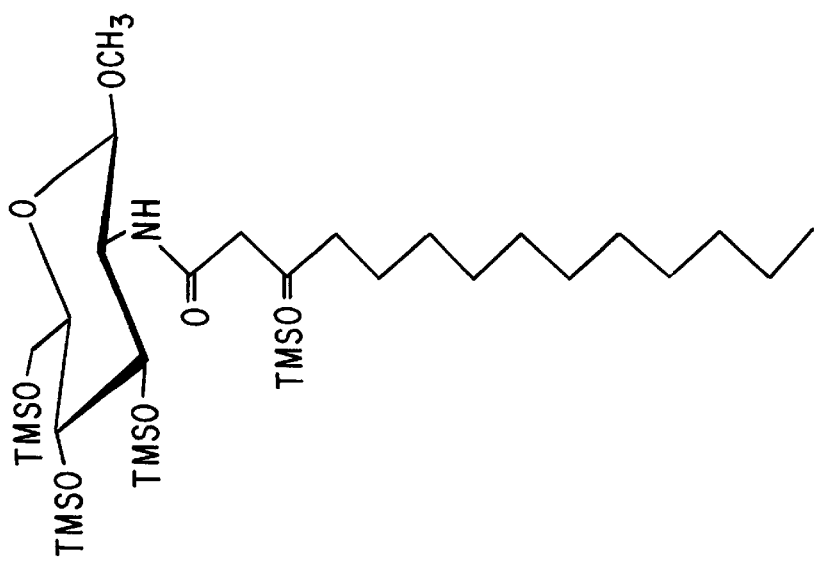
FIG. 15 shows the CI and EI mass spectra of the N-acyl TMS methyl glycosides from *R. leguminosarum* bv. phaseoli CE3 lipid A. (A, GN-3-$OH_{14:O}$; B, GN-3-$OH_{16:O}$; C, GN-3-$OH_{18:O}$)
Figure 15A:
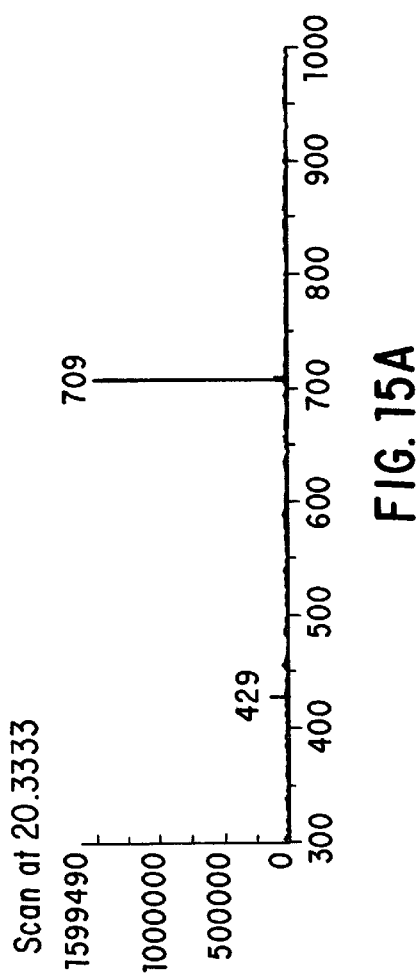
Figure 15B:
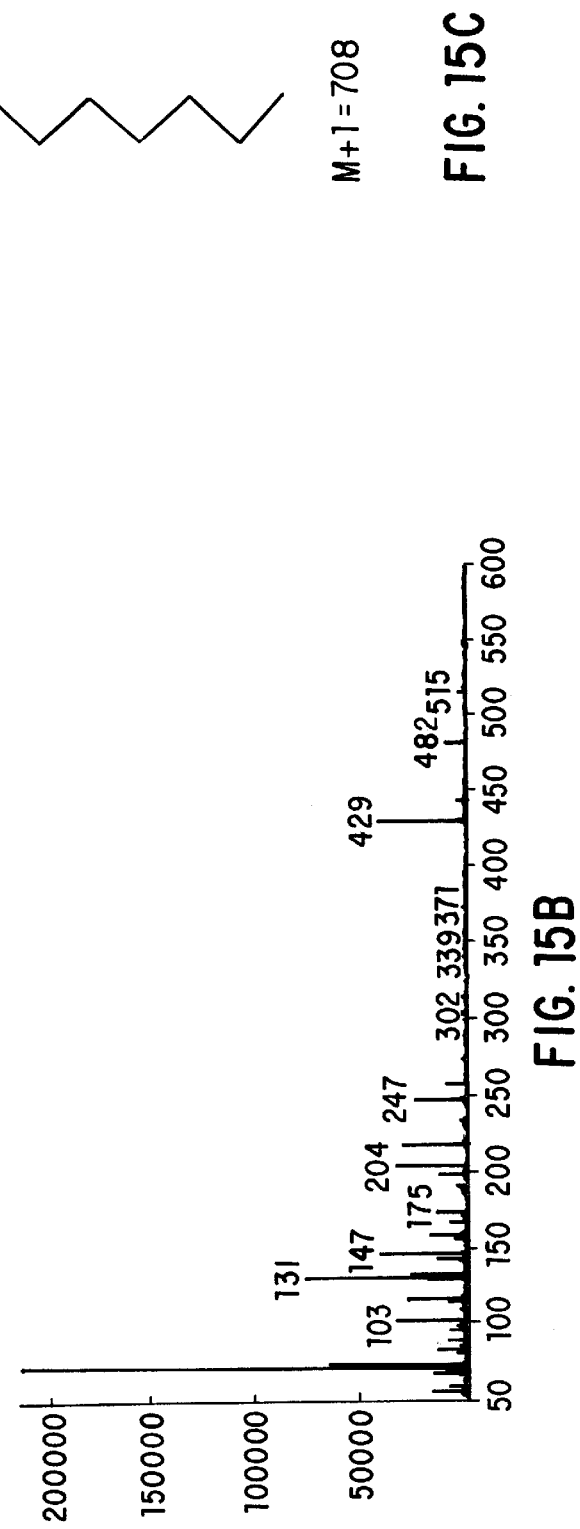
Figure 15I:
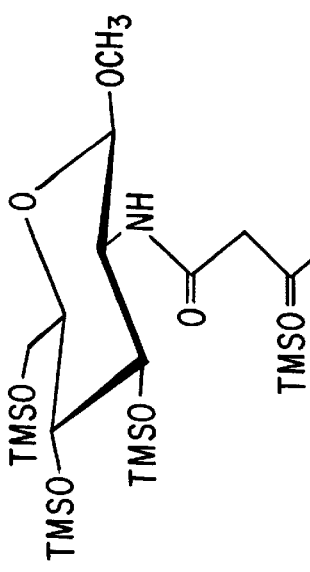
Figure 15G:
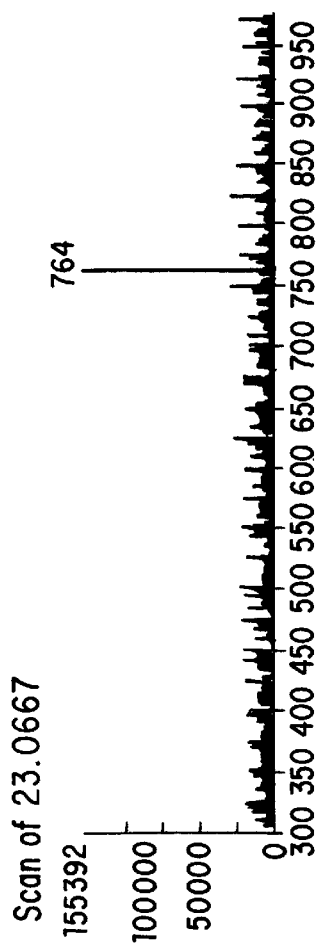
Figure 15H:
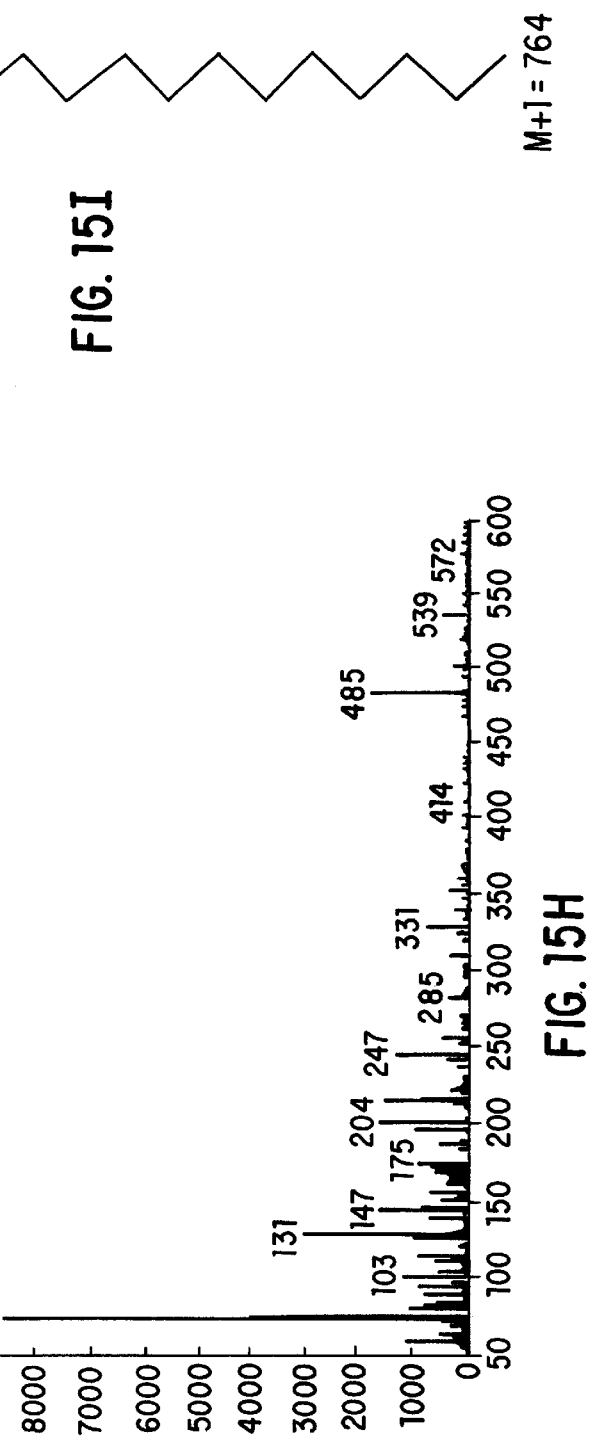

The site of attachment of the core oligosaccharide to the lipid A backbone was determined by methylation analysis of the intact LPS from a mutant of CE3, strain CE309. This mutant produces LPS which lacks the O-chain polysaccharide and has an altered core oligosaccharide (47). Methylation of this LPS showed that glucosamine was present as a 4,6-di-O-substituted residue (data not shown). Permethylation, followed by β-elimination, ethylation and alditol acetate derivatization resulted in N-acetyl-N-methyl-1,5,6-tri-O-acetyl-3-O-methyl-4-O-ethylglucosaminitol. The presence of a single ethyl group at O-4 of this derivative again indicates that the galacturonosyl residue was "β-eliminated" from O-4 of the 4,6-linked glucosamine, suggesting that the core oligosaccharide must be linked to O-6 of this glucosaminosyl residue. The linkage of the core oligosaccharide to lipid A at this position was verified by ethylation of the permethylated, carboxymethyl reduced LPS after mild acid hydrolysis (0.2 M TFA, 30 min at 70° C.), conditions which selectively cleave the Kdo glycosidic bond. During this procedure, the newly exposed (due to mild acid hydrolysis) hydroxyl group on the lipid A backbone, becomes ethylated. Preparation and analysis of the partially methylated, ethylated alditol acetates resulted in N-acetyl-N-methyl-1,4,5-tri-O-acetyl-3-O-methyl-6-O-ethylglucosaminitol, FIG. 14B. The presence of the ethyl group at O-6 showed that this position had been occupied by a mild acid-labile group, presumably the Kdo residue of the core oligosaccharide, in the intact LPS.

The fatty acid substitution of the lipid A sugar backbone was determined by silica-catalyzed methylation (46) under neutral conditions, followed by carboxyl group reduction, and conversion to the alditol acetates. This procedure allows methylation of all hydroxyl groups that are not blocked by a fatty acyl or glycosyl residue. The resulting glucosamine derivative was methylated only at O-6, indicating that this residue was substituted at O-3 by a fatty acid ester. Numerous methylated derivatives of the galacturonosyl residue were also observed, presumably due to undermethylation. Derivatives with a methyl group at all possible locations (i.e. at O-2, O-3, and/or O-4) were present indicating that the galacturonosyl residue is not acylated.

The amide-linked fatty acids in lipid A were investigated by mild methanolysis, trimethylsilylation and analysis by GLC-MS. This procedure releases all ester-linked fatty acids, and cleaves the glycosidic bonds, but does not release the amide-linked fatty acyl residues (4). The TMS methyl glycosides of three types of N-acyl glucosamine residues were observed: N-β-hydroxymyristylglucosamine (GlcN-[3-OH-$C_{14:O}$]), N-β-hydroxypalmitylglucosamine (GlcN-[3-OH-$C_{16:O}$]), and N-β-hydroxystearylglucosamine (GlcN-[3-OH-$C_{18:O}$]) present in a 1.00:0.28:0.07 ratio as determined from the TIC peak areas. These N-acyl glucosamine methyl glycosides were characterized by EI and CI mass spectrometry, and the spectra of the TMS methyl glycosides are shown in FIG. 15. The molecular ions (M+H)$^+$ were m/z 708, 736 and 764, observed for GlcN-[3-OH-$C_{14:O}$], GlcN-[3-OH-$C_{16:O}$], and GlcN-[3-OH-$C_{18:O}$], respectively. In the EI spectra, the characteristic fragment ions involve C-1, C-2 and C-3. The structures and origins of these fragment ions are consistent with those reported for other TMS N-acyl GlcN methyl glycosides (48). The fragment ions involving C-2 and C-3 (i.e. m/z 429, 457 and 485 for GlcN-[3-OH-$C_{14:O}$], GlcN-[3-OH-$C_{16:O}$], and GlcN-[3-OH-$C_{18:O}$], respectively) indicate the nature of the fatty acid substitution at C-2. The expulsion of the acyl ketene ion results in formation of m/z 131. These results indicate that R. leguminosarum bv. phaseoli lipid A is heterogeneous with regard to the glucosamine N-acyl substituents, unlike the lipid A from enteric bacteria in which the only amide-linked fatty acid is 3-OH-$C_{14:O}$.

Kraska methylation was performed in an attempt to identify any amide-linked acyloxyacyl residues. This procedure resulted in only one acyloxyacyl residue; its mass spectrum, FIG. 6, is consistent with 27-O-(β-hydroxybutoxy)-$C_{28:O}$. Analysis by GLC-MS (CI) gave an (M+NH$_4$)$^+$ ion of m/z 572. The EI spectrum shows ions of m/z 59 and 101, which are consistent with a β-hydroxybutyrate substituent at the 27-hydroxy position of the long chain fatty acid. When Kraska methylation was carried out in the presence of trideuteriomethyl iodide these ions shifted to m/z 62 and 104, respectively, also consistent with trideuteriomethylation of a β-hydroxybutyric acid substituent. This acyloxyacyl residue was subjected to complete methanolysis followed by trimethylsilylation of fatty acid methyl esters. Only 27-O-TMS-$C_{28:O}$ was detected, showing that the 27-hydroxy group was not methylated by the Kraska methylation due to its substitution, presumably by β-hydroxybutyric acid. The TMS methyl ester of β-hydroxybutyric acid is very volatile and was not observed, presumably due to its loss during sample preparation. Alkaline cleavage of O-ester linkages, described below, showed that the 27-OH-$C_{28:O}$ is ester linked, not amide linked to the lipid A backbone suggesting that this long chain fatty ester, but not the other ester-linked fatty acids, is cleaved by Kraska methylation.

Figure 16B:
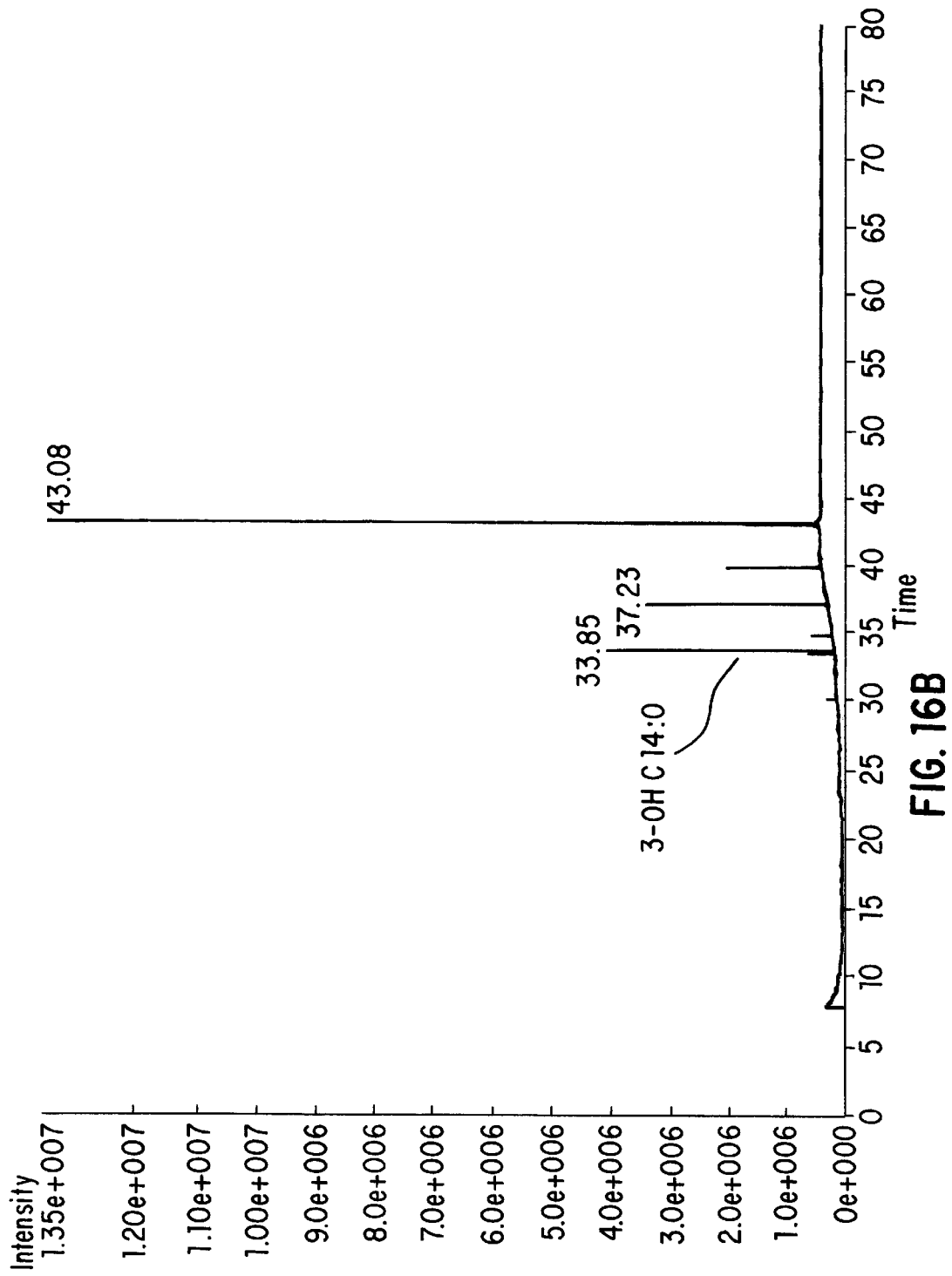
FIG. 16 shows a GLC profile of the fatty acids recovered during de-O-acylation of *R. leguminosarum* bv. phaseoli CE3 lipid A.

De-O-Acylation of Lipid A. De-O-acylation of the lipid A yielded a methanolic supernatant containing released fatty acids and a precipitate consisting of the de-O-esterified lipid A. Analysis of the supernatant by trimethylsilylation and GLC-MS showed that it was devoid of carbohydrate but contained the free fatty acids: 3-OH-$C_{14:O}$, 3-OH-$C_{15:O}$, 3-OH-$C_{16:O}$, 3-OH-$C_{18:O}$, and 27-OH-$C_{28:O}$. Total fatty acid analysis (4 M TFA, 4 h, 100° C.) of the precipitated de-O-acyl lipid A revealed it was composed of only three fatty acids, 3-OH-$C_{14:O}$, 3-OH-$C_{16:O}$, and 3-OH-$C_{18:O}$, and confirms that these are the amide-linked fatty acids in the lipid A molecule. The results further show that a portion of the $^3$-OH-$C_{14:O}$, 3-OH-$C_{16:O}$, and 3-OH-$C_{18:O}$ are also attached as O-esters, while essentially all of the 27-OH-$C_{28:O}$ and 3-OH-$C_{15:O}$ were released by sodium methoxide and are, therefore, exclusively ester-linked. The relative amounts of ester- and amide-linked fatty acids are summarized in Table II, and GLC profiles of the fatty acids recovered during de-O-acylation are shown in FIG. 16. If acyloxyacyl substituents involving β-hydroxy fatty acids were present, methoxide treatment would have resulted in the production of unsaturated fatty acids due to β-elimination (40). While this was observed for the lipid A from Salmonella (analyzed as a positive control), no such unsaturated fatty acids were produced from this Rhizobium lipid A. Thus, Rhizobium lipid A does not contain acyloxyacyl residues involving β-hydroxy fatty acids.

TABLE II

Recovery of Fatty Acids During de-O-acylation

| Component | ester-linked[a] nmole | % | amide linked[b] nmole | % | nmole |
|---|---|---|---|---|---|
| 3-OH-$C_{14:O}$ | 831.8 | 67.6 | 399.2 | 32.4 | 1231.0 |
| 3-OH-$C_{15:O}$ | 106.6 | 100.0 | trace | trace | 106.6 |
| 3-OH-$C_{16:O}$ | 111.1 | 27.0 | 299.7 | 73.0 | 410.8 |
| 3-OH-$C_{18:O}$ | 67.4 | 28.0 | 176.1 | 72.0 | 243.5 |
| 27-OH-$C_{28:O}$ | 436.2 | 100.0 | 0 | 0 | 436.2 |

Figure 17:
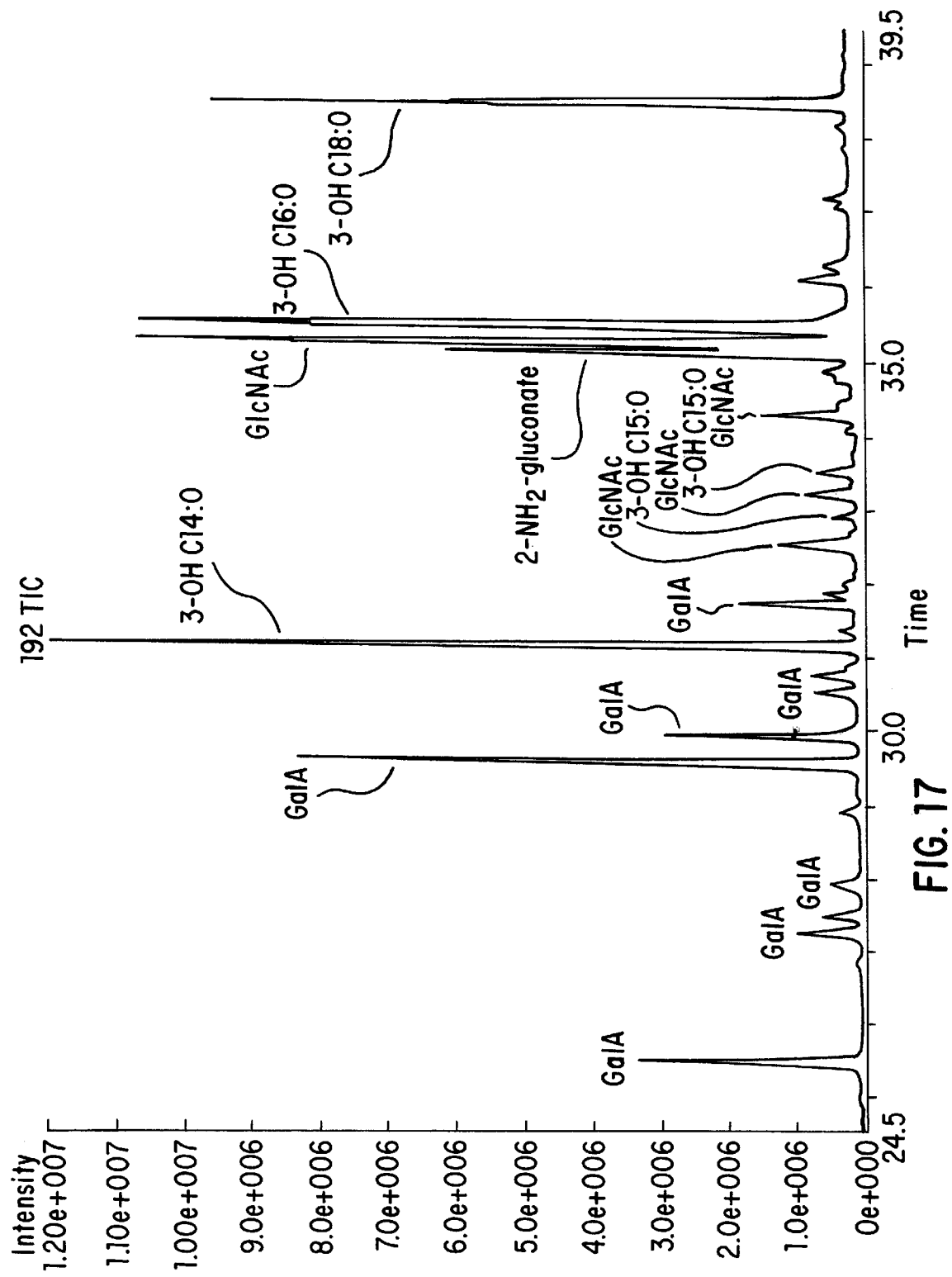
FIG. 17 shows a GLC profile showing the glycosyl and fatty acid composition of the de-O-acylated lipid A from *R. leguminosarum* bv. phaseoli CE3.

[a]fatty acids released from lipid A by 0.5 M sodium methoxide in $CHCl_3$/MeOH
[b]fatty acids released from the de-O-acylated lipid A using 4 M trifluoroacetic acid In a separate analysis, a portion of the de-O-acylated lipid A was subjected to total methanolysis, N-acetylation, and trimethylsilylation with GLC-MS analysis of the resulting derivatives (FIG. 17). In addition to the fatty acids described above, the carbohydrate components were identified as the TMS-methylglycosides of galacturonic acid and N-acetylglucosamine, and the methyl ester of N-acetyl-2-aminogluconic acid. Using response factors measured for authentic standards the calculated mole ratios were 1.00:0.82:0.72, respectively.

Mild methanolysis of the de-O-acyl lipid A followed by trimethylsilylation and GLC-MS analysis confirmed the presence of three N-acylglucosamine derivatives in a ratio consistent with those observed for the intact lipid A: (GlcN-[3-OH-$C_{14:O}$], GlcN-[3-OH-$C_{16:O}$], and GlcN-[3-OH-$C_{18:O}$], 1.00:0.26:0.13). The results confirm the data described above, that the 3-hydroxy 14, 16, and 18 carbon chain fatty acids are amide-linked, and that there is heterogeneity in the amide-linked fatty acids of Rhizobium lipid A.

N-acyl TMS derivatives of 2-aminogluconic acid were not observed, presumably due to the relatively high degree of acid-lability of N-acyl substituents on this compound. A comparison of the rates of methanolysis for authentic N-acetylglucosamine and N-acetyl-2-aminogluconate shows that after 1 hour at 80° C. and 10 percent of the N-acetyl group is cleaved from GlcNAc, whereas essentially 100 percent of the N-acetyl group is removed from N-acetylgluconate.

Analysis of the Hydrazinolysis Product by FAB-MS and NMR. After hydrazinolysis of R. leguminosarum lipid A in anhydrous hydrazine followed by N-acetylation, the resulting product was analyzed by both positive FAB-MS and NMR. Positive FAB-MS shows a molecular ion ((M+H)$^+$) of m/z 655 with a major fragment ion at m/z 436. This fragmentation pattern is consistent with a trisaccharide consisting of an N-acetylated hyrazide of galacturonic acid, an N-acetylated glucosamine residue, and an N-acetylated 2-aminogluconolactone residue. The fragment ion, m/z 436, is due to the N-acetylated GalA(hyrazide)-GlcNAc disaccharide component of this trisaccharide. The data are consistent with the methylation results above which show that the galacturonosyl residue is terminally linked to glucosamine in this lipid A, and that the glucosamine residue is, in turn, linked to 2-aminogluconic acid. The linkage of the 2-aminogluconic acid is under investigation. This residue is particularly labile to methylation procedures. However, it is reasonably certain that the precursor to this lipid A contains 6-linked glucosamine at this position rather than 2-aminogluconate, and that this glucosamine residue is later converted to 2-aminogluconate. Thus, the 2-aminogluconate residue can be linked at C-6. In addition, the linkage also can occur at the C-3 or C-4 position of 2-aminogluconic acid and these embodiments are specifically contemplated herein.

Figure 7:
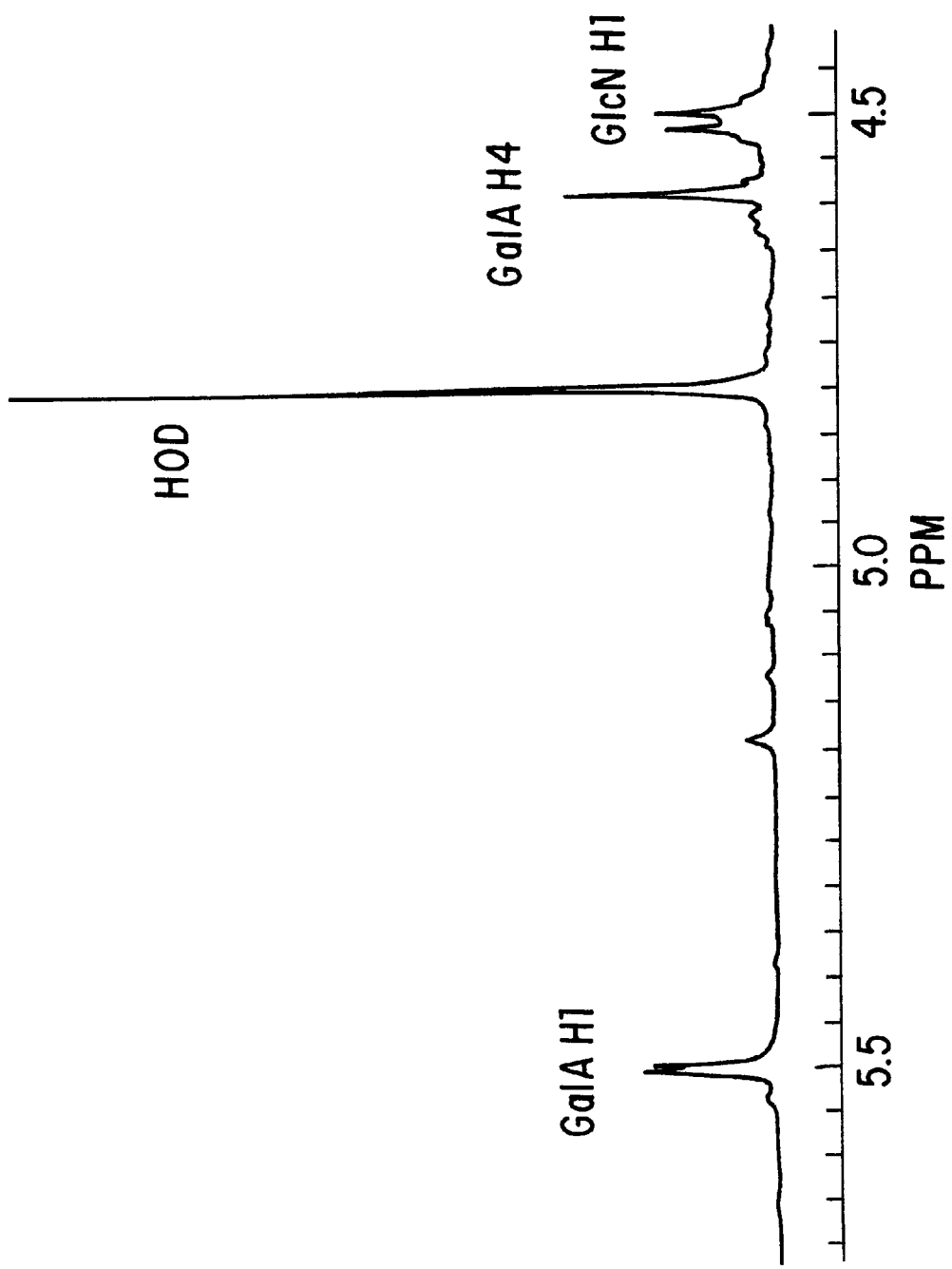
FIG. 7 shows the NMR spectrum, showing the anomeric region, of the N-acetylated hydrazinolysis product of the lipid A from *R. leguminosarum.* GalA H1, the anomeric proton of galacturonic acid; GlcN H1, the anomeric proton of glucosamine.

NMR analysis of the hydrazinolysis product, FIG. 7, shows two anomeric resonances. The resonance at d 5.55 ($J_{12}$=3.4 Hz) is consistent with H-1 of an a-linked galacturonosyl residue. The resonance at d 4.51 ($J_{12}$=8.6 Hz) is consistent with H-1 of a β-linked glucosamine residue. The resonance at about d 4.59 with a small coupling constant can be assigned to the H-4 of the galacturonosyl residue. These results show that the GalA and GlcN residues in this trisaccharide are α- and β-linked, respectively.

Figure 8A:
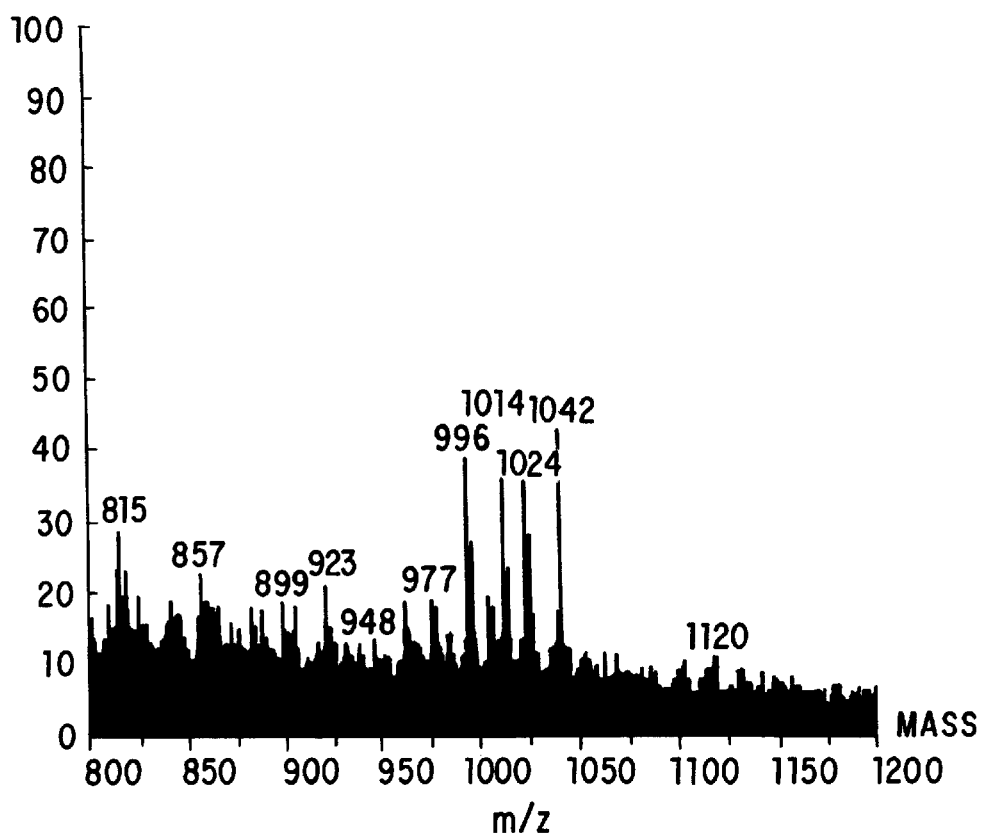
FIG. 8 shows the FAB-MS spectrum (top) of de-O-acylated lipid A from *R. leguminosarum* bv. phaseoli. The bottom panel shows the possible combinations of amide linked fatty acyl substituents that would give rise to the molecular ions observed in the FAB-MS spectrum. Both the acid and lactone forms of the 2-aminogluconate are presumably present in the FAB-MS spectrum.
Figure 8B:
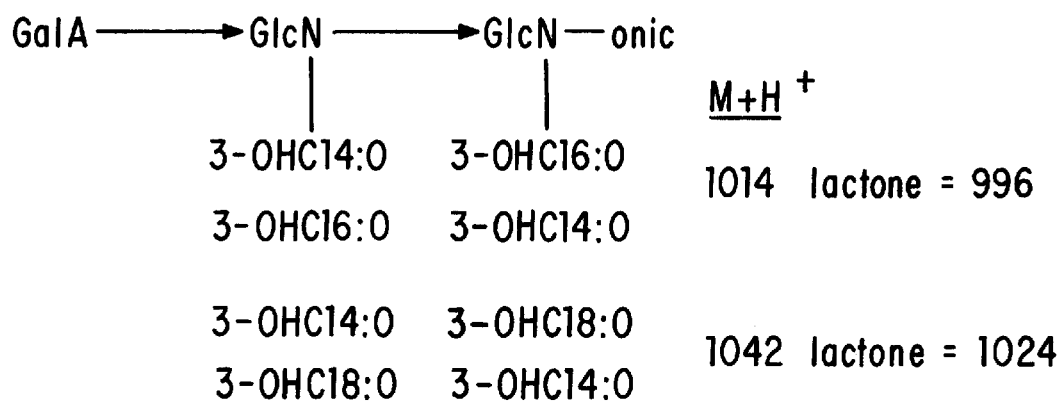

FAB-MS Analysis of De-O-Acylated Lipid A. A portion of the lipid A was de-O-acylated with methoxide (40). Composition analysis of the resulting product shows the presence of galacturonic acid, glucosamine, 2-aminogluconic acid, β-hydroxymyristate, β-hydroxypalmitate, and β-hydroxystearate. The FAB-MS spectrum is shown in FIG. 8. The molecular ions are consistent with the structures shown in FIG. 8. Both acid and lactone versions of the molecule are present. The data also verify the heterogeneity occurring in the N-fatty acyl residues. Two combinations are possible: β-hydroxymyristyl with β-hydroxypalmityl, and β-hydroxymyristyl with β-hydroxystearyl substituents. Since it is known (4) that all three fatty acids can be present on the glucosamine residue, this result implies that there is equal heterogeneity in the acylation of the 2-aminogluconic acid residue.

Figure 1:
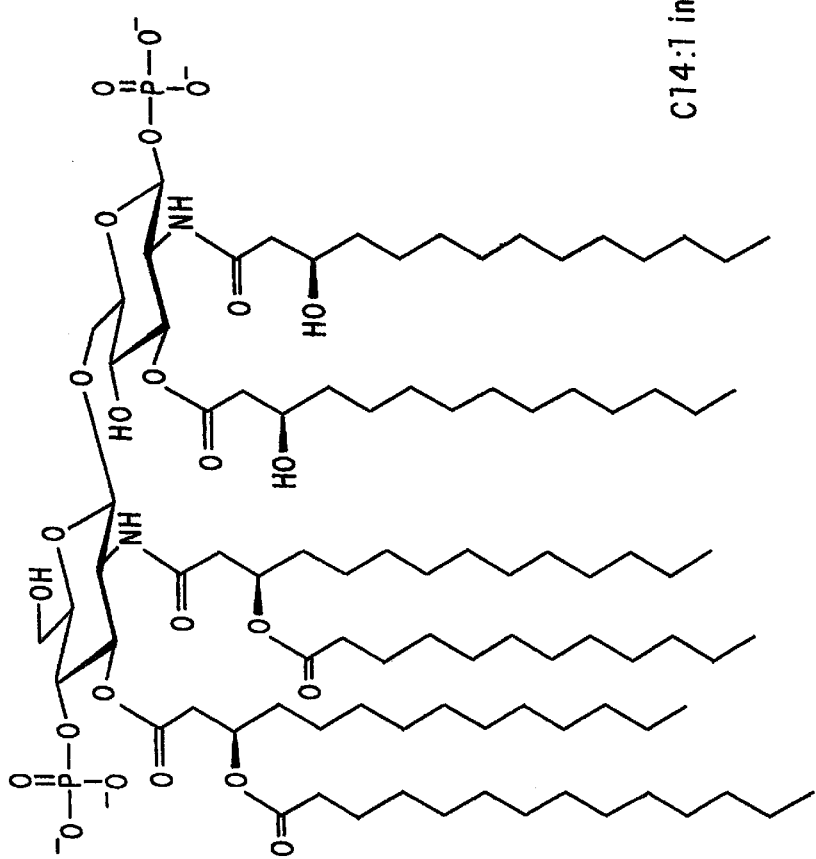
FIG. 1 shows the structure of the lipid A from *E. coli.*
Figure 3:
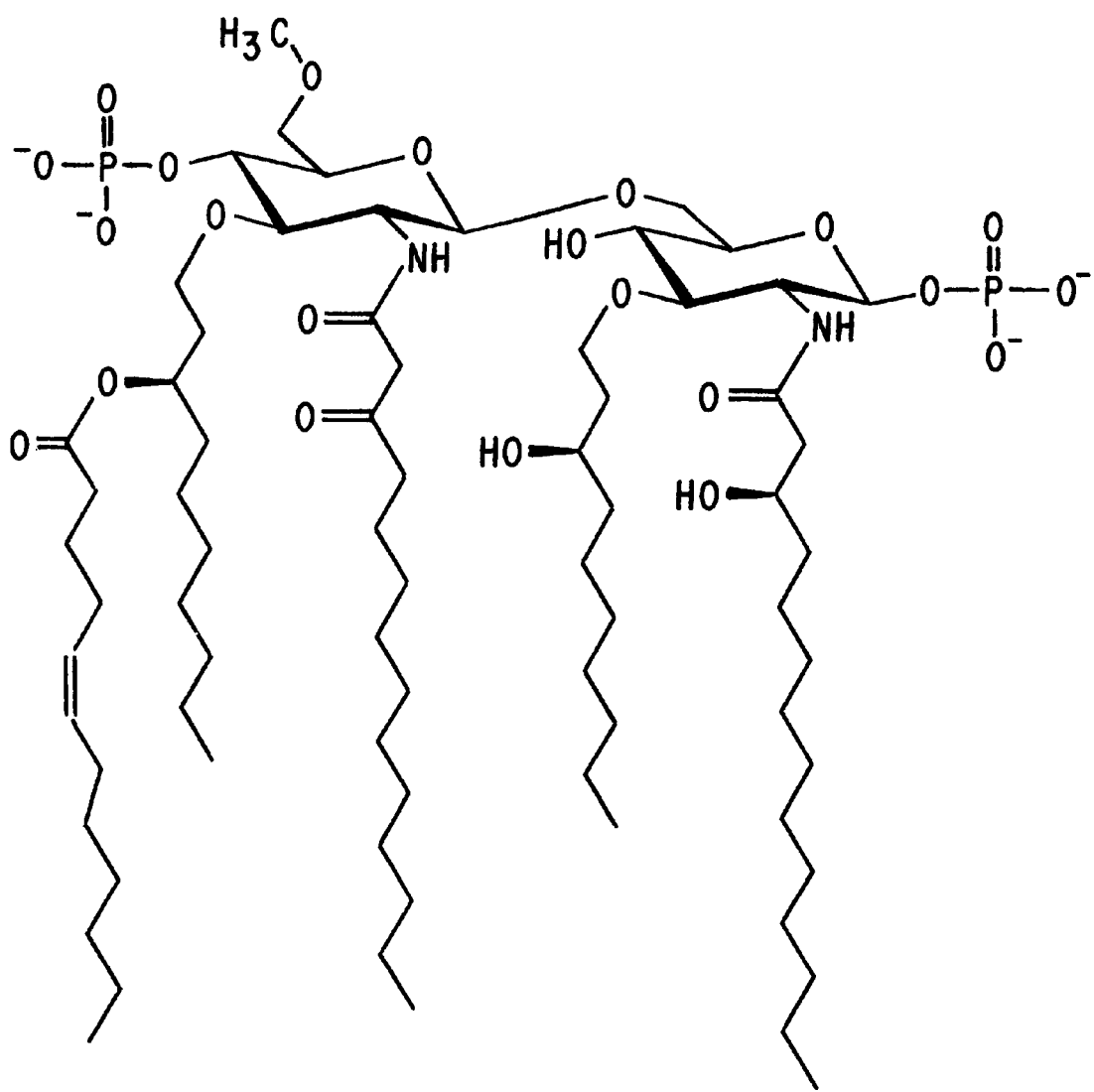
FIG. 3 shows the structure of the lipid A antagonist synthesized by Chris et al., at Eisai.
Figure 4A:
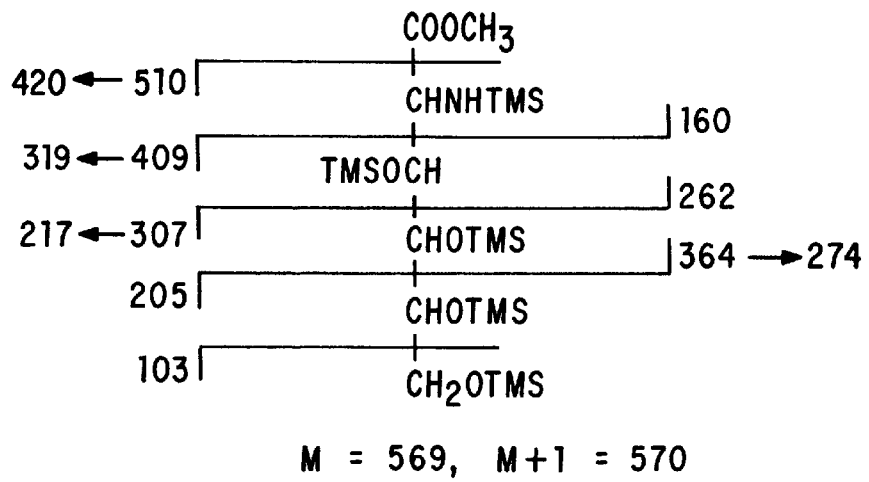
FIG. 4 shows the e.i.-m.s. (panel A) and c.i. m.s. (panel B) spectra of the TMS derivative of methyl 2-aminogluconate from *R. leguminosarum* bv. phaseoli CE3 lipid A.
Figure 4B:
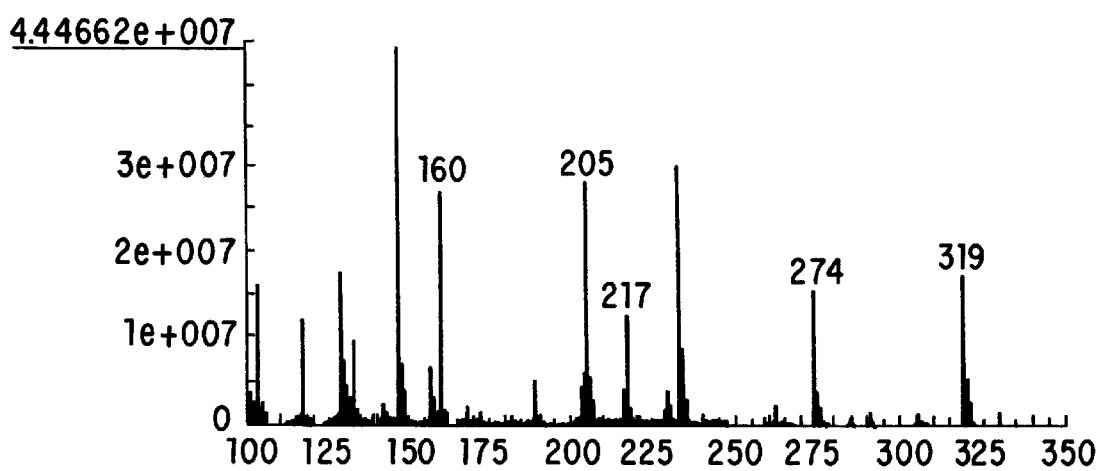
Figure 4C:
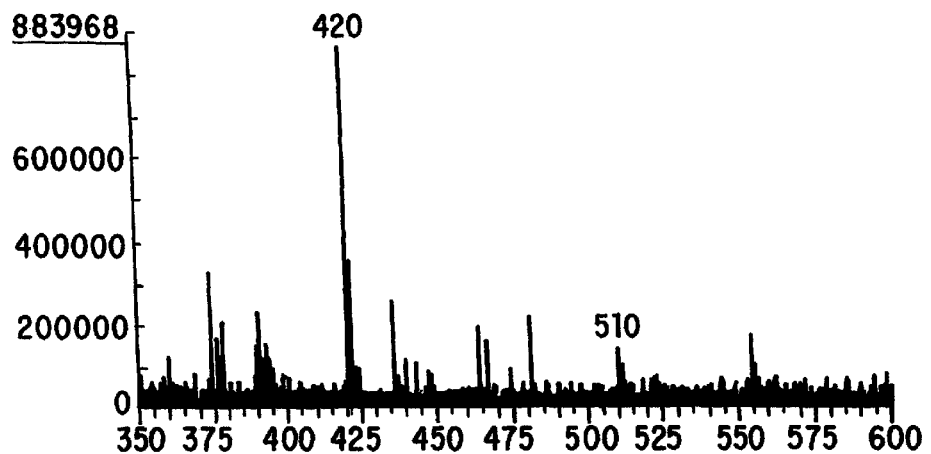
Figure 4D:
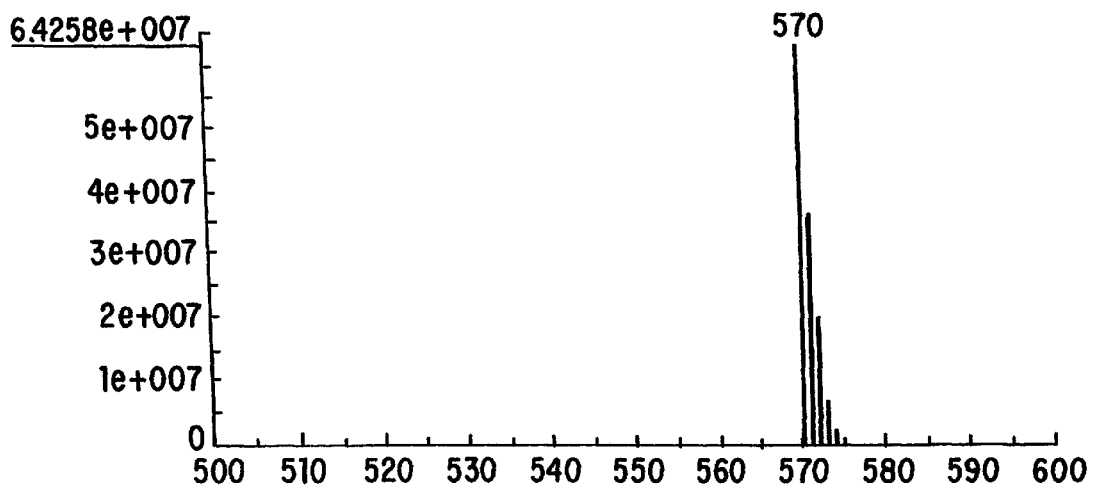

Summary of Structural Analysis. All of the above data support the structures shown in FIG. 9 for the lipid A from R. leguminosarum. For comparison, the structure of E. coli lipid A is shown in FIG. 1. The Rhizobium lipid A differs from that of E. coli in several aspects:

1. There is no phosphate, and a GalA residue, not phosphate, is present at the 4' position of the glucosamine residue.
2. The reducing-end consists of a 2-aminogluconate residue instead of glucosamine.
3. There is heterogeneity in the N-fatty acylation pattern.
4. There are no ester- or amide-linked acyloxyacyl substituents located on any of the β-hydroxy fatty acids.
5. The very long chain fatty acid, 27-hydroxyoctacosanoate, is found in Rhizobium, but not E. coli, lipid A and can contain a β-hydroxybutoxy group as an acyloxy substituent.

FIG. 9B also shows structures that are present due to the lactone versions (GlcN-ono-lactone) of the β-2-aminogluconate residue of this lipid A. These lactone versions are likely formed during the isolation of this lipid A. However, these novel lactone versions, based on their similarity to the natural lipid A, would be expected by one skilled in the art to provoke similar systemic responses in subjects.

Comparison of Rhizobium species. Composition analysis of lipid A from several other strains of R. leguminosarum bv. viciae, trifolii and phaseoli suggests that they may be identical in structure. The lipid A from strains representing all three biovars contains the same fatty acyl residues as those present in the R. leguminosarum bv. phaseoli lipid A described here; however, some quantitative variations are noted (5). Additionally, these lipid As all lack phosphate, and contain galacturonic acid, glucosamine (5) and 2-aminogluconate. It has also been shown that the core oligosaccharides released by mild acid hydrolysis of the LPS from various strains of these three biovars have identical structures (47, 49–51). Thus, it is likely that the core oligosaccharide-lipid A regions of other R. leguminosarum LPSs have a common structure.

The lipid A from R. leguminosarum bv. trifolii ANU843, is reported not to contain glucosamine or phosphate, but consists of 2-aminoglucuronic acid which is N-acylated 27-OH-$C_{28:O}$, and 3-O-acylated with β-hydroxymyristic acid (53). However, composition analysis of the lipid A from *R. leguminosarum* bv. trifolii ANU843 revealed no evidence for this structure. The lipid A from this strain, however, was determined to be identical in structure to that described herein for *R. leguminosarum* bv. phaseoli CE3.

There is a partial explanation for the discrepancies in these data. First, the procedures described in the prior report (53) to determine glycosyl composition may not have released the N-acyl group from the glucosamine residue, and, therefore, may explain the apparent lack of glucosamine. Second, the reported (53) increase in the amount of glucosamine after mild methanolysis and $NaBH_4$ reduction may have been the result of reducing the 2-aminogluconosyl residue, and not due to the presence of 2-aminoglucuronic acid. It is surprising that these workers (53) did not observe galacturonic acid in their lipid A preparation, or their observation that 27-OH-$C_{28:O}$ is amide linked, instead of ester linked.

The second report describes the structure of the lipid A from an *R. trifolii* strain isolated in Poland as consisting of the more common β-1,6-glucosamine disaccharide backbone which is bis-phosphorylated at positions 1 and 4' (52). There is no evidence of such a structure in any of the *R. leguminosarum* strains examined. However, strains isolated from Poland have not yet been examined. Recently, the *R. leguminosarum* bv. phaseoli strain was re-classified (based on 16S RNA homology studies) as *R. etli* (54). Thus, it is possible that the *R. trifolii* strain isolated in Poland represents a different Rhizobium species than the *R. leguminosarum* strains disclosed herein. Homology studies, using 16S RNA, would help clarify the relationship of these *R. leguminosarum* strains to the Polish *R. trifolii* strain.

In the case of the lipid A from enteric bacteria, the phosphate substituents of the 1,4'-bisphosphorylated β-1,6-linked glucosamine disaccharide are crucial for the viability of the bacterium, and, together with the type of fatty acylation pattern, determine the immunostimulatory and toxic properties of the lipid A molecule (31,55). The carboxy groups of the 2-aminogluconic and galacturonic acid residues may functionally substitute for these phosphate groups. In addition to the lack of phosphate, the Rhizobium lipid A of the present invention has an altered fatty acylation pattern when compared with the lipid A from enteric bacteria.

EXAMPLE 2

The Stimulation of IL-1 and IL-6 by *Rhizobium leguminosarum* Lipid A

The Production of Interleukins (IL) 1 and 6. The ability of the novel lipid A discussed herein to stimulate the immune system, i.e. the production of IL-1 and IL-6, was determined with an in vitro assay, using mononuclear cells (MNC). The procedure was performed in the laboratory of Dr. Ernst Rietschel, Forschungsinstitut fur Medizin, Borstel, Germany utilizing procedures previously described (21,22).

Figure 10:
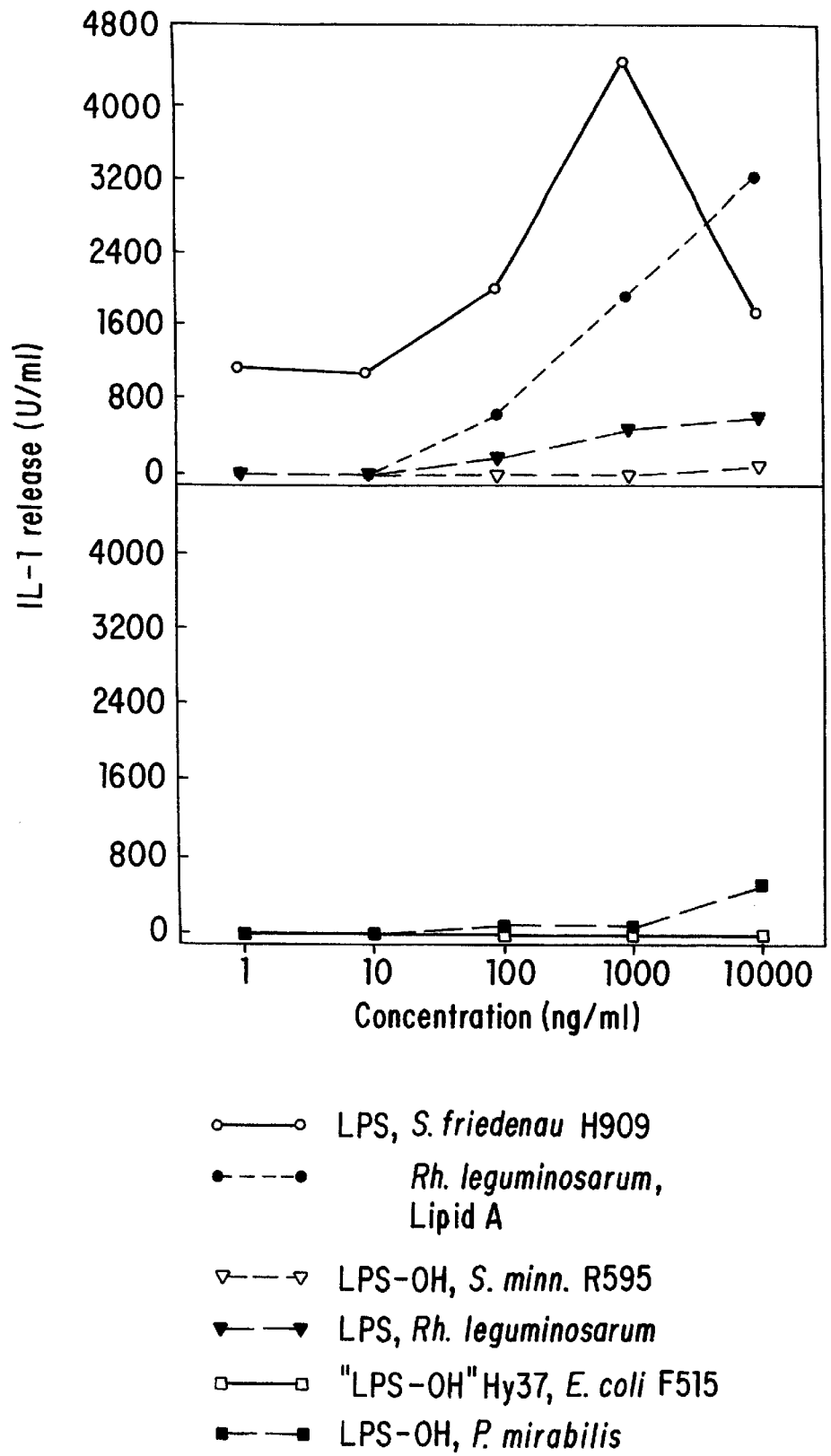
FIG. 10 shows the induction of MNC to produce IL-1 by various lipid A molecules. The LPS-OH samples are de-O-acylated lipid A from the indicated organisms, and are used as negative controls. The *S. friedenau* LPS is a positive control.
Figure 11:
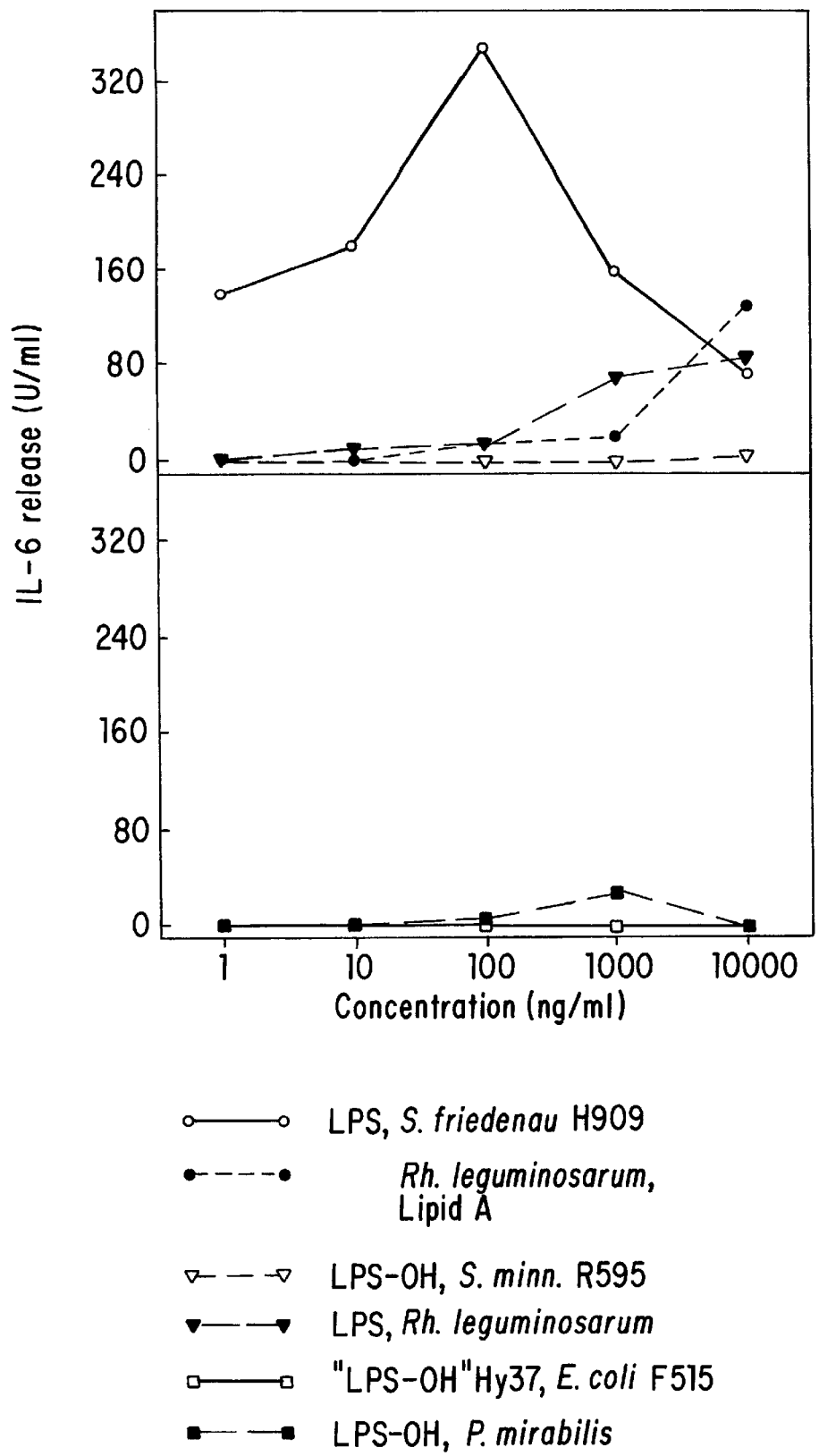
FIG. 11 shows the induction of MNC to produce IL-6 by various lipid A molecules. The lipid A samples are as described for FIG. 10.
Figure 12:
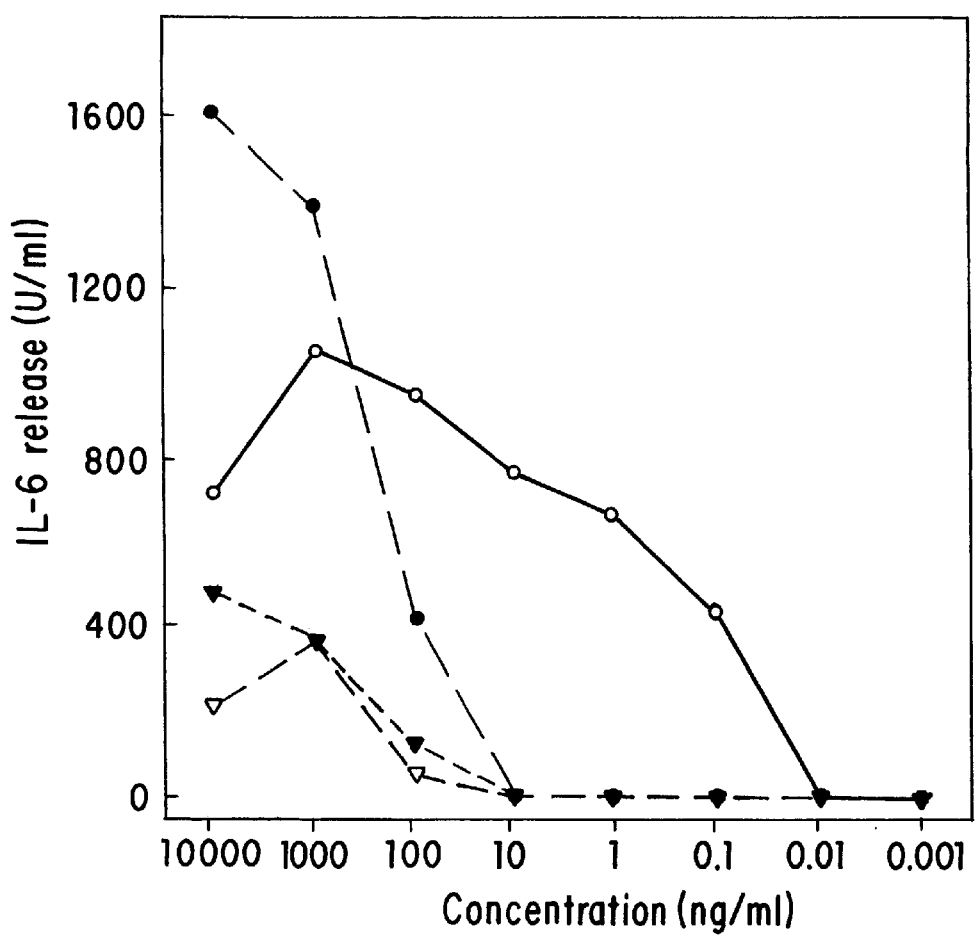
FIG. 12 shows the induction of MNC to produce IL-6 by various lipid A molecules. The concentration range of the various lipid A samples is different from that for FIG. 11. The lipid A samples are as defined in FIG. 10.
Figure 13B:
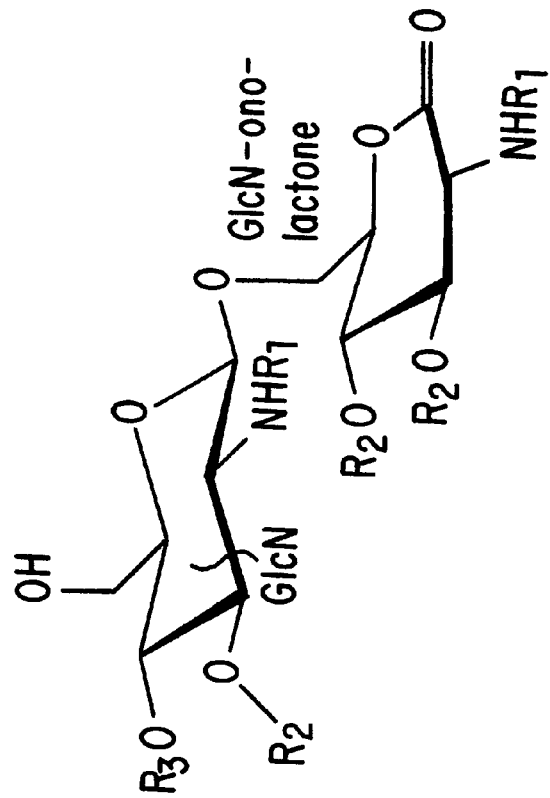
FIG. 13 shows the lipid A structures that are claimed in this patent application. These structures are based on the structures shown in FIG. 10. However, in addition to the structures of *R. leguminosarum* bv. phaseoli CE3 lipid A, other structural variations are also claimed that have different fatty acyl and acyloxyacyl groups than those structures given in FIG. 10. In addition, structures with and without GalA at the 4' position, and with and without phosphate at the 4' position are also shown. These structural variations are potential therapeutic agents based on importance of the type of fatty acyl substituents, and the presence of phosphate for biological activity (described herein).
Figure 13A:
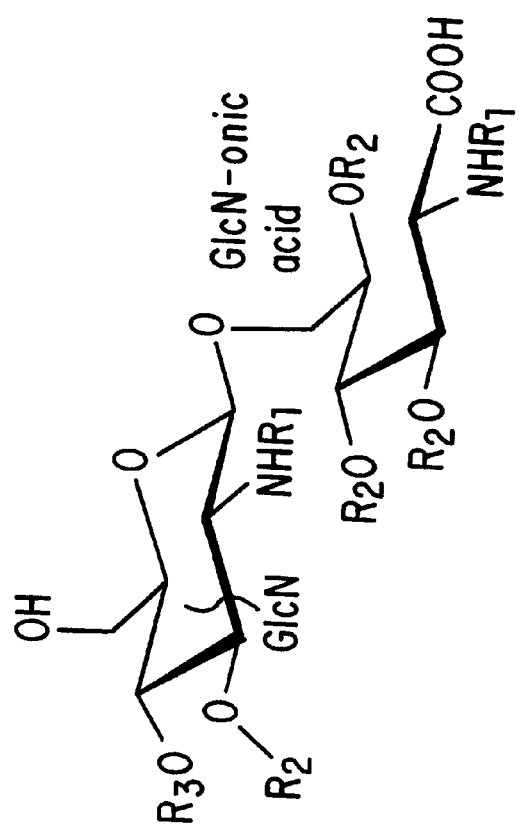
Figure 13C:
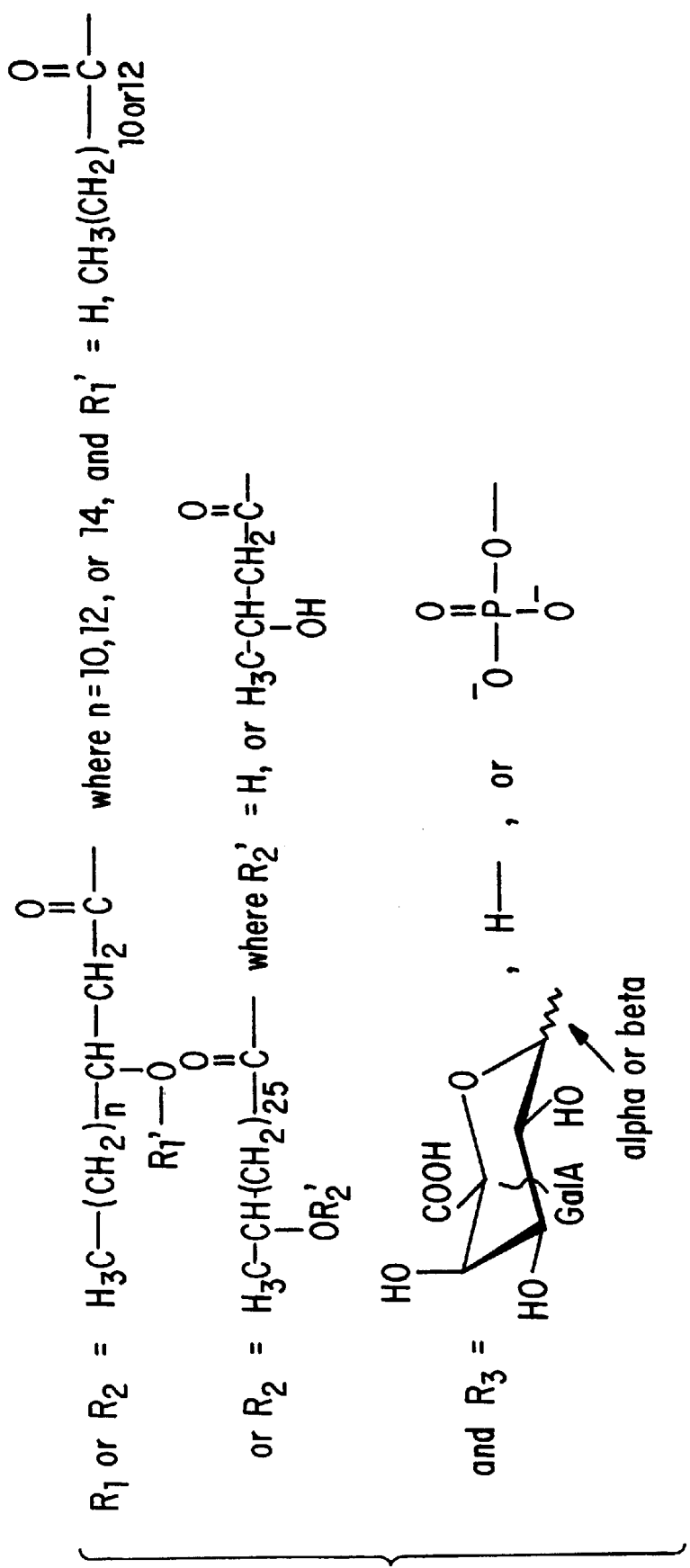

FIG. 10 shows the stimulation of MNC to release IL-1 by *R. leguminosarum* lipid A. The top panel shows that the lipid A, but not the intact LPS, can stimulate the release of IL-1 in the same concentration range as that for the positive control (the LPS from *S. friedenau*), but is less active at low concentrations than the LPS from *S. friedenau*. FIG. 11 shows the stimulation of IL-6 production by *R. leguminosarum* lipid A and LPS. The results are similar to those shown for IL-1 (FIG. 10), except that the level of IL-6 stimulation appears to be much less than that for IL-1. FIG. 12 shows the results of a second experiment examining the stimulation of IL-6. In this experiment the Rhizobium lipid A, in the high concentration range, appears to be as effective as the positive control (the *S. friedenau* LPS). However, unlike the positive control, the stimulation by the Rhizobium lipid A is much more concentration dependent than that from *S. friedenau*, dropping rapidly in activity at dilutions less than 1 mg/mL while *S. friedenau* LPS remained active at concentrations as low as 0.1 ng/mL.

The above experiments show that the Rhizobium lipid A, but not LPS, can stimulate the release of both IL-1 and IL-6 from MNC. The lipid A is more active at stimulating the release of IL-1 than IL-6, and the active concentration of the Rhizobium lipid A is at the higher end of the concentration range when compared with that of the LPS from *S. friedenau*.

FIG. 9 shows that the Rhizobium lipid A varies greatly in structure from that for *E. coli*. These structural variations involve those components that are crucial for the immunostimulatory properties and toxicity of endotoxins; namely, the phosphate and the fatty acyl substituents. It has been well established through the analysis of modified lipid A, and synthetic molecules that the phosphate groups on both the 1 and 4' positions (26,31), the presence acyloxyacyl fatty acids (26,31), and the chain length of the fatty acids (26,31), play important roles in determining the biological activities of these molecules.

The novel, purified lipid A analogs, as well as the heterogeneous mixtures described herein, of the present invention could also be used in methods of enhancing the antigenicity of a vaccine preparation comprising adding to the vaccine preparation a suitable amount of any of the analogs of the novel lipid A or that lipid A itself.

Furthermore, a method is provided for using the LPS or lipid A in a method of stimulating the immune system in a subject comprising administering to the subject an immune system stimulating amount of a purified LPS from *R. leguminosarum* or *R. etli*. In particular, the lipid A of this bacterium has been shown to produce increased amounts of IL-1. In addition, the lipid A of this invention can be used to stimulate the production of increased amounts of IL-1 and IL-6.

Mechanism of Antagonism. Present evidence indicates that endotoxins act via direct interaction with the CD14 cell surface receptor and/or first bind to a serum protein, an LPS binding protein (LBP), and then the LPS-LPB complex is recognized by the CD14 receptor. These interactions trigger a signal transduction cascade that ultimately results in the production of cytokines. The biochemical basis for the transduction steps has not been completely defined. It is thought that an LPS antagonist would act by inhibiting the binding of the LPS to the surface receptor, to LBP, or of an LPS-LBP complex to CD14. However, the phosphate moiety on lipid A is required for maximum toxicity and also results in an optimal three dimensional conformation for binding to the surface receptor or to LBP and/or the lipid A-LBP complex to CD 14. Therefore, the LPSs and Lipid As from the *Rh. etli* and *Rh. leguminosarum* strains would be useful as antagonists for endotoxic activity such as the production of cytokines such as TNF, IL-1 and IL-6.

Treatment of Other LPS Mediated Disorders. Other LPS mediated disorders could be treated with the purified lipid A or LPSs of this invention. For instance, Lyme disease (*Borrelia burgdorferi*) is believed to harbor an LPS (or endotoxin) which is responsible for the autoimmune-like response of the afflicted subject. Other LPS mediated disorders would be readily recognized as treatable by one skilled in the art.

EXAMPLE 3

LPS Purification Procedure

In view of the presently contemplated use of *R. etli* and *R. leguminosarum* LPSs as therapeutic antagonists, e.g., for the treatment of endotoxin induced sepsis or toxic shock and Lyme disease caused by stimulation, inter alia, of TNF, a novel purification process was developed so that large fermenter batches of bacteria could be processed. The process relies on the ability of EDTA and triethylamine (TEA) or triethanolamine (TEolA) to solubilize and disaggregate LPS and on the ability of the antibiotic polymixin B to bind LPS. The new process of extracting LPS is as follows:

Step 1: Extraction of LPS from bacterial pellet. The bacterial pellet is washed in physiologically buffered saline (PBS) to remove soluble medium ingredients and any extracellular polysaccharide that may be adhering to the bacteria. The pellet is then suspended (5 ml/g we weight of bacteria) in a 1:2 to 1:4, preferably a 1:3 ratio, of EDTA-TEA or EDTA-TEolA solution (e.g., 0.33 M EDTA and 1.0 M TEA or TEolA). The ratio should be adjusted such that the pH ranges from 5.5 to 8.5, preferably from 6.5 to 8.0, more preferably 7.0. Thereafter, the suspension is stirred or otherwise agitated for 15 minutes to 2 hours, preferably 1 hour at from 25° C. to 60° C., preferably 30° C. to 50° C., more preferably 37° C. After stirring, the bacteria may be removed (or, alternatively, may be further processed in situ), for example, by centrifugation, and the supernatant is saved. The resulting pellet can be extracted one or more extra times if necessary and the subsequent supernatants combined with the first.

In a preferred embodiment, the EDTA and TEA or TEolA mixture is combined with approximately 5% by volume of liquified phenol and the resulting mixture is incubated at 60° C. for about 15 minutes to 2 hours, preferably about 30 minutes.

Step 2: Purification of the LPS from the extraction supernatant. The above supernatant, or the water layer from a phenol-water extraction is the starting material for this step; however, PAGE analysis of the above supernatant and phenol-water extracted material has shown that the supernatant is less contaminated by extracellular and capsular polysaccharides, and nucleic acids. However, if necessary, the supernatant or phenol-water extract can be incubated with RNase, DNase, and protease prior to application to the Polymixin B-agarose affinity material. Such application preferably occurs at approximately pH 7.0 to 9.0, preferably pH 8.0. The supernatant, or phenol-water extract, is dialyzed against 50 mM $NH_4HCO_3$ at approximately pH 8.0. After dialysis, the solution is optionally centrifuged or filtered to remove any insoluble debris. One of ordinary skill in the art would recognize that there are other ways of removing insoluble debris.

A column of Polymixin B-agarose affinity material (Sigma Chemical Co., St. Louis, Mo.) is prepared and washed with the above $NH_4HCO_3$ solution. Approximately 3–4 mg of LPS can be purified per mL of column bed volume. The LPS-containing solution from above is applied to the column. After application, the column is washed with 2 bed volumes of the $NH_4HCO_3$ solution. If PAGE analysis of the pre-column LPS-containing solutions shows that it contains non-LPS components such as other polysaccharides or nucleic acid, these components may also bind to the column and can be removed by applying higher ionic-strength buffers to the column, followed by washing the column with the 0.05 M $NH_4HCO_3$ solution. This is then followed by elution of the bound LPS in 1% DOC (deoxycholate) in 0.1 M $NH_4HCO_3$. The Polymixin B-agarose affinity material can then be regenerated by washing with the original $NH_4HCO_3$ solution.

In the above process steps, the use of ammonium bicarbonate is preferable, but not mandatory.

Finally, the LPS can be recovered from the DOC by dialysis and freeze-drying. The resulting LPS contains the full spectrum of the various LPSs and LPS components from the sample.

PAGE analysis has confirmed that, by using this process, no LPS was removed from the column until the 1% DOC wash. Moreover, the LPS recovered at the time was free of any non-LPS contaminants.

EXAMPLE 4

LPS Characterization

Lipopolysaccharide is a major component of the bacterial outer membrane, and for Rhizobium spp. has been shown to play a critical role in the establishment of an effective nitrogen-fixing symbiosis with a legume host. Many genes required for O-chain polysaccharide synthesis are in the LPS region of the CE3 genome; this region may also carry LPS genes required for core oligosaccharide synthesis. The LPS can be mutated by standard methods, for example, transposon mutagenesis (24, 75). The LPSs from several strains mutated in the region were isolated, and their mild acid released oligosaccharides, purified by high performance anion-exchange chromatography, were characterized by electrospray- and fast atom bombardment-mass spectrometry, NMR, and methylation analysis. The LPSs from several mutants contained truncated O-chains, and the core region consisted of a (3-deoxy-D-manno-2-octulosomic acid) (Kdo)-(2→6)-α-Galp-(1→6)-[α-GalpA-(1→4)]-α-Manp-(1→5)-Kdop (3-deoxy-D-manno-2-octulosomic acid) (Kdo)pentasaccharide and a α-GalpA-(1→4)-[α-GalpA-(1→5)]-Kdop trisaccharide. The pentasaccharide was altered in two mutants in that it was missing either the terminal Kdo or the GalA residue. These results indicate that the LPS region, in addition to having the genes for O-chain synthesis, contains genes required for the transfer of these 2 residues to the core region. Also, the results show that an LPS with a complete core, but lacking an O-chain polysaccharide is not sufficient for an effective symbiosis.

Background: *Rhizobium etli* (54) and *Rhizobium leguminosarum* are closely related species in the a group of the Proteobacteria (56, 57). The biology of these bacteria has been extensively studied, particularly their nitrogen fixing symbioses with certain legumes, and LPS structure is critical in the development of these symbioses. The LPS structure (58) and genetics (59) of several strains of these species are known in some detail.

Structural regions of the LPS from *R. leguminosarum* and *R. etli* have been defined according to fragments released from purified LPSs by mild acid hydrolysis. The structures of the core oligosaccharides from *R. etli* bv. CE3, and from *R. leguminosarum* bv. trifolii and bv. viciae (58, 60, 49, 50, 47, 51) are:

α-Galp-(1→6)-[α-GalpA-(1→4)]-α-Manp-(1→5)-Kdop    (I)

and

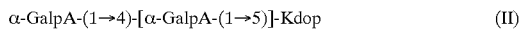
(II)

The lipid A portion of these LPSs has a trisaccharide glycosyl backbone consisting of one each of galacturonosyl (GalA), glucosaminosyl (GlcN), and 2-aminogluconosyl (GlcN-onate) residues; the latter 2 residues being O- and N-acylated with β-hydroxymyristate, -palmitate, -pentadecanoate, -stearate, and 27-hydroxyoctacosanoate (61). Both the lipid A and the core regions are structurally very different from those of the enteric bacteria, in which the lipid A is comprised of an acylated bis-1,4'-phosphorylated β-1,6-glucosamine disaccharide, while the core oligosaccharide usually contains heptose and lacks uronosyl residues. The remaining LPS structural region is the distal O-chain polysaccharide that, when present, is the dominant antigen of the LPS and the bacterial cell. R. leguminosarum and R. etli O-chains, as released by mild hydrolysis, are polysaccharides that contain Kdo at their reducing ends (8, 62). This Kdo may be the outermost core glycosyl residue to which the O-chain is transferred during the biosynthesis of the LPS.

Figure 18:
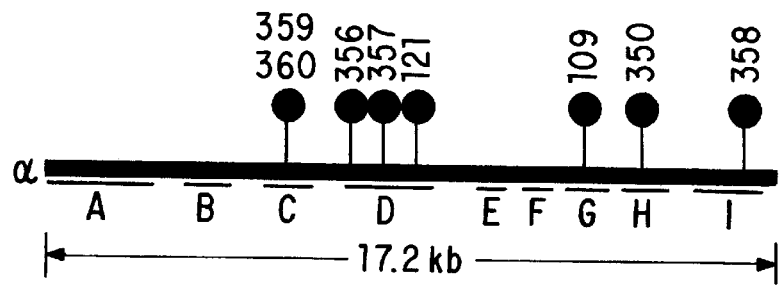
FIG. 18 shows the location of the various mutations in the α region of the *R. etli* CE3 genome. All of the mutants designated by the filled circle either lack or have much less than normal LPS I. The letters refer to complementation groups, presumably representing operons, defined by Tn5 insertion mutagenesis. The distance shown is between the Tn5 insertions at either end of the region.

Synthesis of the core oligosaccharide and O-chain portion of the LPS requires lps genes from at least five regions of the R. etli bv. CE3 genome, as defined by cosmid genetic cloning (59, 63, 64). Most of the genes that have been identified are located in a stretch of the chromosome, termed the lps α region (59), in which nine complementation groups have been identified within 18 kilobases of DNA (65) (FIG. 18). It appears that this region carries genes for synthesis of at least the strain-specific O-chain glycosyl residues and linkages (66) and at least one gene necessary for core oligosaccharide synthesis as well (47, 67).

R. leguminosarum, R. etli, and Bradyrhizobium japonicum mutants that are deficient in the LPS O-chain polysaccharide elicit incomplete infections and root nodule development on their legume hosts (59, 63, 68, 69). Although all LPS mutants that are defective in symbiosis have deficient or altered O-chain-containing LPS, it had not been ruled out in previous studies that these mutants might also be defective in the core oligosaccharides. In fact, the LPSs from two R. etli mutants have truncated core structures (47, 67).

Bacterial Strains: The bacterial strains were grown in TY medium with added calcium as described previously (8). The mutant strains are described in Table III. The mutants were derived from the CE3 (i.e., CFN42) parent of ATCC # 51251 by the transposon mutagenesis method (24, 75).

LPS Isolation: Bacteria were harvested by centrifugation and the pellets extracted using the hot phenol-water extraction procedure as described previously (8, 39). The LPSs were further purified from the aqueous layer, as described previously (8, 39), by digestion with RNase and DNase, followed by extensive dialysis against deionized water using 12,000–14,000 MWC dialysis tubing, and freeze-dried. The LPS from the parent strain, CE3, had also been further purified by gel-filtration chromatography using Sepharose 4B in and EDTA/triethylamine buffer at pH 7 (8, 9). Separation of higher from lower molecular weight forms of LPS was accomplished by gel filtration chromatography on Sephadex G-150 in the presence of deoxycholate (DOC) as described previously (70, 71, 72).

Polyacrylamide Gel Electrophoretic Analysis (PAGE): PAGE analysis was performed using 18% acrylamide gels with DOC as the detergent (73). The gels were silver stained as described (74).

Isolation of Core Oligosaccharides from the LPSs: Each LPS was dissolved in deionized water (10 mg/ml), acetic acid was added to 1%, and the solution heated at 100° C. for 1 h. This procedure hydrolyzes the ketosidic bond between the polysaccharide Kdo residue and the lipid A, which precipitates (29). The lipid A was removed by centrifugation, and the carbohydrate was further purified by HPAEC on a CarboPac™ PA1 column (DIONEX) using a gradient comprised of 1 M NaOAc (A) and 100 mm NaOH (B); 10% A and 90% B for 10 min and then to 50% A and 50% B by 40 min. The various carbohydrate peaks were collected, the acetate was removed by passage through DIONEX OnGuard H cartridges, and the eluants freeze-dried.

Analysis of the Glycosyl Residues: Glycosyl compositions were determined by the preparation and gas liquid chromatographic (GLC)-mass spectrometric (MS) analysis of alditol acetates, or trimethylsilyl methyl glycosides (43), and glycosyl linkages were determined by methylation analysis using the Hakomori procedure as described by York et al. (43). For the isolated core oligosaccharides, it was necessary to reduce the samples with $NaBD_4$ prior to methylation. Also, for certain samples, after methylation, it was necessary to reduce the carboxymethyl groups of the acidic sugars with lithium triethylborodeuteride (Superdeuteride from Aldrich) (43). Alditol acetates of the methylated samples were prepared by hydrolysis, reduction with $NaBD_4$, and acetylation with acetic anhydride in pyridine as described by York et al. (43). Combined GLC-MS was performed using an HP5890-5970 GLC-MSD system equipped with a 30-m SP2330 fused silica column from Supelco for the alditol and partially methylated alditol acetates (PMAAs), or with a 30-m DB-1 column from J& Scientific for trimethylsilyl methyl glycosides.

Mass Spectrometry Analysis: Fast atom bombardment-mass spectrometry (FAB-MS) was performed using a VG ZAB-SE instrument at an accelerating voltage of 8 kV. Approximately 2–10 μg of sample was placed on the probe. Thioglycerol was used as the matrix. Electrospray mass spectrometry (ES-MS) was performed using a SCIEX API-III mass analyzer operated in the positive mode with an orifice of 50 V. Samples were dissolved in 20% aqueous acetonitrile and pumped into the mass spectrometer at a rate of 3 μl/min.

NMR: Samples were exchanged several times with $D_2O$, dissolved in $D_2O$ and analyzed at 295° K. using a Bruker AM500 spectrometer. Chemical shifts were measured relative to the HOD resonance, which, in turn, was measured relative to sodium 3-trimethylsilylpropionate-2,2,3,3-$d_4$.

TABLE III

| | Bacterial strains | |
|---|---|---|
| Strain[a] | Characteristics[b] | Refs. |
| CE3 | str-1, Lps[+], LPS I, Ndv[+], Fix[+] | 79 |
| CE109 | str-1, lps-109::Tn5, LPSIII, Ndv[−] | 63 |
| CE121 | str-1, lps-121::Tn5, LPS IV, Ndv[−] | 63 |
| CE350 | str-1, lps-3::Tn5, LPS III, Ndv[−] | 65 |
| CE356 | str-1, lps-7::Tn5, LPS IV, Ndv[−] | 65 |
| CE357 | str-1, lps-5::Tn5, LPS IV, Ndv[−] | 65 |
| CE358 | str-1, lps-2::Tn5, Ndv[−] | 65 |
| CE359 | str-1, lps-359::Tn5[c], LPS V, Ndv[−] | 75 |
| CE360 | str-1, lps-6::Tn5, LPS V, Ndv[−] | 65 |

[a]All strains were derived from wild isolate R. etli CFN42 [ATCC # 51251].
[b]str-1, ery-1, and lps mutations alter streptomycin sensitivity, erythromycin sensitivity, or lipopolysaccharide; LPS I, III, IV, and V indicate SDS- or DOC-PAGE bands exhibited by the strain in addition to LPS II; Ndv[−], elicits incomplete nodule development.
[c]It has not been demonstrated that the Tn5 insertion is responsible for the lps mutation of this strain.

PAGE Analysis of R. etli LPSs: The LPSs from R. etli CE3 and various mutants were analyzed by DOC-PAGE (FIG. 2). LPS I and LPS II were the major components of the parent (CE3) LPS. The LPS I band was detected in greatly reduced amount in the LPS from CE359 and not detected in any LPSs from the other mutants examined. All of the mutant LPS preparations contained LPS II and, in addition, other low molecular weight forms of LPS designated LPS III (CE350), LPS IV (CE121, CE356, CE357), and LPS V (CE359, CE360). The only exception was the LPS preparation from CE358 which contained only LPS II. These different forms of LPS were distinguishable by their differing abilities to bind four monoclonal antibodies (JIM26, JIM27, JIM28, and JIM29); i.e. it was previously reported that LPS IV and V bind all four monoclonals while LPS III binds only JM26, and LPS II does not bind to any of the monoclonals (75).

Analysis of the *R. etli* CE3 LPS Oligosaccharides by High Performance Anion-exchange Liquid Chromatography (HPAEC): Analysis of the mild acid hydrolysate from CE3 LPS by HPAEC showed (FIG. 19A) the presence of five components, OS1–OS5. Fractions OS1 and OS2 were identified as monomeric Kdo and GalA, respectively, by comparing retention times to those of authentic standards. The monomeric Kdo, OS1, eluted as several peaks due to the formation of various anhydro forms during the mild acid hydrolysis procedure (76, 77). Subjection of standard Kdo to the mild acid hydrolysis conditions resulted in the same peaks as those observed for OS1 from the LPS samples. Preparation and GLC-MS analysis of the trimethylsilyl methylglycosides of OS2 showed that it was composed of only GalA. Proton NMR analysis of OS3 and 5 showed that their spectra (not shown) matched those published (18) for the major tetra- and trisaccharide components, respectively, from this LPS; therefore, these previously reported structures (Structures I and II shown above) can be assigned to OS3 and OS5. Oligosaccharide OS4 had the same glycosyl composition as the tetrasaccharide, OS3; namely, GalA, Man, Gal, and Kdo. The relative molar ratio of OS2 (GalA)/ OS3+OS4 (tetramers)/OS5 (trimer) was 1:1:1 and was determined using molar response factors of standard monomeric GalA for OS2 and of a pectic trisaccharide for OS3, OS4, and OS5.

Oligosaccharide OS4 Is a Tetrasaccharide with an Anhydro Kdo Residue at Its Reducing End: As stated above, the glycosyl composition of OS4 was the same as that for OS3. Methylation analysis also showed that OS4 had the same glycosyl linkages as OS3; namely, terminal-GalA/terminal-Gal/4,6-linked Man in a 1:1:1 ratio. The methylation procedure used for this analysis destroyed the Kdo residue and prevented its analysis; however, the various types of Kdo linkages in these LPSs are described below. Analysis by negative FAB-MS of the oligosaccharides prior to purification by HPAEC showed [M-H]$^-$ ions of m/z 589, 719, and 737. The ions of m/z 589 and 737 are due to the tri- and tetrasaccharides (Structures II and I, respectively). The ion at m/z 719 is consistent with a tetrasaccharide that lacks a water molecule, i.e. minus 18 atomic mass units, and could be due a lactone or anhydro version of this molecule. Fractions OS3 and OS4, purified by HPAEC, were reduced with NaBD$_4$, permethylated, and analyzed by ES-MS. Fraction OS3 gave the ions expected for a molecule derived from a tetrasaccharide that contained the expected reducing Kdo pyranose residue; namely, [M+NH$_4$]$^+$ and [M+NH$_4$+Na$^+$]$^+$ of m/z 983 and 1005, respectively. Analysis of OS4, resulted in ions of m/z 937 and 959, [M+NH$_4$]$^+$ and [M+NH$_4$+Na$^+$]$^+$, respectively. These latter ions were also present in OS3 indicating that this fraction was contaminated with some anhydro or lactone form of the tetrasaccharide. The 46 atomic mass units difference between OS3 and OS4 is not consistent with a lactone which would have been reduced with NaBD$_4$; however, it is consistent with an anhydro-Kdo derivative.

NMR analysis of OS4 gave a complex spectrum (not shown). The complexity of the spectrum may indicate that OS4 contained more than one type of anhydro-Kdo residue. The typical resonances for the methylene protons from the reducing Kdo pyranose residue of OS3 ($\delta$ 1.8 and 2.1) were absent. This apparent lack of the Kdo methylene proton resonances can occur for oligosaccharides containing certain anhydro forms of Kdo (78). In a 4,7- or 4,8-anhydro-Kdo residue, the methylene geminal protons are adjacent to a C-2 carbonyl rather than to the hemi-ketal C-2 of a normal reducing Kdo pyranose and are, therefore, quite acidic and easily exchanged with deuterium during preparation of the sample for NMR analysis. Additionally, if not fully exchanged with deuterium, the chemical shifts of such geminal methylene protons are shifted far downfield (e.g. to $\delta$ 2.90 and 3.3 (78)) compared to their resonances in the tetramer with a normal Kdo pyranose residue (e.g. $\delta$ 1.8 and 2.1). This combination of deuterium exchange and downfield chemical shift into the region near the glycosyl ring protons, make these methylene protons difficult to observe under the best conditions. Thus, glycosyl composition, glycosyl linkage, mass spectrometry, and NMR analyses support the conclusion that OS4 is a version of the tetrasaccharide that contains either a 4,7- or a 4,8-anhydro-Kdo residue at its reducing end; i.e. $\alpha$-Gal-(1→6)-[$\alpha$-GalA-(1→4)]-$\alpha$-Man-(1→5)-[4,7- or 4,8-anhydro]-Kdo.

Figure 19A:
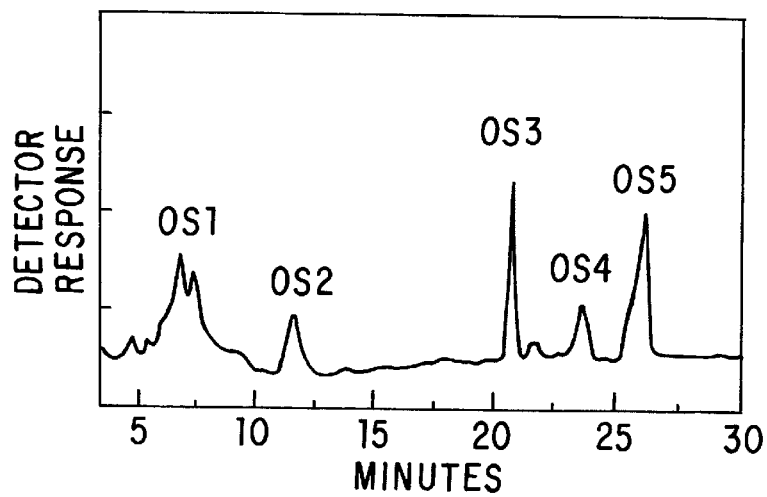
FIG. 19 shows the analysis by HPAEC of the LPS core oligosaccharides obtained from *Rhizobium etli* CE3 LPS (A), and CE358 LPS (B).
Figure 19B:
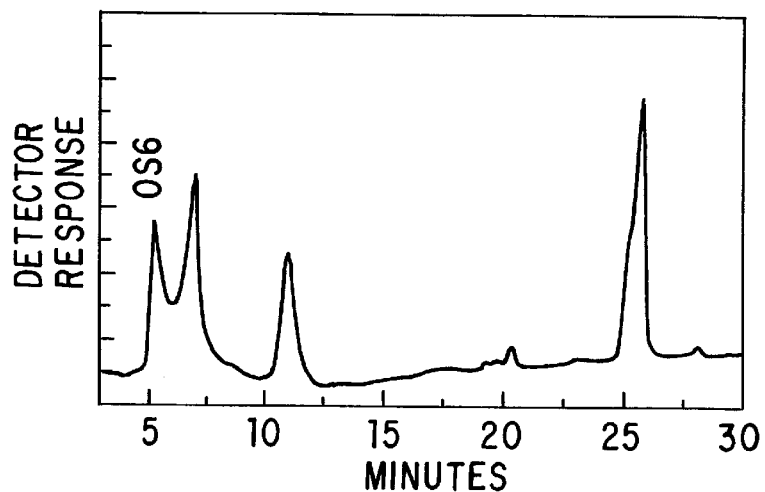

Characterization of the Core Oligosaccharides Purified from the LPSs of *R. etli* Mutants: FIG. 19B shows the HPAEC profile of the mild acid hydrolysates from mutant CE358. The HPAEC profiles for strains CE350, CE357, CE356, CE121, CE359, and CE360 were identical to that of CE3 (FIG. 19A). For strain CE358, OS3 and 4 were replaced by OS6. The relatively short retention time of OS6 indicates that it is not as acidic as the other oligosaccharide components. This was confirmed by chemical analysis which is described further below.

As in the CE3 parent LPS, the GalA/tetramer/trimer ratio for all the mutant LPSs, except that from CE358 in which OS6 replaces OS3 and OS4, is 1:1:1. Thus, of the strains examined in this report, only strain CE358 (from complementation group I) appears to be altered in the core oligosaccharides that are released from the LPS by mild acid hydrolysis.

Negative ion FAB-MS analysis (spectrum not shown) of the mild acid hydrolysate of CE358 LPS gave two major ions; one of [M-H]$^-$ m/z=589 which was due to the GalA$_2$Kdo trisaccharide (OS5$_1$), and one of [M-H]$^-$ m/z= 561 which was consistent with a trisaccharide consisting of 2 hexosyl (flex) and 1 Kdo residues, Hex$_2$Kdo. These results were confirmed by ES-MS analysis of the reduced permethylated oligosaccharides.

The Hex$_2$Kdo trisaccharide (OS6) was isolated by HPAEC and its structure deduced by glycosyl composition, linkage, and NMR analyses. Composition analysis showed that it consisted of Gal, Man, and Kdo. Glycosyl linkage analysis of the neutral sugars showed the presence of terminal Gal and 6-linked Man. The proton NMR spectrum of OS6 (spectrum not shown) matched that previously reported for a Hex$_2$Kdo trisaccharide from another $\alpha$ region mutant, CE109 (67). This result was consistent with the fact that HPAEC analysis of the mild acid hydrolysate of CE109 LPS also showed the presence of OS6 (data not shown). Thus NMR, FAB-MS, and HPAEC analyses strongly suggest that OS6 from CE358 has the same structure as that previously reported (47, 67) CE109 trisaccharide; namely, $\alpha$-Gal-(1→6)-$\alpha$-Man-(1→5)-Kdo.

Analysis of the Intact LPSs from the *R. etli* Mutants: The above results showed that only one mutant, CE358, was altered in the core oligosaccharides released by mild acid hydrolysis of its LPS. However, it was necessary to examine the mutant LPSs prior to mild acid hydrolysis in order to determine if there were other differences that may not have been detectable due to the mild acid hydrolysis conditions.

Small amounts of the LPSs were methylated and carboxymethyl reduced. This was followed by the preparation and GLC-MS analysis of the PMAAs. GLC-MS analysis of the LPSs from strains CE350, 357, and 358 was undertaken. The LPSs from the other mutants had the same glycosyl linkages as found for strain CE357. Peak 1, which was present only in the LPS from strain CE350, had a retention time and fragmentation pattern consistent with the PMAA of terminal Gal (m/z=205, 162, 118, 161). Peak 2 was present only in the LPS from strain CE358 and was due to the PMAA of 6-linked Man (m/z=233, 189, 162, 118). Peak 3, in the case of CE350 LPS, was due to the PMAA of terminal GalA (m/z=235, 191, 162, 118) in which the carboxyl group had been reduced with $NaBD_4$ prior to hydrolysis and acetylation. Minor ions of m/z=233 and 189 were present in peak 3 from CE350 LPS and indicated the presence of small amounts of 6-linked Gal. In the case of the LPSs from CE358 and CE357, as well as the other remaining mutant LPSs, terminal galactose (peak 1) was not detected, and peak 3 consisted of a mixture of the PMAAs derived from 6-linked Gal and terminal GalA; m/z=235 (233), 191 (189), 162, 118. The ratio of the 233:235 (or 189:191) ion intensities is somewhat reflective of the 6-linked Gal/terminal GalA ratio and was 0.077, 0.15, and 0.23 for the LPSs from CE350, CE357, and CE358, respectively. The larger ratio for CE358 compared with that for CE357 LPS was consistent with the fact that the former LPS lacks one of the GalA residues. Peak 4 was the PMAA of 4,6-linked Man (m/z= 261,118) and was found in the LPSs from all the mutants except CE358 which contained only 6-linked Man (peak 2).

With one exception, these data are consistent with structures of the oligosaccharides released by mild acid hydrolysis. The exception is that the Gal residue in the mild acid released oligosaccharides is terminally linked while it is 6-linked in the intact LPSs, except for that from CE350 in which it is largely terminally linked. Thus, in these LPSs, except for the LPS from CE350, the Gal of the core tetrasaccharide has a mild acid labile residue, presumably Kdo, attached at O-6. Since it is known that the O-chain polysaccharide purified by mild acid hydrolysis has a Kdo residue at its reducing end, it is likely that it is this residue which is attached to O-6 of Gal in these intact LPSs.

The linkages of the Kdo residues for several of the LPSs, e.g. from strains CE357 and CE358, were determined by methylation, carboxymethyl reduction (lithium triethylborodeuteride), mild acid hydrolysis (0.1 M trifluoroacetic acid at 80 C. for 30 min), reduction (sodium borodeuteride), normal acid hydrolysis (2 M trifluoroacetic acid at 121 for 2 h), reduction (sodium borodeuteride), and preparation of the PMAAs. Three types of Kdo residues were found in these LPSs; terminally linked Kdo (primary fragments of m/z 89, 205, 206, 250, and 366), 5-linked Kdo (m/z 89, 206, and 394), and 4,5-linked Kdo (m/z 89, and 422). The 4,5- and 5-linked Kdo residues are consistent with the tri- and tetrasaccharide core oligosaccharide structures, and the terminal Kdo is presumably due, in part, to the Kdo residue that is attached to O-6 of the core tetrasaccharide Gal residue. Thus, it is likely that the core structure for the LPSs from CE3 and its mutants, except for CE350, contains terminal Kdo attached to O-6 of the Gal residue.

In summary, these methylation results from the intact LPSs showed (a) that the intact core region of these LPSs contain a Kdo residue attached to O-6 of the Gal residue, (b) that this Kdo residue is the likely site of O-chain attachment, and (c) that the LPS from mutant CE350 lacks this Kdo residue.

Alditol acetate analysis of the intact LPSs from CE350, 356, 357, 359, 360, and 121 show that they all contain small amounts of glycosyl residues previously reported (12) to be in the O-chain polysaccharide, e.g. GlcA, methylated Rha, Fuc, methylated Fuc, and quinovosamine (Qvn). Since PAGE and immunoblot analyses (30) showed that the monoclonals only bind to LPS I, III, IV, or V, and not to LPS II, these results indicate that the minor amounts of LPS III, IV, and/or V that are present in these mutants are forms of the LPS that contain various truncated O-chains. This was confirmed by purifying a small amount of LPS IV from strain CE121 using gel filtration chromatography in the presence of DOC. Analysis of this LPS IV showed the presence of GlcA/2-O-MeRha/Fuc/2,3-di-O-MeFuc/Man/Qvn=1:1:1:1:1:1. The LPS from the parent strain, CE3, has these sugars in roughly a 4:4:4:1:1:1 ratio with the exception that a 2,3,4-tri-MeFuc residue replaces the 2,3-di-O-MeFuc residue. The repeating unit of this O-chain is comprised of GlcA/2-O-MeRha/Fuc in a 1:1:1 ratio. Thus, the reduced level of these sugars in LPS IV and its faster PAGE mobility compared with that for LPS I are consistent with the concept that LPS IV has a truncated O-chain.

Figure 20:
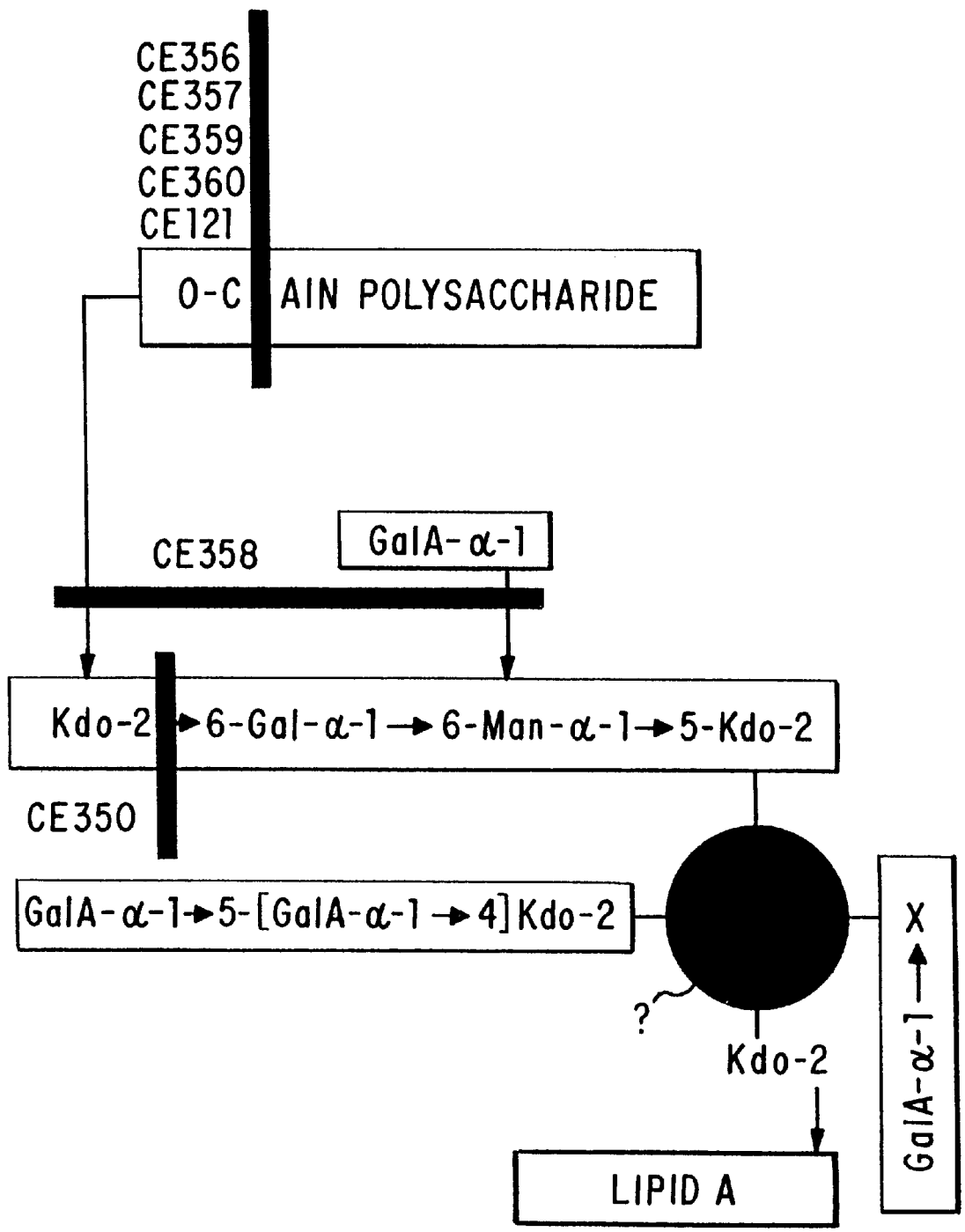
FIG. 20 shows a schematic representation of the possible structure of the LPS from *R. etli* CE3 and its various mutants. Mutant CE358 lacks the GalA residue α-linked to O-4 of Man, as well as the O-chain polysaccharide. Mutant CE350 lacks the Kdo residue attached to O-6 of Gal. However, this mutant is somewhat leaky in that a small percentage of its LPS contains this Kdo residue as well as a truncated portion of the O-chain polysaccharide. Mutants CE356, CE357, CE359, CE360, and CE121 all contain a complete core region as well as various truncated versions of the O-chain polysaccharide. The shaded circle indicates that it is not yet known how these various core oligosaccharides are linked together in the complete molecule. The X represents a moiety or chemical environment which renders the GalA glycoside bond labile to mild acid. The core region is attached via a mild acid labile substituent (presumably Kdo) to O-6 of the lipid A GlcN residue (61).

The results described above suggest that the "rough" LPSs (i.e. LPS II) from the parent and mutant strains have the structures shown in FIG. 20. The LPS II core region is comprised of the previously reported tetra- and trisaccharide molecules (47, 67) (Structures I and II), with a Kdo residue linked to O-6 of the tetrasaccharide Gal residue. This Kdo residue may be the site of O-chain attachment.

The results described above also show that mild acid hydrolysis releases monomeric GalA from all of the LPSs. Thus, the core region must contain a "GalA-1→X" in which X is an unidentified substituent or chemical environment which renders the GalA glycoside bond labile to mild acid. The mechanism by which monomeric GalA is released from the LPS by mild acid hydrolysis is not yet understood.

The precise arrangement of the core components in the intact LPS is not known. It is possible that the tri- and tetrasaccharides are present on two different types of LPS molecules. However, their presence in approximately a 1:1 ratio in both the parent and in all of the mutant LPSs indicates that there may be a single LPS species which contains all of the core elements.

The two mutants which vary in their core structures are CE350 and CE358. The core region from strain CE350 lacks the Kdo residue that is normally attached to O-6 of Gal, and the core region from strain CE358 lacks the GalA residue that is normally attached to O-4 of the Man residue. The missing Kdo residue in CE350 LPS suggests that the defective gene in this mutant may encode a specific CMP-Kdo transferase. It should be noted that glycosyl linkage analysis of the CE350 LPS suggests that a small portion of the Gal residues has Kdo at O-6. Thus, this mutation does not lead to a complete lack of this Kdo residue. That some of the CE350 LPS molecules have this Kdo residue, and that a truncated version of the O-chain is attached to that residue, is supported by the fact that CE350 LPS preparations have LPS III, contain small amounts of O-chain sugars, and bind the JIM26 monoclonal antibody. On the other hand the LPS from strain CE358 seems to consist only of LPS II, and completely lacks O-chain sugars, suggesting that (a) the GalA residue that is missing from the O-4 position of the Man residue may be required for transfer of O-chain to the core region, and (b) that the defective gene in CE358 may encode a UDP-GalA transferase.

Other than those of CE350 and CE358, LPSs analyzed in this study have all of the core components and contain various forms of truncated O-chain as evidenced by the presence of typical O-chain glycosyl residues.

EXAMPLE 5

Antagonism Using LPS and Lipid A from *R. etli*

Ability of *R. etli* LPS and Lipid A Preparations to Antagonize TNF Production from *E. coli* LPS in Equine Blood: *R. etli* (formerly *R. leguminosarum* bv. phaseoli) CE3 lipid A is unique in structure when compared to other gram-negative bacterial lipid As. CE3 LPS and Lipid A have been found to be very poor in comparison to *E. coli* LPS at inducing TNF in equine blood (see Results below). With this in mind, the following data demonstrates that *R. etli* CE3 LPS and lipid A can antagonize the ability of *E. coli* LPS to induce TNF in equine blood.

Methods: Equine blood was pre-incubated for 1 h with PBS, 10 ng/ml of *R. etli* CE3 LPS in PBS or 10 ng/ml of *R. etli* CE3 lipid A. After pre-incubation, 10 ng/ml of *E. coli* 055:B5 LPS was added to the blood and incubated for 6 h at 37° C. The plasma was then collected and tested for its ability to kill Wehi Clone 13 cells (which are sensitive to killing by TNF).

Results: The effect of *R. etli* CE3 LPS and lipid A on the ability of *E. coli* LPS to induce TNF production in equine blood is shown in Table IV.

TABLE IV

Effect of *R. etli* CE3 LPS and lipid A on TNF Induction

| | TNF Production | |
|---|---|---|
| Sample | Horse 1 | Horse 2 |
| PBS + Ec LPS | 1106 | 179 |
| Re LPS | 267 | 25 |
| Re LPS + Ec LPS | 533(48%) | 96(54%) |

Ec = *E. coli*, Re = *R. etli*
% values are compared to Ec LPS alone

The results suggest that the *R. etli* LPS can cause up to 50% reduction in the ability of *E. coli* LPS to stimulate TNF in equine blood. However, the control levels of TNF production by *E. coli* LPS are low (by 3 to 4 orders of magnitude) when compared to the results described below. The control levels of TNF production by *R. etli* LPS are similar to previous data. These results demonstrate that *R. etli* LPS is a potent antagonist for *E. coli* LPS *R. etli* lipid A is believed to also act as an antagonist.

Ability of *R. etli* LPS and Lipid A Preparations to Stimulate Reduced Levels of TNF Production in Equine Blood. In addition, the following in vitro experiment regarding the therapeutic effects of the claimed compositions was also conducted.

Equine blood was incubated with a sample (either LPS from *R. leguminosarum* bv. CE3, lipid A from *R. leguminosarum* bv. CE3, or control saline) for 6 hours at 37° C. The plasma was then collected and tested for its ability to kill Wehi Clone 13 cells. Wehi Clone 13 cells are sensitive to killing by TNF. The following table represents the results of the assay.

TABLE V

| Sample | Concentration | Horse 1 TNF (pg/mL) | Horse 2 TNF (pg/mL) | Percent of *E. coli* |
|---|---|---|---|---|
| Control 1 | | 22 | 63 | — |
| Control 2 | | 10 | 9 | |
| *E. coli* 055:B5 LPS | 10 ng/mL | 29,000 | 360,000 | — |
| | 100 ng/mL | 250,000 | 600,000 | — |
| | 1000 ng/mL | 8,100,000 | 12,600,000 | — |
| Rhizobial lipid A | 10 ng/mL | 17 | 1,800 | 0.06%, 0.50% |
| | 100 ng/mL | 154 | 952 | 0.06%, 0.16% |
| | 1000 ng/mL | — | 44,000 | —, 0.35% |
| Rhizobial LPS | 10 ng/mL | 200 | 350 | 0.69%, 0.10% |
| | 100 ng/mL | 400 | 2,600 | 0.16%, 0.43% |
| | 1000 ng/mL | 2,200 | 5,500 | 0.03%, 0.04% |

As can be seen, the level of TNF stimulation caused by the compositions of the invention is again far less than that of the lipid A or LPS from naturally occurring gram-negative *E. coli* bacteria. This experiment demonstrates that the compositions of the invention are effective to stimulate TNF to a lesser degree than would be expected from standard gram-negative endotoxic activity. It is well known that equine endotoxin sensitivity is analogous to human endotoxin sensitivity.

The above-described experiments demonstrate the efficacy of Rhizobial LPS in methods of treating of LPS-mediated disorders. The Rhizobial LPS produced a similarly attenuated immune response, which is strongly indicative of, or at least reasonably correlated to, its ability to act as an antagonist to harmful lipid A or LPS in an LPS-mediated disorder.

Treatment Methods

Methods of treating septic shock or toxic shock in a subject using the compositions of the present invention are provided. In particular, the LPSs and lipid As as described herein may be used alone or in combination to antagonize endotoxic activity of gram-negative bacteria endotoxic activities associated with sepsis/toxic shock. It is contemplated that the present invention is directed to human and animal subjects or patients.

In one method, an amount of purified LPS or lipid A of *R. leguminosarum* or *R. etli* is administered to the subject. The administered LPS or lipid A, without wishing to be bound by theory, is specifically capable of competing with the lipid binding protein or LPS of a gram(−) bacteria associated with septic shock. Again, without wishing to be bound by theory, one way this inhibition can occur is the subject purified LPS or lipid A binds the relevant immune system related proteins or receptors and thereby prevents the formation of a bond between LPS binding protein and the toxic lipid A or LPS. Another possible mechanism of inhibition results from the binding of the subject LPS or lipid A to a receptor, e.g. the CD14 receptor on the macrophage, such that a less toxic (and potentially non-toxic) lipid A or LPS occupies available receptor sites and thereby causes a less severe systemic response.

The compositions and products of the present invention may be administered orally, parenterally (e.g., intravenously), by intramuscular injection, by intraperitoneal injection, topically, transdermally, or the like, although parenteral intravenous administration is typically preferred, especially in acute cases of endotoxicosis. The exact amount of such compositions and products required will vary from subject to subject, depending on the species, age, weight and general condition of the subject, the severity of the disease that is being treated, the particular compound used, its mode of administration, and the like. Thus, it is not possible to specify an exact amount. However, an appropriate amount may be determined by one of ordinary skill in the art using only routine experimentation given the teachings herein and optimization procedures known in the art. Generally, dosage will preferably be in the range of about 0.0001 mg/patient to 600 mg/patient, more preferably from about 0.001 mg/patient to 350 mg/patient, even more preferably from 0.01 to 100 mg/patient. One skilled in the art, however, could readily elucidate other dosage ranges and regimens and the above are expressly intended to be non-limiting. See, e.g., *Remington's Pharmaceutical Sciences* (latest edition).

Depending on the intended mode of administration, the products and compositions of the present invention can be formulated into pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected compound in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences* (latest edition).

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Vaccines

The compositions and products of this invention can be used in the construction of a vaccine comprising an immunogenic amount of the lipid A analog(s) or LPS and a pharmaceutically acceptable carrier. The vaccine can be the entire LPS or lipid A (or heterogenous mixtures thereof) or immunogenic portions thereof. The vaccine can also be potentially cross-reactive with antibodies to other lipid A or LPS analogs. The vaccine can then be used in a method of preventing septic shock or other complications of gram(−) bacteria infection (including LPS-mediated disorders such as Lyme disease and LPS-mediated exacerbation of latent/active viral infections such as HIV-1, cytomegaloviruses, herpes simplex viruses and influenza viruses).

Immunogenic amounts of lipid A analogs and LPSs can be determined using standard procedures. Briefly, various concentrations of a putative specific immunoreactive lipid A analogs or LPSs are prepared, administered to an animal and the immunological response (e.g., the production of antibodies) of an animal to each concentration is determined.

The pharmaceutically acceptable carrier in the vaccine of the instant invention can comprise saline or other suitable carriers (Arnon, R. (Ed.) *Synthetic Vaccines* I:83–92, CRC Press, Inc., Boca Raton, Fla., 1987). An adjuvant can also be a part of the carrier of the vaccine, in which case it can be selected by standard criteria based on the lipid A or LPS or other product used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention provides methods of preventing or treating gram (−) bacteria associated septic shock and associated diseases by administering the vaccine to a subject.

Adjuvants

The lipid As, LPSs, compositions and products of the present invention may be used as adjuvants in a vaccine preparation. As an adjuvant, the composition or product can enhance the immune response to the immunogen of the vaccine preparation without concomitant adverse reactions. As such, a vaccine preparation containing the composition or product as an adjuvant along with whole killed or partial gram(−) bacteria could be used to vaccinate against a subsequent challenge from other gram(−) bacteria. Likewise, the immune response to viral immunogens could be enhanced utilizing the immunostimulatory effect of the lipid As, LPSs, compositions and products described herein.

Immunostimulation

In addition, the compositions and products of the present invention may be used to directly stimulate the immune system. In such procedures, the compositions and products would be administered as described above to a patient or subject that is immune-compromised. It is important to note that the mechanism of action is not necessarily the same as that described for adjuvants and vaccines above. Instead, the compositions and products are used to directly stimulate cytokine production, where these increased cytokines then ameliorate the condition of the immune-compromised patient.

Antibodies

Antibodies can be made as described in Harlow and Lane, *Antibodies; A Laboratory Manual,* Cold Spring Harbor Laboratory, Cold Spring Harbor, N.Y., 1988. Briefly the compositions and products can be injected into an animal or other subject in an amount and in intervals sufficient to elicit an immune response. Antibodies can either be purified directly, or spleen cells can be obtained from the animal. The cells are then fused with an immortal cell line and screened for antibody secretion. The antibodies can be used to screen samples for cells containing the antigen. The presence of *Rhizobium leguminosarum* can then be detected in a sample using the antibodies.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

REFERENCES

1. Alving C. 1992. Lipid A and liposomes containing lipid A as adjuvants for vaccines. In: Morrison D. C. and J. L. Ryan, (eds.), Bacterial endotoxic lipopolysaccharides, Volume II, Immunopharmacology and pathophysiology, CRC Press, Boca Raton, Ann Arbor, London, Tokyo.
2. Arend W. P. 1991. Interleukin 1 receptor antagonist: a new member of the interleukin 1 family. J.Clin.Invest. 88:1445–1451.
3. Beutler B. and A. Cerami. 1988. Tumor necrosis, cachexia, shock, and inflammation: a common mediator. Ann.Rev.Biochem. 57:505–518.
4. Bhat U. R. and R. W. Carlson. 1992. A new method for the analysis of amide-linked hydroxy fatty acids in lipid-As from gram-negative bacteria. Glycobiology 2:535–539.
5. Bhat U. R., H. Mayer, A. Yokota, R. I. Hollingsworth, and R. W. Carlson. 1991. Occurrence of lipid A variants with 27-hydroxyoctacosanoic acid in lipopolysaccharides from the Rhizobiaceae group. J.Bacteriol. 173:2155–2159.
6. Bogard W. C., Jr., S. A. Siegel, A. O. Leone, E. Damiano, D. J. Shealy, T. M. Ely, B. Frederick, M. A. Mascelli, R. C. Siegel, B. Machielse, D. Naveh, P. M. Kaplan, and P. E. Daddona. 1993. Human monoclonal antibody HA-1A binds to endotoxin via an epitope in the lipid A domain of lipopolysaccharide. J.Immunol. 150:4438–4449.
7. Bogard W. C. Jr. and S. A. Siegel. 1991. The human monoclonal antibody HA-1A: Studies on the epitope location with the endotoxin molecule and epitopic exposure on the surface of viable Gram-negative bacteria. Circ.Shock 34:119.
8. Carlson R. W., S. Kalembasa, D. Turowski, P. Pachori, and K. D. Noel. 1987. Characterization of the lipopolysaccharide from a *Rhizobium phaseoli* mutant that is defective in infection thread development. J.Bacteriol. 169:4923–4928.
9. Carlson R. W., R. E. Sanders, C. Napoli, and P. Albersheim. 1978. Host-symbiont interactions III. Purification and characterization of Rhizobium lipopolysaccharides. Plant Physiol. 62:912–917.
10. Christ W. J., T. Kawata, L. D. Hawkins, S. Kobayashi, O. Asano, and D. P. Rossignol. 1993. European patent EP-536969-A2. Derwent Publications, Ltd.,
11. Davis J. 1993. New approaches to septic shock. SCRIP 1793:22–23.
12. Dinarello C. A. 1991. Interleukin-1 and interleukin-1 antagonism. Blood 77:1627–1652.
13. Fink M. P. 1993. Adoptive immunotherapy of Gram-negative sepsis: Use of monoclonal antibodies to lipopolysaccharide. Crit.Care Med. 21 Suppl.:S32–S39.
14. Galanos C., V. Lehmann, O. Luderitz, E. Th. Rietschel, O. Westphal, H. Brade, L. Brade, M. A. Freudenberg, T. Hansen-Hagge, T. Luderitz, G. McKenzie, U. Schade, W. Strittmatter, K. Tanamoto, U. Zahringer, M. Imoto, H. Yoshimura, M. Yamamoto, T. Shimamoto, S. Kusumoto, and T. Shiba. 1984. Endotoxic properties of chemically synthesized lipid A part structures: comparison of synthetic lipid A precursor and synthetic analogues with biosynthetic lipid A precursor and free lipid A. Eur.J.Biochem. 140:221.
15. Goldman R. C., J. O. Capobianco, C. C. Doran, and A. G. Matthysse. 1992. Inhibition of lipopolysaccharide synthesis in *Agrobacterium tumefaciens* and *Aeromonas salmonicida*. J.Gen.Microbiol. 138:1527–1533.
16. Goldman R. C., C. C. Doran, and J. O. Capobianco. 1988. Analysis of lipopolysaccharide synthesis in *Salmonella typhimurium* and *Escherichia coli* using agents which block incorporation of KDO. J.Bacteriol. 170:2185–2192.
17. Golenbock D. T., R. Y. Hampton, N. Qureshi, K. Takayama, and C. R. H. Raetz. 1991. Lipid A-like molecules that antagonize the effects of endotoxins on human monocytes. J. Biol.Chem. 266:19490–19498.
18. Greenman R. L., R. M. H. Schein, M. A. Martin, and et al. 1991. A controlled clinical trial of E5 monoclonal IgM antibody to endotoxin in the treatment of Gram-negative sepsis. JAMA 266:1097–1102.
19. Krauss J. H., U. Seydel, J. Weckesser, and H. Mayer. 1989. Structural analysis of the nontoxic lipid A of *Rhodobacter capsulatus* 37b4. Eur.J.Biochem. 180:519–526.
20. Lee J.-D., K. Kato, P. S. Tobias, T. N. Kirkland, and R. J. Ulevitch. 1992. Transfection of CD14 into 70Z/3 cells dramatically enhances the sensitivity to complexes of lipopolysaccharide (LPS) and LPS binding protein. J.Exp.Med. 175:1697–1705.
21. Loppnow H., H. Brade, I. Durrbaum, C. A. Dinarello, S. Kusomoto, E. Th. Rietschel, and H.-D. Flad. 1989. Interleukin 1 induction-capacity of defined lipopolysaccharides partial structures. J.Immunol. 142:3229.
22. Loppnow H., P. Libby, M. Freudenberg, J. H. Krauss, J. Weckesser, and H. Mayer. 1990. Cytokine induction by lipopolysaccharide (LPS) corresponds to lethal toxicity and is inhibited by nontoxic *Rhodobacter capsulatus* LPS. Infect. Immun. 58:3743–3750.
23. Morrison D. C. and J. L. Ryan. 1987. Endotoxins and disease mechanisms. Ann.Rev.Med. 38:417–432.
24. Noel K. D., K. A. VandenBosch, and B. Kulpaca. 1986. Mutations in *Rhizobium phaseoli* that lead to arrested development of infection threads. J.Bacteriol. 168:1392–1401.
25. Raetz C. R. H., R. J. Ulevitch, S. D. Wright, C. H. Sibley, A. Ding, and C. F. Nathan. 1991. Gram-negative endotoxin: an extraordinary lipid with profound effects on eukaryotic signal transduction. FASEB Journal 5:2652–2660.
26. Rietschel E. Th., L. Brade, B. Lindner, and U. Zahringer. 1992. Biochemistry of lipopolysaccharides. In: p. 341. Morrison D. C. and J. L. Ryan, (eds.), Bacterial endotoxic lipopolysaccharides, Volume I, Molecular biochemistry and cellular biology, CRC Press, Boca Raton, Ann Arbor, London, Tokyo.

27. Rietschel E. Th., L. Brade, U. Schade, C. Galanos, M. A. Freudenberg, O. Luderitz, S. Kusumoto, and T. Shiba. 1987. Endotoxic properties of synthetic pentaacyl lipid A precursor Ib and a structural isomer. Eur.J.Biochem. 169:27.
28. Rubin R. M., J. Noland, and J. T. Rosenbaum. 1992. Reduction of endotoxin-induced vascular permeability by monoclonal antibodies against lipopolysaccharide determinants. Circ.Shock 36:217–223.
29. Ryan J. M. and H. E. Conrad. 1974. Structural hetergeneity in the lipopolysaccharide from *Salmonella newington*. Arch.Biochem.Biophys. 162:530–535.
30. Schumann R. R., S. R. Leong, G. W. Flaggs, P. W. Gray, S. D. Wright, J. C. Mathison, P. S. Tobias, and R. J. Ulevitch. 1990. Structure and function of lipopolysaccharide binding protein. Science 249:1429–1431.
31. Takada H. and S. Kotani. 1992. Structure-function relationships of lipid A. In: p. 107–134. Morrison D. C. and J. L. Ryan, (eds.), Bacterial endotoxic lipopolysaccharides, Volume I, Molecular biochemistry and cellular biology, CRC Press, Boca Raton, Ann Arbor, London, Tokyo.
32. Takayama K., N. Qureshi, B. Beutler, and T. N. Kirkland. 1989. Dephosphoryl lipid A from *Rhodopseudomonas sphaeroides* ATCC 17023 blocks induction of cachectin in macrophages by lipopolysaccharide. Infect.Immun. 57:1336–1338.
33. Takayama K., N. Qureshi, E. Ribi, J. L. Cantrell, and K. Amano. 1983. Use of endotoxin in cancer immunotherapy and characterization of its nontoxic but active lipid A components. In: p. 219–233. Anderson L. and F. M. Unger, (eds.), Bacterial lipopolysaccharides, American Chemical Society, Washington, D.C.
34. Tobias P. S., K. Soldau, L. Kline, J.-D. Lee, K. Kato, T. P. Martin, and R. J. Ulevitch. 1993. Cross-linking of lipopolysaccharide (LPS) to CD14 on THP-1 cells mediated by LPS-binding protein. J.Immunol. 150:3011–3021.
35. Tobias P. S., K. Soldau, and R. J. Ulevitch. 1989. Identification of a lipid A binding site in the acute phase reactant lipopolysaccharide binding protein. J.Biol.Chem. 264:10867–10871.
36. Von Eschen K. 1992. Monphosphoryl lipid A and immunotherapy. In: Morrison D. C. and J. L. Ryan, (eds.), Bacterial endotoxic lipopolysaccharides, Volume II, Immunopharmacology and pathophysiology, CRC Press, Boca Raton, Ann Arbor, London, Tokyo.
37. Wang M.-H., W. Feist, H. Herzbeck, H. Brade, S. Kusumoto, E. Th. Rietschel, H.-D. Flad, and A. J. Ulmer. 1990. Suppressive effect of lipid A partial structures on lipopolysaccharide or lipid A-induced release of interleukin 1 by human monocytes. FEMS Microbiol.Immunol. 64:179.
38. Warren H. S., R. L. Danner, and R. S. Munford. 1992. Anti-endotoxin monoclonal antibodies. N.Engl.J.Med. 326:1153–1157.
39. Westphal O. and K. Jann. 1965. Bacterial lipopolysaccharides. Meth.Carbohydr.Chem. 5:83–91.
40. Wollenweber H.-W. and E. Th. Rietschel. 1990. Analysis of lipopolysaccharide (lipid A) fatty acids. J.Microbiol.Methods 11:195–211.
41. Wortel C. H., E. J. Ziegler, and S. J. H. Van Deventer. 1991. Therapy of Gram-negative sepsis in man with anti-endotoxin antibodies: A review. Prog.Clin.Biol.Res. 367:161–178.
42. Wright S. D., R. A. Ramos, P. S. Tobias, R. J. Ulevitch, and J. C. Mathison. 1990. CD14, a receptor for complexes of lipopolysaccharide (LPS) and LPS binding protein. Science 249:1431–1433.
43. York W. S., A. G. Darvill, M. McNeil, T. T. Stevenson, and P. Albersheim. 1985. Isolation and characterization of plant cell walls and cell wall components. Meth.Enzymol. 118:3–40.
44. Ziegler E. J., C. J. Jr. Fisher, C. L. Sprung, and et al. 1991. Treatment of Gram-negative bacteremia and septic shock with HA-1A human monoclonal antibody against endotoxin—A randomized, double-blind, placebo-controlled trial. N.Engl.J.Med. 324:429–436.
45. Ziegler E. J., J. A. McCutchan, J. Fierer, and et al. 1982. Treatment of Gram-negative bacteremia and shock with human antiserum to a mutant *Escherichia coli*. N.Engl.J.Med. 307:1225–1230.
46. Ohno, K., Nishiyama, H., and Nagase, H. 1979. Tetrahedr Lett. 45:4405–4406.
47. Bhat, U. R., Bhagyalakshmi, S. K., and Carlson, R. W. 1991. Carbohydr. Res. 220:219–227.
48. Demary, M., Puzo, G., and Asselineau, J. 1977. Nouv. J. Chimie 2:373–378.
49. Hollingsworth, R. I., Carlson, R. W., Garcia, F., and Gage, D. A. 1990. J. Biol. Chem. 265:12752.
50. Hollingsworth, R. I., Carlson, R. W., Garcia, F., and Gage, D. A. 1989. J. Biol. Chem. 264:9294–9299.
51. Zhang, Y., Hollingsworth, R. I., and Priefer, U. B. 1992. Carbohydr. Res. 231:261–271.
52. Russa, R., Luderitz, O., and Rietschel, E. T. 1985. Arch. Microbiol. 141:284–289.
53. Hollingsworth, R. I. and Lill-Elghanian, D. A. 1989. J. Biol. Chem. 264:14039–14042.
54. Segovia, L., Young, J. P. W., and Martinez-Romero, E. 1993. Int. J. Syst. Bacteriol. 43:374–377.
55. Kotani, S. and Takada H. 1990. Adv. Exp. Med. Biol. 256:13–44.
56. Bhat, U. R., Carlson, R. W., Busch, M., and Mayer, H. (1991) Int. J. Syst. Bacteriol. 41:213–217.
57. Woese, C. R. (1987) Microbiol. Rev. 51:221–271.
58. Carlson, R. W., Bhat, U. R., and Reuhs, B. (1992) in Plant Biotechnology and Development (Gresshoff, P. M., ed) pp. 33–44, CRC Press, Boca Raton, Fla.
59. Noel, K. D. (1992) in Molecular Signals in Plant-Microbe Communications (Verma, D. P. S., ed) pp. 341–357, CRC Press, Boca Raton, Fla.
60. Carlson, R. W., Hollingsworth, R. L., and Dazzo, F. B. (1988) Carbohydr. Res. 176:127–135.
61. Bhat, U. R., Forsberg, L. S., and Carlson, R. W. (1994) J. Biol. Chem. 269:14402–14410.
62. Carlson, R. W. (1984) J. Bacteriol. 158:1012–1017.
63. Cava, J. R., Elias, P. M., Turowski, D. A., and Noel, K. D. (1989) J. Bacteriol. 171:8–15.
64. Diebold, R., and Noel, K. D. (1989) J. Bacteriol. 171:4821–4830.
65. Cava, J. R., Tao, H., and Noel, K. D. (1990) MGG 221:125–128.
66. Brink, B. A., Miller, J., Carlson, R. W., and Noel, K. D. (1990) J. Bacteriol. 172:548–555.
67. Carlson, R. W., Garcia, F., Noel, K. D., and Hollingsworth, R. L (1990) Carbohydr. Res. 195:101–110.
68. Stacey, G., So, J.-S., Roth, L. E., Bhagya Lakshmi, S. K., and Carlson, R. W. (1991) Mol. Plant Microbe Interact. 4:332–340.
69. Perotto, S., Brewin, N. J., and Kannenberg, E. L. (1994) Mol. Plant Microbe Interact. 7:99–112.
70. Reuhs, B. L., Carlson, R. W., and Kim, J. S. (1993) J. Bacteriol. 175:3570–3580.
71. Reuhs, B. L., Kim, J. S., Badgett, A., and Cadson, R. W. (1994) Mol. Plant Microbe Interact. 7:240–247.

72. Peterson, A. A., and McGroarty, E. J. (1985) J. Bacteriol. 162:738–745.
73. Krauss, J. H., Weckesser, J., and Mayer, H. (1988) Int. J. Syst. Bacteriol. 38:157–163.
74. Tsai, C., and Frisch, C. E. (1982) Anal. Biochem. 119:115–119.
75. Tao, H., Brewin, N. J., and Noel, K. D. (1992) J. Bacteriol. 174:2222–2229.
76. McNicholas, P. A., Batley, M., and Redmond, J. W. (1987) Carbohydr. Res. 165:17–22.
77. McNicholas, P. A., Batley, M., and Redmond, J. W. (1986) Carbohydr. Res. 146:219–231.
78. Carlson, R. W., and Krishnaiah, B. S. (1992) Carbohydr. Res. 231:205–219.
79. Noel, K. D., Sanchez, A., Fernandez, L., Leemans, J., and Cevallos, M. A. (1984) J. Bacteriol. 158:148–155.

What is claimed is:

1. A composition for antagonizing gram negative bacterial endotoxic activity, comprising a pharmaceutically acceptable carrier and an antagonizing amount of a lipopolysaccharide from a *Rhizobium etli*.

2. The composition of claim 1, wherein the endotoxic activity is the stimulation of TNF.

3. A composition for antagonizing gram negative bacterial endotoxic activity, comprising a pharmaceutically acceptable carrier and an antagonizing amount of a lipid A from a *Rhizobium etli*.

4. The composition of claim 1, further comprising an antagonizing amount of a lipid A from a *Rhizobium etli*.

5. The composition of claim 1, wherein the pharmaceutically acceptable carrier is saline, mannitol, lactose, starch, magnesium stearate, sodium saccharin, talc, cellulose, glucose, sucrose, magnesium carbonate, water, aqueous dextrose, glycerol, ethanol or a mixture thereof.

6. A method of antagonizing gram negative bacterial endotoxic activity, comprising administering to a subject in need of such antagonization the composition of claim 1.

7. The method of claim 6, wherein the *Rhizobium etli* is Rhizobium etli bv. CF3, *Rhizobium etli* bv. CE109, *Rhizobium etli* bv. CE121, *Rhizobium etli* bv. CE350, *Rhizobium etli* bv. CE356, *Rhizobium etli* bv. CE357, *Rhizobium etli* bv. CE358, *Rhizobium etli* bv. CE359 or *Rhizobium etli bv. CE*360.

8. The method of claim 6, wherein the endotoxic activity is the stimulation of TNF.

9. A method of treating septic or toxic shock in a patient, comprising administering to the patient an effective amount of a lipopolysaccharide from a *Rhizobium etli*.

10. A method of treating or preventing a lipopolysaccharide mediated disorder in a patient, comprising administering to the patient an effective amount of a lipopolysaccharide from a *Rhizobium etli*.

11. A method of extracting lipopolysaccharide from a gram negative bacteria, comprising:
   a) admixing a bacterial pellet from a gram negative bacteria in a solution comprising
      I) ethylenediaminetetraacetic acid (EDTA); and
      ii) triethylamine (TEA) or triethanolamine (TeolA), in a 1:2 to 1:4 ratio of components I) to ii), wherein the resulting solution has a pH of 5.5 to 8.5; and
      agitating the mixture at a temperature of from 25° C. to 60° C. for a period of time sufficient to release the lipopolysaccharide from the bacterial pellet to obtain a released lipopolysaccharide;
   b) contacting the released lipopolysaccharide with polymixin-B-agarose; and
   c) eluting the lipopolysaccharide from the polymixin B-agarose with an eluting solution comprising at least 1% deoxycholate to obtain thereby a lipopolysaccharide product.

12. The method of claim 11, further comprising, before the contacting step b), dialyzing the released lipopolysaccharide.

13. The method of claim 11, wherein the temperature in the agitating step b) is from 30° C. to 50° C.

14. The method of claim 11, wherein the ratio in the admixing step a) is 1:3.

15. The method of claim 11, wherein the pH of the solution in the admixing step a) is from 6.5 to 8.0.

16. The method of claim 12, further comprising, after the dialyzing step, removing any insoluble debris from the released lipopolysaccharide.

17. The method of claim 11, further comprising, after the agitating step b), centrifuging the released lipopolysaccharide and recovering the supernatant.

18. The method of claim 17, further comprising, after the centrifuging step, admixing the supernatant with Tris HCl or $MgCl_2$ until the pH of the mixture is from 7.0 to 9.0 and incubating the pH adjusted mixture with an enzyme selected from the group consisting of an RNase, a DNase, and a protease.

19. The method of claim 11, further comprising, after the contacting step b), washing the polymixin B-agarose to remove impurities.

20. The method of claim 11, wherein impurities are removed after the eluting step c).

21. The method of claim 11, further comprising recovering the lipopolysaccharide from solution after the eluting step c).

22. The method of claim 21, wherein the lipopolysaccharide is recovered by freeze drying.

23. The method of claim 11, wherein the gram negative bacteria is a *Rhizobium etli*.

24. The method of claim 11, wherein the solution of the admixing step a) further comprises about 5% by volume of liquified phenol and wherein the resulting mixture is incubated at about 60° C. for about 15 minutes to about 2 hours.

25. A method of antagonizing gram negative bacterial endotoxic activity, comprising administering to a patient the lipopolysaccharide from a *Rhizobium etli* obtained from the method of claim 11.

26. The composition of claim 1, wherein the *Rhizobium etli* is *Rhizobium etli* bv. CE3, *Rhizobium etli* bv. CE109, *Rhizobium etli* bv. CE121, *Rhizobium etli* bv. CE350, *Rhizobium etli* bv. CE356, *Rhizobium etli* bv. CE357, *Rhizobium etli* bv. CE358, *Rhizobium etli* bv. CE359 or *Rhizobium etli* bv. CE360.

27. The composition of claim 3, wherein the *Rhizobium etli* is *Rhizobium etli* bv. CE3, *Rhizobium etli* bv. CE109, *Rhizobium etli* bv. CE121, *Rhizobium etli* bv. CE350, *Rhizobium etli* bv. CE356, *Rhizobium etli* bv. CE357, *Rhizobium etli* bv. CE358, *Rhizobium etli* bv. CE359 or *Rhizobium etli* bv. CE360.

28. The composition of claim 9, wherein the *Rhizobium etli* is *Rhizobium etli* bv. CE3, *Rhizobium etli* bv. CE109, *Rhizobium etli* bv. CE121, *Rhizobium etli* bv. CE350, *Rhizobium etli* bv. CE356, *Rhizobium etli* bv. CE357, *Rhizobium etli* bv. CE358, *Rhizobium etli* bv. CE359 or *Rhizobium etli* bv. CE360.

29. The composition of claim 10, wherein the *Rhizobium etli* is *Rhizobium etli* bv. CE3, *Rhizobium etli* bv. CE109, *Rhizobium etli* bv. CE121, *Rhizobium etli* bv. CE350, *Rhizobium etli* bv. CE356, *Rhizobium etli* bv. CE357, *Rhizobium etli* bv. CE358, *Rhizobium etli* bv. CE359 or *Rhizobium etli* bv. CE360.

* * * * *